US010059739B2

(12) United States Patent
Rajagopalan

(10) Patent No.: US 10,059,739 B2
(45) Date of Patent: Aug. 28, 2018

(54) NON-BENZENOID AROMATIC SYSTEMS FOR IMAGING, MONITORING AND THERAPY

(71) Applicant: MediBeacon Inc., St. Louis, MO (US)

(72) Inventor: Raghavan Rajagopalan, Solon, OH (US)

(73) Assignee: MEDIBEACON INC., St Louis, MO (US)

( * ) Notice: Subject to any disclaimer, the term of this patent is extended or adjusted under 35 U.S.C. 154(b) by 148 days.

(21) Appl. No.: 14/950,928

(22) Filed: Nov. 24, 2015

(65) Prior Publication Data

US 2016/0083426 A1    Mar. 24, 2016

Related U.S. Application Data

(62) Division of application No. 13/395,493, filed as application No. PCT/US2010/048347 on Sep. 10, 2010, now Pat. No. 9,226,980.

(60) Provisional application No. 61/241,624, filed on Sep. 11, 2009.

(51) Int. Cl.
| | |
|---|---|
| *A61B 10/00* | (2006.01) |
| *A61B 5/00* | (2006.01) |
| *A61B 8/00* | (2006.01) |
| *C07K 7/06* | (2006.01) |
| *A61K 41/00* | (2006.01) |
| *A61K 49/00* | (2006.01) |
| *C07C 247/14* | (2006.01) |
| *C07D 261/02* | (2006.01) |
| *C07D 261/04* | (2006.01) |
| *A61K 38/00* | (2006.01) |

(52) U.S. Cl.
CPC ............ *C07K 7/06* (2013.01); *A61K 41/0057* (2013.01); *A61K 49/0021* (2013.01); *A61K 49/0045* (2013.01); *A61K 49/0056* (2013.01); *C07C 247/14* (2013.01); *C07D 261/02* (2013.01); *C07D 261/04* (2013.01); *A61K 38/00* (2013.01)

(58) Field of Classification Search
CPC .... A61K 38/00; A61K 49/00; A61K 49/0045; A61K 49/0021; A61K 49/0056; A61K 41/00; A61K 41/0057; C07K 7/00; C07C 247/14; C07D 207/30; C07D 207/00; C07D 207/18; C07D 295/00; C07D 261/02; C07D 261/04
USPC .... 424/1.11, 1.49, 1.65, 1.69, 1.73, 9.1, 9.2, 424/9.3, 9.4, 9.5, 9.6; 514/1, 1.1, 19.2, 514/19.3, 19.4, 19.5, 19.6, 21.1, 21.2, 514/21.3, 21.4, 21.5, 21.6, 21.7, 21.8, 514/21.9; 530/300; 548/400, 560, 565
See application file for complete search history.

(56) References Cited

U.S. PATENT DOCUMENTS

| | | | |
|---|---|---|---|
| 5,846,730 A | 12/1998 | Miyazaki et al. | |
| 9,226,980 B2* | 1/2016 | Rajagopalan | ...... A61K 41/0057 |
| 2010/0311903 A1 | 12/2010 | Rajagopalan | |

FOREIGN PATENT DOCUMENTS

| | | |
|---|---|---|
| BR | 0305664 A1 | 10/2005 |
| CN | 101313898 A | 12/2008 |
| WO | 2007106142 A2 | 9/2007 |
| WO | 2007109809 A1 | 9/2007 |
| WO | 2008108944 A2 | 9/2008 |

OTHER PUBLICATIONS

Matsumura et al, Bulletin of the Chemical Society of Japan, 1962, vol. 35, pp. 677-680.*
Loidl G et al: "Synthesis of [beta]-(1-azulenyl)-L-alanine as a potential blue-colored fluorescent tryptophan analog and its use in peptide synthesis", Journal of Peptide Science. John Wiley and Sons Ltd. GB., vol. 6. Mar. 1, 2000 (Mar. 1, 2000), pp. 139-144.
Hayek R R A et al: "Comparative study between the effects of photodynamic therapy and conventional therapy on microbial reduction in ligature-induced peri-implantitis in dogs", Journal of Periodontology. American Academy of Periodontology. Chicago. IL., US. vol. 76. No. 8. Aug. 1, 2005 (Aug. 1, 2005), pp. 1275-1281.
Hafner K et al: "Zur Kenntnis Der Azulene, IV Azulen-Aldehyde and -Ketone", Justus Liebigs Annalen Der Chemie. Verlag Chemie GmbH. Weinheim; DE., vol. 625. Jan. 1, 1959 (Jan. 1, 1959), pp. 108-123.
Hafner K et al: "Synthese Von Azulen-Aldehyden Und -Ketonen", Angewandte Chemie. Wiley—V C H Verlag GmbH & Co. KGAA. Weinheim. DE. vol. 69. No. 16., Jan. 1, 1957 (Jan. 1, 1957). p. 533.
Bross P A et al: "Carbohydrate-Modi fi ed Conducting Polymers: Synthesis and Electrochemistry of Sugar-Linked Azulenes and Polyazulenes", Advanced Materials, Wiley VCH Verlag. DE. vol. 3. No. 4. Apr. 1, 1991 (Apr. 1, 1991), pp. 198-200.
Takagi K et al: "Synthesis of 1-Formylazulene Derivatives and Absorption Spectra of New Azomethine Dyes Containing an Azulene Ring", Dyes and Pigments. Elsevier Applied Science Publishers. Barking. GB. vol. 27, No. 3, Jan. 1, 1995 (Jan. 1, 1995), pp. 227-236.
Aumuller Ingo B et al: "Coloring Carbohydrates: Investigation of Azulene Derivatives as Blue Protecting Groups", Journal of Carbohydrate Chemistry, Taylor & Francis Inc. US, vol. 28, No. 6, Jan. 1, 2009 (Jan. 1, 2009), pp. 330-347.
Murata et al: "Fluorescence Yields of Azulene Dervivatives", Chem. Phys Letts, 1972 vol. 13, No. 2, pp. 101-102.
Liu: "Colorful Azulene and Its Equally Colorful Derivatives", J. Chem. Ed. 2002, vol. 79, No. 2, pp. 183-185.

(Continued)

*Primary Examiner* — D. L. Jones
(74) *Attorney, Agent, or Firm* — Armstrong Teasdale LLP

(57) ABSTRACT

This invention is directed to non-benzenoid aromatic compounds. Other aspects include methods of using non-benzenoid aromatic compounds for imaging and phototherapeutic uses thereof. Non-benzenoid compounds provided herein generally have one or more substituent groups which allow tailoring of the spectral properties or provide photoreactivity or targeting ability.

13 Claims, No Drawings
Specification includes a Sequence Listing.

(56) References Cited

OTHER PUBLICATIONS

Anderson et al: "Azulene, VI. Synthesis and Properties of Some 1,3-Disubstituted Azulenes", J. Org. Chem., 1957, vol. 22, pp. 1193-1196.

Anderson et al: "The Reaction of Azulenes with Trifluoro- and Trichloroacetic Anhydride", J. Org. Chem., 1962, vol. 27, pp. 3578-3581.

Anderson et al: "Azulene, II. Synthesis of Methyl 1-Azuloate", JACS., 1953, vol. 75, pp. 4979-4980.

Cowles: "The Effects of Substituents at the 1- and 3-Positions on the Visible Absorption Spectrum", JACS., 1957, vol. 79, pp. 1093-1095.

Hess et al.: "The Aromaticity of Heterocycles Containing the Imine Nitrogen", Tetrahedron,1975, vol. 31, pp. 295-298.

Anderson et al: "Some New Reactons and Derivatives of Azulene 1", J. Org. Chem., 1964, vol. 29, pp. 1373-1377.

Shevyakov et al.: "Orbital Control of the Color and Excited State Properties of Formylated and Fluorinated Derivatives of Azulene", J. Phys. Chem. A 2003, vol. 107, 3295-3299.

Hong Kim Jae et al. "Self-Assembling of Aminopyrazine Fluorescent Dyes and Their Solid State Spectra", Dyes and Pigments, 998, vol. 39, No. 4, pp. 341-357.

Shirai K et al., "Syntheses and Fluorescent Properties 0f 2,5-Diamino-3, 6-dicyanopyrazine Dyes", Dyes and Pigments, 1998, vol. 39, No. 1, pp. 49-68.

Loidl et al., Journal of Peptide Science, 2000, vol. 6, pp. 139-144.

\* cited by examiner

NON-BENZENOID AROMATIC SYSTEMS FOR IMAGING, MONITORING AND THERAPY

CROSS-REFERENCE TO RELATED APPLICATIONS

This application is a divisional of U.S. application Ser. No. 13/395,493, filed Mar. 30, 2012, which itself is a 371 national phase filing of PCT application no. PCT/US2010/048347, filed Sep. 10, 2010, which claims the benefit of priority of U.S. Provisional Applications No. 61/241,624, filed Sep. 11, 2009, the disclosures of which are hereby incorporated by reference as if written herein in their entireties.

INCORPORATION OF SEQUENCE LISTING

A copy of the Sequence Listing and a computer readable form of the sequence containing the file named "33693-192_Seq_Listing_ST25.txt", which is 582 bytes in size (as measured in MICROSOFT WINDOWS® EXPLORER), are provided herein and are herein incorporated by reference. This Sequence Listing consists of SEQ ID NO:1.

BACKGROUND

Optical agents currently play a central role in a large number of in vivo, in vitro and ex vivo clinical procedures including important diagnostic and therapeutic procedures. Photodiagnostic and phototherapeutic agents, for example, include a class of molecules capable of absorbing, emitting, and/or scattering electromagnetic radiation applied to a biological material, particularly in the visible and/or near infrared regions of the electromagnetic spectrum. This property of optical agents is used in a range of biomedical applications for visualizing, imaging or otherwise characterizing biological materials and/or achieving a desired therapeutic outcome. Recent developments in targeted administration and delivery of optical agents, and advanced systems and methods for applying and detecting electromagnetic radiation in biological environments has considerably expanded the applicability and effectiveness of optical agents for clinical applications.

Important applications of optical agents that absorb and/or emit in the visible and/or near-infrared (NIR) region of the electromagnetic spectrum include their use in biomedical imaging and visualization. For example, compounds absorbing and/or emitting light in these regions of the electromagnetic spectrum currently are useful for optical tomography, optoacoustic tomography, optical coherence tomography, confocal scanning laser tomography, optical coherence tomography, and fluorescence endoscopy; techniques which have emerged as essential molecular imaging techniques for imaging and visualizing biological processes at the organ, cellular and subcellular (e.g., molecular) levels. Biomedical images are generated, for example, by detecting electromagnetic radiation, nuclear radiation, acoustic waves, electrical fields, and/or magnetic fields transmitted, emitted and/or scattered by components of a biological sample. Modulation of the energy or intensity of the applied radiation yields patterns of transmitted, scattered and/or emitted radiation, acoustic waves, electrical fields or magnetic fields that contain useful anatomical, physiological, and/or biochemical information. A number of applications of biomedical imaging have matured into robust, widely used clinical techniques including planar projection and tomographic X-ray imaging, magnetic resonance imaging, ultrasound imaging, and gamma ray imaging.

Established optical imaging and visualization techniques are based on monitoring spatial variations in a variety of optical parameters including the intensities, polarization states, and frequencies of transmitted, reflected, and emitted electromagnetic radiation. Given that many biological materials of interest are incompatible with ultraviolet light, research is currently directed to developing and enhancing imaging techniques using visible and near infrared (NIR) radiation (from about 400 nm to about 900 nm). In particular, NIR light (700 nm to 900 nm) is useful for visualizing and imaging deeper regions than visible light because electromagnetic radiation of this wavelength range is capable of substantial penetration (e.g., up to four centimeters) in a range of biological media. Optical imaging and visualization using optical agents has potential to provide a less invasive and safer imaging technology, as compared to X-ray, and other widely used nuclear medicine technologies. Applications of optical imaging for diagnosis and monitoring of the onset, progression and treatment of various disease conditions, including cancer, are well established. (See, e.g., D. A. Benaron and D. K. Stevenson, *Optical time-of-flight and absorbance imaging of biologic media, Science,* 1993, 259, pp. 1463-1466; R. F. Potter (Series Editor), *Medical optical tomography: functional imaging and monitoring,* SPIE Optical Engineering Press, Bellingham, 1993; G. J. Tearney et al., *In vivo endoscopic optical biopsy with optical coherence tomography, Science,* 1997, 276, pp. 2037-2039; B. J. Tromberg et al., *Non-invasive measurements of breast tissue optical properties using frequency-domain photon migration, Phil. Trans. Royal Society London B,* 1997, 352, pp. 661-668; S. Fantini et al., *Assessment of the size, position, and optical properties of breast tumors in vivo by noninvasive optical methods, Appl. Opt.,* 1998, 37, pp. 1982-1989; A. Pelegrin et al., *Photoimmunodiagnosis with antibody-fluorescein conjugates: in vitro and in vivo preclinical studies, J. Cell Pharmacol.,* 1992, 3, pp. 141-145).

Optical agents for in vivo and in vitro biomedical imaging, anatomical visualization and monitoring organ function are described in International Patent Publication WO2008/108941; U.S. Pat. Nos. 5,672,333; 5,698,397; 6,167,297; 6,228,344; 6,748,259; 6,838,074; 7,011,817; 7,128,896, and 7,201,892. In this context, optical imaging agents are commonly used for enhancing signal-to-noise and resolution of optical images and extending these techniques to a wider range of biological settings and media. In addition, use of optical imaging agents having specific molecular recognition and/or tissue targeting functionality has also been demonstrated as effective for identifying, differentiating and characterizing discrete components of a biological sample at the organ, tissue, cellular, and molecular levels. Further, optical agents have been developed as tracers for real time monitoring of physiological function in a patient, including fluorescence-based monitoring of renal function. (See International Patent Publication PCT/US2007/0149478). Given their recognized utility, considerable research continues to be directed toward developing improved optical agents for biomedical imaging and visualization.

In addition to their important role in biomedical imaging and visualization, optical agents capable of absorption in the visible and NIR regions have also been extensively developed for clinical applications for phototherapy. The benefits of phototherapy using optical agents are widely acknowledged as this technique has the potential to provide efficacy comparable to radiotherapy, while entirely avoiding exposure of non-target organs and tissue to harmful ionizing radiation. Photodynamic therapy (PDT), in particular, has been used effectively for localized superficial or endoluminal malignant and premalignant conditions. The clinical efficacy of PDT has also been demonstrated for the treatment of various other diseases, injuries, and disorders, including cardiovascular disorders such as atherosclerosis and vascular restenosis, inflammatory diseases, ophthalmic diseases and dermatological diseases. Visudyne and Photofrin, for example, are two optical agents that have been developed for the treatment of macular degeneration of the eye and for ablation of several types of tumors, respectively. (See, e.g., Schmidt-Drfurth, U.; Bringruber, R.; Hasan, T. *Phototherapy in ocular vascular disease.* IEEE Journal of Selected Topics in Quantum Electronics 1996, 2, 988-996; Mlkvy, P.; Messmann, H.; Regula, J.; Conio, M.; Pauer, M.; Millson, C. E.; MacRobert, A. J.; Brown, S. G. *Phototherapy for gastrointestinal tumors using three photosensitizers— ALA induced PPIX, Photofrin, and MTHPC. A pilot study.* Neoplasma 1998, 45, 157-161; Grosjean, P.; Wagieres, G.; Fontolliet, C.; Van Den Bergh, H.; Monnier, P. *Clinical phototherapy for superficial cancer in the esophagus and the bronchi: 514 nm compared with 630 nm light irradiation after sensitization with Photofrin II.* British Journal of Cancer 1998, 77, 1989-1955; Mitton, D.; Ackroyd, R. Phototherapy of Barrett's oesophagus and oesophageal carcinoma—how I do it. Photodiagnostics and Phototherapy 2006, 3, 96-98; and Li, L.; Luo, R.; Liao, W.; Zhang, M.; Luo, Y.; Miao, J. Clinical study of photofrin phototherapy for the treatment of relapse nasopharyngeal carcinoma. Photodiagnostics and Phototherapy 2006, 3, 266-271; See, Zheng Huang "A Review of Progress in Clinical Photodynamic Therapy", Technol Cancer Res Treat. 2005 June; 4(3): 283-293; "Photodiagnosis and Photodynamic Therapy", Brown S, Brown E A, Walker I. The present and future role of photodynamic therapy in cancer treatment. Lancet Oncol. 2004; 5:497-508; Triesscheijn M, Baas P, Schellens J H M. "Photodynamic Therapy in Oncology"; The Oncologist. 2006; 11:1034-1044; and Dougherty T J, Gomer C J, Henderson B W, Jori G, Kessel D, Korbelik M, Moan J, Peng Q. Photodynamic Therapy. J. Natl. Cancer Inst. 1998; 90:899-905).

Phototherapy is carried out by administration and delivery of a photosensitizer to a therapeutic target tissue (e.g., tumor, lesion, organ, etc.) followed by photoactivation of the photosensitizer by exposure to applied electromagnetic radiation. Phototherapeutic procedures require photosensitizers that are relatively chemically inert, and become activated only upon irradiation with light of an appropriate wavelength. Selective tissue injury can be induced with light when photosensitizers bind to the target tissues, either directly or through attachment to a bioactive carrier or targeting moiety. Photosensitizers essentially operate via two different pathways, classified as Types 1 and 2. A primary distinction between these classes of photosensitizers is that the Type 1 process operates via direct energy or electron transfer from the photosensitizer to the cellular components thereby inducing cell death, whereas the Type 2 process involves first the conversion of singlet oxygen from the triplet oxygen found in the cellular environment followed by either direct reaction of singlet oxygen with the cellular components or further generating secondary reactive species (e.g. peroxides, hydroxyl radical, etc.) which will induce cell death.

The Type 1 mechanism proceeds via a multistep process involving activation of the photosensitizer by absorption of electromagnetic radiation followed by direct interaction of the activated photosensitizer, or reactive intermediates derived from the photosensitizer, with the target tissue, for example via energy transfer, electron transfer or reaction with reactive species (e.g., radicals, ions, nitrene, carbene, etc.) resulting in tissue damage. The Type 1 mechanism can be schematically represented by the following sequence of reactions:

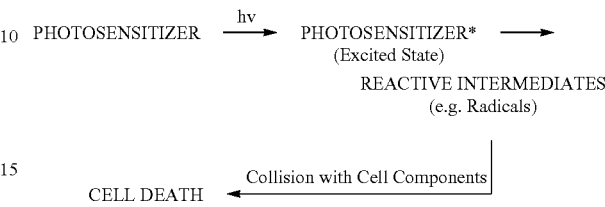

wherein hv indicates applied electromagnetic radiation and (PHOTOSENSITIZER)* indicates excited state of the photosensitizer. The Type 2 mechanism proceeds via a three-step process involving activation of the photosensitizer by absorption of electromagnetic radiation followed by energy transfer from the activated photosensitizer to oxygen molecules in the environment of the target tissue. This energy transfer process generates excited state oxygen ($^1O_2$) which subsequently interacts with the target tissue so as to cause tissue damage. The Type 2 mechanism can be schematically represented by the following sequence of reactions:

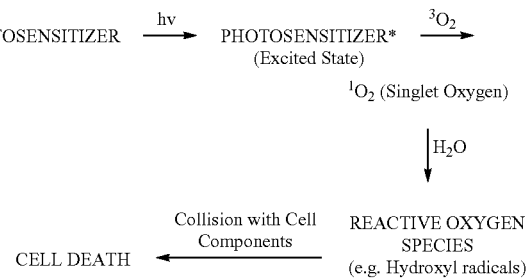

wherein hv indicates applied electromagnetic radiation, (PHOTOSENSITIZER)* indicates photoactivated photosensitizer, $^3O_2$ is ground state triplet oxygen, and $^1O_2$ is excited state singlet oxygen.

The biological basis of tissue injury brought about by tumor phototherapeutic agents has been the subject of intensive study. Various biochemical mechanisms for tissue damage have been postulated, which include the following: a) cancer cells up-regulate the expression of low density lipoprotein (LDL) receptors, and phototherapy (PDT) agents bind to LDL and albumin selectively; (b) porphyrin-like substances are selectively taken up by proliferative neovasculature; (c) tumors often contain increased number of lipid bodies and are thus able to bind to hydrophobic photosensitizers; (d) a combination of "leaky" tumor vasculature and reduced lymphatic drainage causes porphyrin accumulation referred to as "EPR" (enhanced permeability and retention) effect; (e) tumor cells may have increased capabilities for phagocytosis or pinocytosis of porphyrin aggregates; (f) tumor associated macrophages may be largely responsible for the concentration of photosensitizers in tumors; and (g) cancer cells may undergo apoptosis induced by photosensitizers. Among these mechanisms, (f) and (g) are the most general and, of these two alternatives, there is a general consensus that (f) is the most likely mechanism by which the phototherapeutic effect of porphyrin-like compounds is induced.

Much of the research in the past several decades has focused on developing phototherapeutic agents based on the Type 2 (PDT) mechanism. Surprisingly, there has been considerably less attention devoted to Type 1 phototherapeutic agents despite the fact that there are numerous classes of compounds that could potentially be useful for phototherapy that function via this mechanism. Unlike Type 2, the Type 1 process does not require oxygen; and hence Type 1 photosensitizers are expected to be potentially more effective than Type 2 photosensitizers under hypoxic environments typically found in solid tumors. Second, the Type 1 mechanism involves two steps (photoexcitation and direct energy transfer), whereas the Type 2 mechanism involves three steps (photoexcitation, singlet oxygen generation, and energy transfer). Further, studies have recently shown that production of high levels of reactive oxygen species can induce an anti-inflammatory response, which may result in blood vessels to become more "leaky," thereby increasing the risk of metastasis (Chen, B.; Pogue, B.; Luna, J. M.; Hardman, R. L.; Hoopes, P. J.; Hasan, T. Tumor vascular permeabilization by vascular-targeting photosensitization: effects, mechanism, and therapeutic implications. Clinical Cancer Research 2006, 12(3, Pt. 1), 917-923). Targeted Type 1 photosensitizers, by their very nature, are not expected to produce reactive oxygen species; rather, the reactive species produced by these photosensitizers will immediately react with the cellular component at the binding site and trigger cell death. Type 2 phototherapeutic agents, however, do have certain advantages over Type 1 agents. For example, Type 2 agents can potentially be catalytic, i.e., the Type 2 photosensitizer is regenerated once the energy transfer to the oxygen has taken place. In contrast, Type 1 process would generally be expected to require stoichiometric amounts of the photosensitizer in some clinical settings. Table I provides a summary of the attributes of Type 1 and Type 2 phototherapeutic agents. Given these attributes, it is clear that development of safe and effective Type 1 phototherapeutic agents would be useful to complement the existing therapeutic approaches provided by Type 2 agents, and to enhance the therapeutic portfolio available for clinicians.

TABLE 1

Comparison between Type 1 and Type 2 processes for phototherapy.

| TYPE 1 PROCESS | TYPE 2 PROCESS |
| --- | --- |
| Two-step process. | Three-step process. |
| Not well explored. | Very well studied. |
| Light of any wavelength can be used. | Requires red light for optimal performance. |
| Does not require oxygen. | Requires oxygen. |
| Large classes of compounds. | Limited classes of compounds. |
| Stoichiometric. | Potentially catalytic. |
| Intramolecular energy transfer to generate reactive species. | Intermolecular energy transfer to generate reactive oxygen species. |
| No products in the market. | Two products are in use. |

Specific optical, chemical and pharmacokinetic properties of optical agents are necessary for their effective use in Type 1 and Type 2 phototherapeutic applications. For example, optical agents for these applications preferably have strong absorption in the visible or NIR regions, and also exhibit low systemic toxicity, low mutagenicity, and rapid clearance from the blood stream. These optical agents must also be compatible with effective administration and delivery to the target tissue, for example by having reasonable solubilities and a low tendency for aggregation in solution. Upon excitation by absorption of visible and NIR electromagnetic radiation, optical agents for Type 1 and 2 phototherapy preferably provide large yields of singlet oxygen (Type 2) or other reactive species, such as free radicals or ions, capable of causing local tissue damage. Both Type 1 and Type 2 photosensitizers typically undergo photoactivation followed by intersystem crossing to their lowest triplet excited state, and therefore, a relatively long triplet lifetime is usually beneficial for providing effective tissue damage. Other useful properties of optical agents for these applications include chemical inertness and stability, insensitivity of optical properties to changes in pH, and compatibility with conjugation to ligands providing targeted delivery via molecular recognition functionality. Multifunctional optical agents have also been developed for phototherapy that are capable of providing both imaging and visual functionality upon excitation at a first range of wavelengths and phototherapeutic functionality upon excitation at a second range of wavelength. (See, U.S. Pat. No. 7,235,685 and International Patent Publication WO 2007/106436).

Optical agents for phototherapeutic applications preferably exhibit a high degree of selectivity for the target tissue. Selectivity provided by optical agents facilitates effective delivery to a target tissue of interest and provides a means of differentiating different tissue classes during therapy. Selective tissue injury can be induced with light when photosensitizers bind to the target tissues either directly, as in the case of Photofrin, or through attachment to a bioactive carrier, or through in situ biochemical synthesis of the photosensitizer in localized area, as in the case of 2-aminolevulinic acid, which is an intermediate in the biosynthesis of porphyrin. Previous studies have shown that certain dyes localize in tumors and serve as a powerful probe for the detection and treatment of small cancers. (D. A. Belinier et al., Murine pharmacokinetics and antitumor efficacy of the photodynamic sensitizer 2[I-hexyloxyethyl]-2-devinyl pyropheophorbide-a, J. Photochem. Photobiol., 1993, 20, pp. 55-61; G. A. Wagnieres et al., In vivo fluorescence spectroscopy and imaging for oncological applications, Photochem. Photobiol., 1998, 68, pp. 603-632; J. S. Reynolds et al., Imaging of spontaneous canine mammary tumors using fluorescent contrast agents, Photochem. Photobiol., 1999, 70, pp. 87-94). It is generally recognized, however, that many of these dyes do not localize preferentially in malignant tissues. A number of strategies have been developed for imparting selectivity and/or targeting functionality by incorporation of a molecular recognition component in the optical agent. For example, targeting of fluorescent dyes to tumors has been demonstrated by us and others using dye conjugates with antibodies and peptides for diagnostic imaging of tumors. (See, Achilefu et al., Novel receptor-targeted fluorescent contrast agents for in vivo imaging of tumors, Investigative Radiology, 2000, 35, pp. 479-485; Ballou et al., Tumor labeling in vivo using cyanine conjugated monoclonal antibodies, Cancer Immunology and Immunotherapy, 1995, 41, pp. 257-263; and Licha et al., New contrast agent for optical imaging: acid cleavable conjugates of cyanine dyes with biomolecules, in Biomedical Imaging: Reporters, Dyes and Instrumentation, Proceedings of SPIE, 1999, 3600, pp. 29-35). Therefore, receptor-target mediated phototherapy agents provide a promising pathway for achieving site selective activation at various target tissues.

For both photodiagnostic and phototherapeutic applications, optical agents preferably exhibit a high degree of selectivity for the target tissue. Selectivity provided by optical agents facilitates effective delivery to a target tissue of interest and provides a means of differentiating different tissue classes during imaging, visualization and therapy. There is a considerable need for developing optical agents for biomedical applications that have high absorption/emission properties in the visible and NIR regions, high photostability, insensitivity to pH, and wavelength tunability, as well as selectivity for the target tissue.

SUMMARY

The invention relates generally to optical agents for biomedical applications, including imaging, diagnosing and/or treating medical conditions. Compounds provided absorb and emit spectral energy in the visible, near infrared, and/or any other wavelength range useful for optical detection in medical procedures. The invention includes optical agents and related therapeutic methods, comprising non-benzenoid aromatic compounds having substituent groups which allow tailoring of the spectral properties and/or provide photoreactivity and/or targeting ability.

In embodiments, compounds of the invention have the formula (FX1):

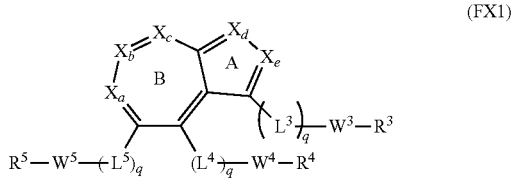

(FX1)

wherein:

$X_a$ is N or —C-$(L^6)_q$-$W^6$—$R^6$;
$X_b$ is N or —C-$(L^7)_q$-$W^7$—$R^7$;
$X_c$ is N or —C-$(L^8)_q$-$W^8$—$R^8$;
$X_d$ is N or —C-$(L^1)_q$-$W^1$—$R^1$;
$X_e$ is N or —C-$(L^2)_q$-$W^2$—$R^2$;

each of $L^1$ to $L^8$ is independently $C_1$-$C_{10}$ alkylene, $C_3$-$C_{10}$ cycloalkylene, $C_2$-$C_{10}$ alkenylene, $C_3$-$C_{10}$ cycloalkenylene, $C_2$-$C_{10}$ alkynylene, ethenylene, ethynylene, phenylene, 1-aza-2,5-dioxocyclopentylene, —$(CH_2CH_2O)_m$—, —$(CHOH)_m$—, or 1,4-diazacyclohexylene;

each m is independently an integer selected from the range of 1 to 100;

each q is independently 0 or 1;

each of $W^1$ to $W^8$ is independently a single bond, —$(CH_2)_n$—, —$O(CH_2)_n$—, —$(CH_2)_nO$—, —$(HCCH)_n$—, —O—, —S—, —SO—, —$SO_2$—, —$SO_3^-$—, —$OSO_2$—, —$NR^9$—, —CO—, —COO—, —OCO—, —OCOO—, —$CONR^{10}$—, —$NR^{11}CO$—, —$OCONR^{12}$—, —$NR^{13}COO$—, —$NR^{14}CONR^{15}$—, —$NR^{16}CSNR^{17}$—, —$O(CH_2)_n$—, —$S(CH_2)_n$—, —$NR^{18}(CH_2)_n$—, —$CO(CH_2)_n$—, —$COO(CH_2)_n$—, —$OCO(CH_2)_n$—, —$OCOO(CH_2)_n$—, —$CONR^{19}(CH_2)_n$—, —$CONR^{20}(CH_2)_n(OCH_2CH_2)_u$—, —$NR^{21}CO(CH_2)_n$—, —$OCONR^{22}(CH_2)_n$—, —$NR^{23}COO(CH_2)_n$—, —$NR^{24}CONR^{25}(CH_2)_n$—, —$NR^{26}CSNR^{27}(CH_2)_n$—, —$O(CH_2)_nNR^{28}CO(CH_2)_n$—, —$CO(CH_2)_n(CH_2OCH_2)(CH_2)_nNR^{29}(CH_2)_nNR^{30}CO$—, —$NR^{69}SR^{70}$—, or —$CO(CH_2)_nNR^{31}CO$—;

each n is independently an integer selected from the range of 1 to 10;

each of $R^9$ to $R^{31}$ and each of $R^{69}$ to $R^{70}$ is independently hydrogen, $C_1$-$C_{20}$ alkyl, or $C_5$-$C_{30}$ aryl;

each of $R^1$ to $R^8$ is independently hydrogen, $C_1$-$C_{20}$ alkyl, $C_5$-$C_{30}$ aryl, $C_1$-$C_{20}$ acyl, $C_2$-$C_{20}$ alkenyl, $C_2$-$C_{20}$ alkynyl, $C_5$-$C_{20}$ alkylaryl, $C_1$-$C_6$ alkoxycarbonyl, halo, halomethyl, dihalomethyl, trihalomethyl, —CN, —$CO_2R^{32}$, —$OCONR^{33}R^{34}$, —$COR^{35}$, —$NO_2$, —$SOR^{36}$, —$OSR^{37}$, —$SO_2R^{38}$, —$SO_2OR^{39}$, —$SO_2NR^{40}R^{41}$, —$PO_3R^{42}R^{43}$, —$OR^{44}$, —$SR^{45}$, —$NR^{46}R^{47}$, —$NR^{48}COR^{49}$, —$CH_2(CHOH)_nR^5$, —$(CH_2CH_2O)_uR^{51}$, —$CH(R^{52})CO_2H$, —$CH(R^{53})NH_2$, $TG^1$ to $TG^8$, $PS^1$ to $PS^8$, or $FL^1$ to $FL^8$;

each u is independently an integer selected from the range of 1 to 25;

each of $R^{32}$ to $R^{55}$ is independently hydrogen or $C_1$-$C_{10}$ alkyl;

each of $TG^1$ to $TG^8$ is independently an amino acid, a peptide, a protein, a nucleoside, a nucleotide, an enzyme, a carbohydrate, a glycomimetic, an oligomer, a lipid, a polymer, an antibody, an antibody fragment, a mono- or polysaccharide comprising 1 to 50 carbohydrate units, a glycopeptide, a glycoprotein, a peptidomimetic, a drug, a drug mimic, a hormone, a receptor, a metal chelating agent, a radioactive or nonradioactive metal complex, a mono- or polynucleotide comprising 1 to 50 nucleic acid units, a polypeptide comprising 2 to 30 amino acid units, or an echogenic agent;

each of $PS^1$ to $PS^8$ is independently a photosensitizing moiety capable of producing one or more free radicals, nitrenes, carbenes, and/or singlet oxygen, and wherein each of $PS^1$ to $PS^8$ comprises at least one azide, azo, diazo, oxaza, diaza, dithia, thioxa, dioxa, phthalocyanine, rhodamine, or porphyrin group; and each of $FL^1$ to $FL^8$ is independently a fluorescent moiety selected from naphthoquinones, anthracenes, anthraquinones, phenanthrenes, tetracenes, naphthacenediones, pyridines, quinolines, isoquinolines, indoles, isoindoles, pyrroles, imidazoles, pyrazoles, pyrazines, purines, benzimidazoles, benzofurans, dibenzofurans, carbazoles, acridines, acridones, phenanthridines, thiophenes, benzothiophenes, dibenzothiophenes, xanthenes, xanthones, flavones, coumarins, phenoxazines, phenothiazines, phenoselenazines, cyanines, indocyanines, and azo compounds; wherein any adjacent $R^1$ to $R^8$ may combine, optionally with one or two —$CR^{54}R^{55}$ groups, to form $C_3$-$C_7$ cycloalkyl, $C_3$-$C_7$ heterocycloalkyl, $C_6$ aryl, or $C_5$-$C_6$ heteroaryl;

wherein at least one of $R^1$ to $R^8$ is $C_1$-$C_{10}$ alkyl, —$OR^{44}$, —$SR^{45}$, —$NR^{46}R^{47}$, or —$NR^{48}COR^{49}$; and wherein at least one of $R^1$ to $R^8$ is halo, trihalomethyl, —CN, —$CO_2R^{32}$, —$OCONR^{33}R^{34}$, —$COR^{35}$, —$NO_2$, —$SOR^{36}$, —$OSR^{37}$, —$SO_2R^{38}$, —$SO_2NR^{40}R^{41}$, or $C_1$-$C_{10}$ acyl; or wherein at least one of -$(L^1)_q$-$W^1$—$R^1$, -$(L^2)_q$-$W^2$—$R^2$, -$(L^3)_q$-$W^3$—$R^3$, -$(L^4)_q$-$W^4$—$R^4$, -$(L^5)_q$-$W^5$—$R^5$, -$(L^6)_q$-$W^6$—$R^6$, -$(L^7)_q$-$W^7$—$R^7$, or -$(L^8)_q$-$W^8$—$R^8$ includes —$(OCH_2CH_2)_u$—.

In an embodiment, at least one of $R^1$ to $R^8$ is independently $C_1$-$C_6$ alkyl, —$OR^{44}$, —$SR^{45}$, —$NR^{46}R^{47}$, or —$NR^{48}COR^{49}$. In an embodiment, at least one of $R^1$ to $R^8$ is independently halo, trihalomethyl, —CN, —$CO_2R^{32}$, —$CONR^{33}R^{34}$, —$COR^{35}$, —$NO_2$, —$SOR^{36}$, —$SO_2R^{38}$, or —$SO_2NR^{40}R^{41}$. In an embodiment, at least one of $R^1$ to $R^8$ is independently a targeting group $TG^1$ to $TG^8$. In an embodiment, at least one of $R^1$ to $R^8$ is independently a photosensitizer $PS^1$ to $PS^8$. In an embodiment, at least one of $R^1$ to $R^8$ is independently a fluorophore $FL^1$ to $FL^8$. In an embodiment, at least one $PS^1$ to $PS^8$ comprises an azide, azo, diazo, oxaza, diaza, thioxa, phthalocyanine, rhodamine or porphyrin group.

In an embodiment, at least one of -(L$^1$)$_q$-W$^1$—R$^1$, -(L$^2$)$_q$-W$^2$—R$^2$, -(L$^3$)$_q$-W$^3$—R$^3$, -(L$^4$)$_q$-W$^4$—R$^4$, -(L$^5$)$_q$-W$^5$—R$^5$, -(L$^6$)$_q$-W$^6$—R$^6$, -(L$^7$)$_q$-W$^7$—R$^7$, or -(L$^8$)$_q$-W$^8$—R$^8$ includes a —(OCH$_2$CH$_2$)$_u$— group.

In the embodiment where any adjacent R$^1$ to R$^8$ may combine, optionally with one or two —CR$^{54}$R$^{55}$ groups, to form C$_3$-C$_7$ cycloalkyl, C$_3$-C$_7$ heterocycloalkyl, C$_6$ aryl, or C$_5$-C$_6$ heteroaryl, the C$_3$-C$_7$ cycloalkyl, C$_3$-C$_7$ heterocycloalkyl, C$_6$ aryl, or C$_5$-C$_6$ heteroaryl groups may be optionally substituted with one or more substituents. The optional substituents may include, for example, one or more of C$_1$-C$_{20}$ alkyl, C$_5$-C$_{30}$ aryl, C$_1$-C$_{20}$ acyl, C$_2$-C$_{20}$ alkenyl, C$_2$-C$_{20}$ alkynyl, C$_5$-C$_{20}$ alkylaryl, C$_1$-C$_6$ alkoxycarbonyl, halo, halomethyl, dihalomethyl, trihalomethyl, —CN, —CO$_2$R$^{32}$, —CONR$^{33}$R$^{34}$, —COR$^{35}$, —NO$_2$, —SOR$^{36}$, —OSR$^{37}$, —SO$_2$R$^{38}$, —SO$_2$OR$^{39}$, —SO$_2$NR$^{40}$R$^{41}$, —PO$_3$R$^{42}$R$^{43}$, —OR$^{44}$, —SR$^{45}$, —NR$^{46}$R$^{47}$, —NR$^{48}$COR$^{49}$, —CH$_2$(CHOH)$_n$R$^{50}$, —(CH$_2$CH$_2$O)$_u$R$^{51}$, —CH(R$^{52}$)CO$_2$H, —CH(R$^{53}$)NH$_2$, TG$^1$ to TG$^8$, PS$^1$ to PS$^8$, or FL$^1$ to FL$^8$, where each of R$^{32}$ to R$^{55}$ is independently hydrogen or C$_1$-C$_{10}$ alkyl and TG$^1$ to TG$^8$, PS$^1$ to PS$^8$, and FL$^1$ to FL$^8$ are each as defined above for Formula (FX1). In an embodiment where any adjacent R$^1$ to R$^8$ may combine, optionally with one or two —CR$^{54}$R$^{55}$ groups, to form C$_3$-C$_7$ heterocycloalkyl, or heteroaryl, the C$_3$-C$_7$ heterocycloalkyl, or C$_5$-C$_6$ heteroaryl groups may contain one or more heteroatoms which may be the same or different.

In an embodiment, the invention provides compounds having formula (FX2) to (FX6) where the variables are as defined above for formula (FX1):

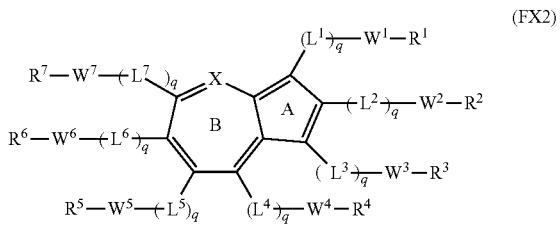

(FX2)

wherein X is N or —C-(L$^8$)$_q$-W$^8$—R$^8$;

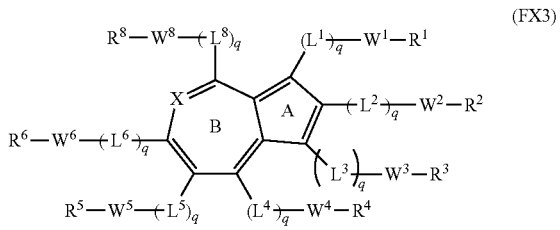

(FX3)

wherein X is N or —C-(L$^7$)$_q$-W$^7$—R$^7$;

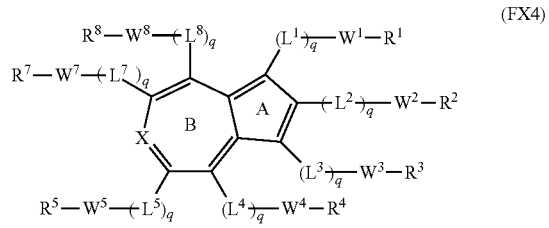

(FX4)

wherein X is N or —C-(L$^6$)$_q$-W$^6$—R$^6$;

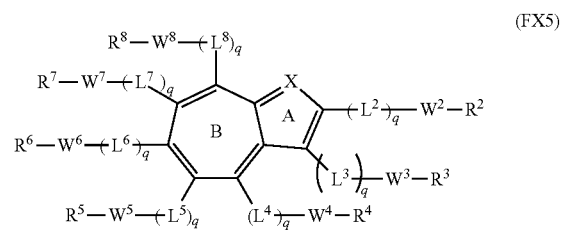

(FX5)

wherein X is N or —C-(L)$_q$-W$^1$—R$^1$; or

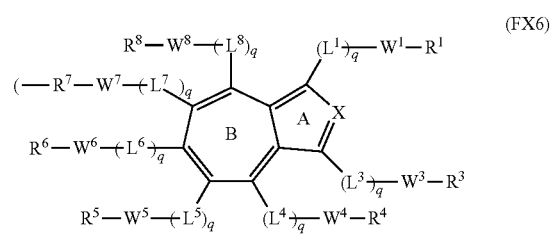

(FX6)

wherein X is N or —C-(L$^2$)$_q$-W$^2$—R$^2$.

In an embodiment, the invention provides compounds having formula (FX7) to (FX12), where the variables are as defined above for formula (FX1):

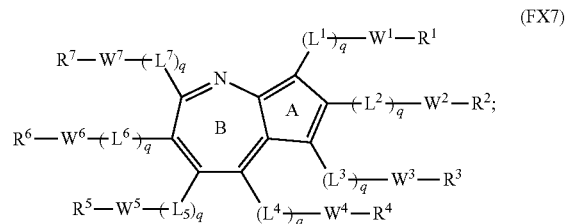

(FX7)

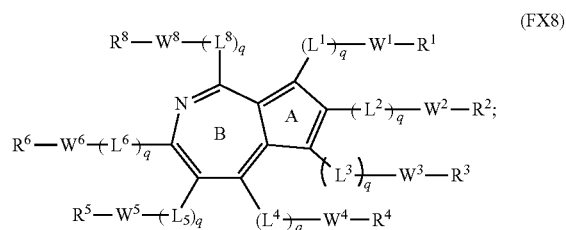

(FX8)

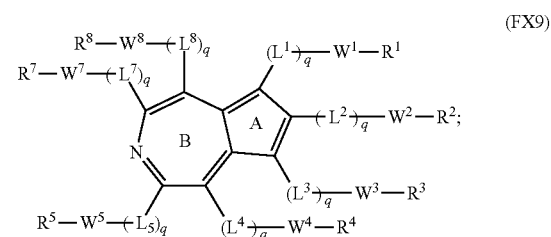

(FX9)

(FX10)

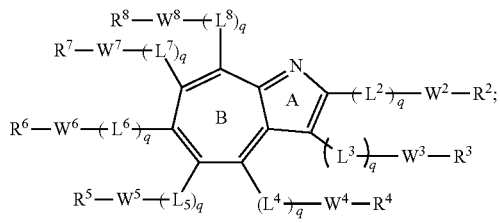

(FX11)

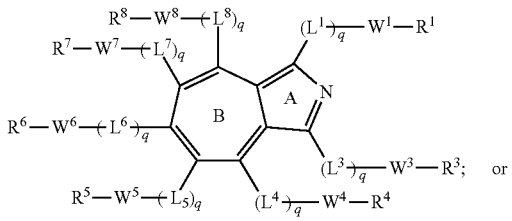

or (FX12)

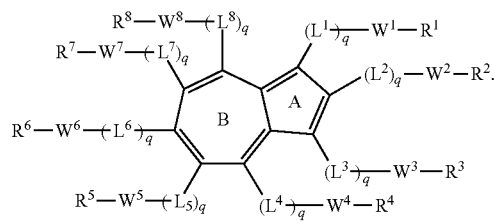

In an embodiment, the invention provides a compound having formula (FX2), (FX5), (FX10) or (FX11).

In an embodiment, the invention provides compounds having formulas (FX13) to (FX17) where the variables are as defined above for formula (FX1):

(FX13)

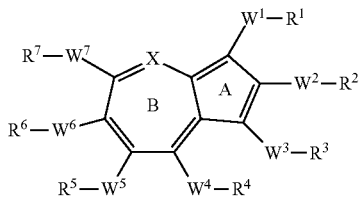

wherein X is N or —C—$W^8$—$R^8$;

(FX14)

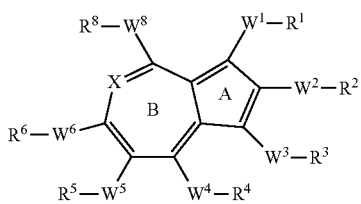

wherein X is N or —C—$W^7$—$R^7$;

(FX15)

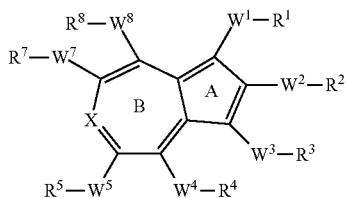

wherein X is N or —C—$W^6$—$R^6$;

(FX16)

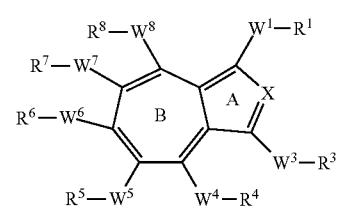

wherein X is N or —C—$W^1$—$R^1$;

(FX17)

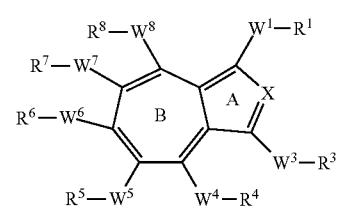

wherein X is N or —C—$W^2$—$R^2$.

$L^1$-$L^8$ and $W^1$—$W^8$ may be attaching and spacer groups, respectively, for providing an appropriate linkage between $R^1$-$R^8$ and the non-benzenoid aromatic ring core of compounds (FX1) to (FX17). In some embodiments, any or all of $L^1$-$L^8$ or $W^1$-$W^8$ may be present or absent. If a $L^1$-$L^8$ or $W^1$-$W^8$ is absent, there is a single bond between the substituents which are present. For example, in an embodiment, the invention provides compounds useful as optical agents for phototherapeutic methods having formula (FX1) wherein at least one of $L^1$-$L^8$ is a single bond, and wherein at least one q is 0, thereby providing direct coupling of a $W^1$-$W^8$, if present, or $R^1$-$R^8$ to the backbone structure of the compound. In an embodiment, the invention provides compounds useful as optical agents for phototherapeutic methods wherein at least one of $W^1$-$W^8$ is a single bond, providing direct coupling of at least one $R^1$-$R^8$ to $L^1$-$L^8$, if present, or to the backbone structure of the compound. In an embodiment, for example, the invention provides compounds useful as optical agents for phototherapeutic methods having formula (FX1), wherein all q variables are 0, and wherein each of $L^1$-$L^8$ is a single bond.

In an embodiment, the invention provides compounds with electron-donating and electron-withdrawing groups attached to adjacent positions of the backbone. In an aspect of this embodiment, provided are compounds of formula (FX1) to (FX17) wherein (a) one of $R^1$ and $R^2$ is $C_1$-$C_{10}$ alkyl, —$OR^{44}$, —$SR^{45}$, —$NR^{46}R^{47}$, or —$NR^{48}COR^{49}$, and the other of $R^1$ and $R^2$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl;

(b) one of $R^2$ and $R^3$ is $C_1$-$C_{10}$ alkyl, —$OR^{44}$, —$SR^{45}$, —$NR^{46}R^{47}$, or —$NR^{48}COR^{49}$, and the other of $R^2$ and $R^3$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl;

(c) one of $R^3$ and $R^4$ is $C_1$-$C_{10}$ alkyl, —$OR^{44}$, —$SR^{45}$, —$NR^{46}R^{47}$, or —$NR^{48}COR^{49}$, and the other of $R^3$ and $R^4$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl;

(d) one of $R^4$ and $R^5$ is $C_1$-$C_{10}$ alkyl, —$OR^{44}$, —$SR^{45}$, —$NR^{46}R^{47}$, or —$NR^{48}COR^{49}$, and the other of $R^4$ and $R^5$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl;

(e) one of $R^5$ and $R^6$ is $C_1$-$C_{10}$ alkyl, —$OR^{44}$, —$SR^{45}$, —$NR^{46}R^{47}$, or —$NR^{48}COR^{49}$, and the other of $R^5$ and $R^6$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl;

(f) one of $R^6$ and $R^7$ is $C_1$-$C_{10}$ alkyl, —$OR^{44}$, —$SR^{45}$, —$NR^{46}R^{47}$, or —$NR^{48}COR^{49}$, and the other of $R^6$ and $R^7$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl; or (g) one of $R^7$ and $R^8$ is $C_1$-$C_{10}$ alkyl, —$OR^{44}$, —$SR^{45}$, —$NR^{46}R^{47}$, or —$NR^{48}COR^{49}$, and the other of $R^7$ and $R^8$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl.

In an embodiment, the invention provides compounds with electron-donating and electron-withdrawing groups attached to non-adjacent positions providing continuous conjugation between the electron-donating and electron withdrawing groups. In an aspect of this embodiment, the invention provides compounds of formula (FX1) to (FX17), wherein (a) one of $R^1$ and $R^5$ is $C_1$-$C_{10}$ alkyl, —$OR^{44}$, —$SR^{45}$, —$NR^{46}R^{47}$, or —$NR^{48}COR^{49}$, and the other of $R^1$ and $R^5$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl;

(b) one of $R^1$ and $R^7$ is $C_1$-$C_{10}$ alkyl, —$OR^{44}$, —$SR^{45}$, —$NR^{46}R^{47}$, or —$NR^{48}COR^{49}$, and the other of R and $R^7$ is halo, trihalomethyl, —CN, —$C_2R^{32}$, —$CONR^{33}R^{34}$, —$COR^{35}$, —$NO_2$, —$SOR^{36}$, —$S_2R^{38}$, —$SO_2NR^{40}R^{41}$, or $C_1$-$C_{10}$ acyl;

(c) one of $R^2$ and $R^4$ is $C_1$-$C_{10}$ alkyl, —$OR^{44}$, —$SR^{45}$, —$NR^{46}R^{47}$, or —$NR^{48}COR^{49}$, and the other of $R^2$ and $R^4$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl;

(d) one of $R^2$ and $R^6$ is $C_1$-$C_{10}$ alkyl, —$OR^{44}$, —$SR^{45}$, —$NR^{46}R^{47}$, or —$NR^{48}COR^{49}$, and the other of $R^2$ and $R^6$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl;

(e) one of $R^2$ and $R^8$ is $C_1$-$C_{10}$ alkyl, —$OR^{44}$, —$SR^{45}$, —$NR^{46}R^{47}$, or —$NR^{48}COR^{49}$, and the other of $R^2$ and $R^8$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl;

(f) one of $R^3$ and $R^5$ is $C_1$-$C_{10}$ alkyl, —$OR^{44}$, —$SR^{45}$, —$NR^{46}R^{47}$, or —$NR^{48}COR^{49}$, and the other of $R^3$ and $R^5$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl; or (g) one of $R^4$ and $R^7$ is $C_1$-$C_{10}$ alkyl, —$OR^{44}$, —$SR^{45}$, —$NR^{46}R^{47}$, or —$NR^{48}COR^{49}$, and the other of $R^4$ and $R^7$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl.

In an embodiment, the invention provides compounds of formula (FX1) to (FX17), wherein at least one of $R^1$ to $R^8$ is $C_1$-$C_6$ alkyl, —$OR^{44}$, —$SR^{45}$, —$NR^{46}R^{47}$, or —$NR^{48}COR^{49}$. In an embodiment, the invention provides compounds of formula (FX1) to (FX17), wherein at least one of $R^1$ to $R^8$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_1$-$C_{10}$ acyl. In an embodiment the invention provides compounds of formula (FX1) to (FX17), wherein at least one of $R^1$ to $R^8$ is $TG^1$ to $TG^8$. In an embodiment the invention provides compounds of formula (FX1) to (FX17), wherein at least one of $R^1$ to $R^8$ is $PS^1$ to $PS^8$. In an embodiment the invention provides compounds of formula (FX1) to (FX17), wherein at least one of $R^1$ to $R^8$ is $FL^1$ to $FL^8$. In an embodiment, the invention provides compounds of formula (FX1) to (FX17), wherein at least one of the substituent arms on rings A and B contains a polyethylene glycol (PEG) group. In embodiments, the PEG group provides increased water solubility over a compound that does not contain a PEG group. In embodiments, the PEG group is abbreviated —$(OCH_2CH_2)_u$— where u is an integer from 1 to 25. The PEG group can be incorporated as a part of other substituent variables as provided herein.

In an embodiment, compounds of the invention include compounds having the numbering scheme described below,

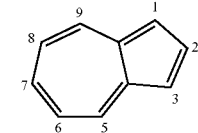

wherein groups at one or more odd numbered positions 1, 3, 5, 7 and 9 comprise hydrogen or electron withdrawing groups and groups at one or more even numbered positions comprise hydrogen or halogen. In embodiment, groups at one or more even numbered positions include halogen. In an embodiment, groups at one or more even numbered groups include fluorine.

In an embodiment, the invention provides compounds of formula (FX1) to (FX17), wherein the compound comprises at least one electron withdrawing group and at least one electron donating group. In an embodiment, the invention provides compounds of formula (FX1) to (FX17), having R group substituent pairings where one of the pair comprises an electron-withdrawing group and the other of the pair comprises an electron-donating group. In an aspect of this embodiment, the R group substituent pairings are ($R^1$ and $R^2$); ($R^2$ and $R^3$); ($R^3$ and $R^4$); ($R^4$ and $R^5$); ($R^5$ and $R^6$); ($R^6$ and $R^7$); ($R^7$ and $R^8$); ($R^8$ and $R^1$); ($R^1$ and $R^5$), ($R^1$ and $R^7$); ($R^2$ and $R^4$); ($R^2$ and $R^6$); ($R^2$ and $R^8$); ($R^3$ and $R^5$); or ($R^4$ and $R^7$), wherein one of the identified R groups in the substituent pairings is $C_1$-$C_{10}$ alkyl, —$OR^{28}$, —$SR^{29}$, —$NR^{30}R^{31}$, or —$NR^{32}COR^{33}$ and the other of the identified R groups in the substituent pairings is halo, trihalomethyl, —CN, —$CO_2R^{18}$, —$CONR^{19}R^{20}$, —$COR^{21}$, —$NO_2$, —$SOR^{22}$, —$SO_2R^{24}$, or —$SO_2NR^{26}R^{27}$.

The invention includes, for example, compounds comprising one or more fluorescent moieties (or fluorophores).

In an embodiment, the invention provides compounds of formulas (FX1) to (FX17) wherein at least one of $R^1$ to $R^8$ independently comprises a fluorescent moiety (abbreviated as FL herein). In an aspect of this embodiment, a fluorescent moiety is a group corresponding to a naphthoquinone, an anthraquinone, a naphthacenedione, a pyrazine, an acridine, an acridone, a phenanthridine, a dibenzothiophene, a xanthene, a xanthone, a flavone, a coumarin, a phenoxazine, a phenothiazine, a phenoselenazine, a cyanine, an indocyanine, or an azo compound. The invention includes compounds having formulas (FX1) to (FX17) that do not include a FL group. The invention includes compounds having formulas (FX1) to (FX17) that include a FL group and one or more of photosensitizing moiety or targeting group.

The invention includes, for example, compounds having a photosensitizing moiety (or photosensitizer) capable of producing one or more free radicals, nitrenes, carbenes, and/or singlet oxygen. Methods for using photosensitizing moieties to produce free radicals, nitrenes, carbenes, and/or singlet oxygen are known in the art. In an embodiment, the invention provides compounds of formulas (FX1) to (FX17) wherein at least one of $R^1$ to $R^8$ independently comprises a photosensitizing moiety (abbreviated as PS herein). In an aspect of this embodiment, a photosensitizer moiety, if present, independently is a group corresponding to an azide, an azo, a diazo, an oxaza, a diaza, a thioxa, a phthalocyanine, a rhodamine, or a porphyrin group. The invention includes compounds having formulas (FX1) to (FX17) that do not include a PS group. The invention includes compounds having formulas (FX1) to (FX17) that include a PS group and one or more of fluorescent moiety or targeting group.

The invention includes, for example, compounds having a targeting ligand or other molecular recognition component for delivering the optical agent to a selected organ, tissue, or other cell material (targeting group). In an embodiment, the invention provides compounds of formulas (FX1) to (FX17), wherein at least one of $R^1$ to $R^8$ independently comprises a targeting group (abbreviated as TG herein). In an embodiment, a targeting group, if present, is independently an amino acid, a peptide, a protein, a nucleoside, a nucleotide, an enzyme, a carbohydrate, a glycomimetic, an oligomer, a lipid, a polymer, an antibody, an antibody fragment, a mono- or polysaccharide comprising 1 to 50 carbohydrate units, a glycopeptide, a glycoprotein, a peptidomimetic, a drug, a drug mimic, a hormone, a receptor, a metal chelating agent, a radioactive or nonradioactive metal complex, a mono- or polynucleotide comprising 1 to 50 nucleic acid units, a polypeptide comprising 2 to 30 amino acid units, or an echogenic agent. In an embodiment, a targeting group, if present, is independently an amino acid, a peptide, a protein, a nucleoside, a nucleotide, an enzyme, an antibody, an antibody fragment, a saccharide, a glycopeptide, a peptidomimetic, a drug, a drug mimic, or a hormone. Incorporation of a targeting group or molecular recognition component in some compounds and methods of the invention enables targeted delivery such that at least a portion of phototherapeutic agent administered to a subject accumulates at a desired site, such as the site of an organ, tissue, tumor or other lesion, prior to or during exposure to electromagnetic radiation. The invention includes compounds having formulas (FX1) to (FX17) that do not have a TG group The invention includes compounds having formulas (FX1) to (FX17) that include a TG group and one or more of photosensitizing moiety or fluorescent moiety. In an aspect of the present invention, a compound of the invention is targeted to a selected organ in the subject. In an aspect of the present invention, a compound of the invention is targeted to a selected tissue type in the subject. In an aspect of the present invention, the targeted tissue type is colon, renal, prostate, gastric, esophageal, uterine, endometrial, pancreatic, breast, cervical, brain, skin, gallbladder, lung, or ovary. In an aspect of the invention, the tissue type is renal.

In an embodiment, the invention provides compounds of formulas (FX1) to (FX17), wherein one of $X_a$, $X_b$, $X_c$, $X_d$ and $X_e$ is N. In an embodiment, the invention provides compounds of formulas (FX1) to (FX17), wherein none of $X_a$, $X_b$, $X_c$, $X_d$ and $X_e$ is N.

In an aspect of the present invention, the present invention is directed to a method of performing a medical imaging procedure on a patient. The method comprises administering to a subject an effective amount of a compound of the invention under conditions sufficient for contacting the compound with a target cell; and exposing the administered compound to electromagnetic radiation. In another aspect, the invention is directed to a method of performing a phototherapeutic procedure on a patient. The method comprises administering to a subject an effective amount of the compound under conditions sufficient for contacting the compound with the target cell; and exposing the administered compound to electromagnetic radiation. In an aspect of the present invention, the medical imaging procedure or phototherapeutic procedure comprises exposing the administered compound to electromagnetic radiation having wavelengths selected over a range of 400 nanometers to 1300 nanometers. In an aspect of the present invention, the medical imaging procedure or phototherapeutic procedure comprises detecting electromagnetic radiation emitting from the compound in the subject. In an aspect of the medical imaging procedure or phototherapeutic procedure of the present invention, exposing the compound administered to the subject to electromagnetic radiation changes an optical property of the compound. In an aspect of the invention, the change in optical property of the compound administered from exposure to electromagnetic radiation is measured or monitored. In an embodiment of this aspect of the invention, exposing the compound administered to the subject to electromagnetic radiation increases the fluorescence intensity of the compound. In an embodiment of this aspect of the invention, exposing the compound administered to the subject to electromagnetic radiation changes the absorption spectrum of the compound. In a further aspect, the present invention is directed to a method of performing a medical imaging procedure on a patient, wherein the medical imaging procedure comprises: (a) administering to a subject an effective amount of the compound under conditions sufficient for contacting the compound with a target cell; (b) exposing the administered compound to electromagnetic radiation; and (c) detecting acoustic energy emitting from the compound in the subject. In embodiments, the compounds useful in the methods of the invention are compounds of formulae (FX1) to (FX17). In embodiments, the compounds useful in the methods of the invention are compounds of formula (FX18):

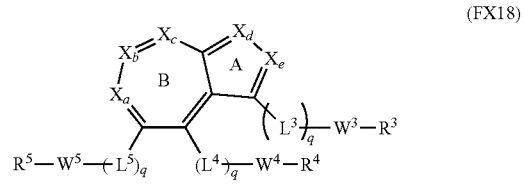

(FX18)

wherein:

$X_a$ is N or —C-$(L^6)_q$-$W^6$—$R^6$;
$X_b$ is N or —C-$(L^7)_q$-$W^7$—$R^7$;
$X_c$ is N or —C-$(L^8)_q$-$W^8$—$R^8$;
$X_d$ is N or —C-$(L^1)_q$-$W^1$—$R^1$;
$X_e$ is N or —C-$(L^2)_q$-$W^2$—$R^2$;

each of $L^1$ to $L^8$ is independently $C_1$-$C_{10}$ alkylene, $C_3$-$C_{10}$ cycloalkylene, $C_2$-$C_{10}$ alkenylene, $C_3$-$C_{10}$ cycloalkenylene, $C_2$-$C_{10}$ alkynylene, ethenylene, ethynylene, phenylene, 1-aza-2,5-dioxocyclopentylene, —$(CH_2CH_2O)_m$—, —$(CHOH)_m$—, or 1,4-diazacyclohexylene;

each m is independently an integer selected from the range of 1 to 100;

each q is independently 0 or 1;

each of $W^1$ to $W^8$ is independently a single bond, —$(CH_2)_n$—, —$O(CH_2)_n$—, —$(CH_2)_nO$—, —$(HCCH)_n$—, —O—, —S—, —SO—, —$SO_2$—, —$SO_3^-$—, —$OSO_2$—, —$NR^9$—, —CO—, —COO—, —OCO—, —OCOO—, —$CONR^{10}$—, —$NR^{11}CO$—, —$OCONR^{12}$—, —$NR^{13}COO$—, —$NR^{14}CONR^{15}$—, —$NR^{16}CSNR^{17}$—, —$O(CH_2)_n$—, —$S(CH_2)_n$—, —$NR^{18}(CH_2)_n$—, —CO$(CH_2)_n$—, —COO$(CH_2)_n$—, —OCO$(CH_2)_n$—, —OCOO$(CH_2)_n$—, —$CONR^{19}(CH_2)_n$—, —$CONR^{20}(CH_2)_n(OCH_2CH_2)_u$—, —$NR^{21}CO(CH_2)_n$—, —$OCONR^{22}(CH_2)_n$—, —$NR^{23}COO(CH_2)_n$—, —$NR^{24}CONR^{25}(CH_2)_n$—, —$NR^{26}CSNR^{27}(CH_2)_n$—, —$O(CH_2)_nNR^{28}CO(CH_2)_n$—, —$CO(CH_2)_n(CH_2OCH_2)_n(CH_2)_nNR^{29}(CH_2)_nNR^{30}CO$—, —$NR^{69}SR^{70}$—, or —$CO(CH_2)_nNR^{31}CO$—;

each n is independently an integer selected from the range of 1 to 10;

each of $R^9$ to $R^{31}$ and each of $R^{69}$ to $R^{70}$ is independently hydrogen, $C_1$-$C_{20}$ alkyl, or $C_5$-$C_{30}$ aryl;

each of $R^1$ to $R^8$ is independently hydrogen, $C_1$-$C_{20}$ alkyl, $C_5$-$C_{30}$ aryl, $C_1$-$C_{20}$ acyl, $C_2$-$C_{20}$ alkenyl, $C_2$-$C_{20}$ alkynyl, $C_5$-$C_{20}$ alkylaryl, $C_1$-$C_6$ alkoxycarbonyl, halo, halomethyl, dihalomethyl, trihalomethyl, —CN, —$CO_2R^{32}$, —$CONR^{33}R^{34}$, —$COR^{35}$, —$NO_2$, —$SOR^{36}$, —$OSR^{37}$, —$SO_2R^{38}$, —$SO_2OR^{39}$, —$SO_2NR^{40}R^{41}$, —$PO_3R^{42}R^{43}$, —$OR^{44}$, —$SR^{45}$, —$NR^{46}R^{47}$, —$NR^{48}COR^{49}$, —$CH_2(CHOH)_nR^{50}$, —$(CH_2CH_2O)_uR^{51}$, —$CH(R^{52})CO_2H$, —$CH(R^{53})NH_2$, $TG^1$ to $TG^8$, $PS^1$ to $PS^8$, or $FL^1$ to $FL^8$;

each u is independently an integer selected from the range of 1 to 25;

each of $R^{32}$ to $R^{55}$ is independently hydrogen or $C_1$-$C_{10}$ alkyl;

each of $TG^1$ to $TG^8$ is independently an amino acid, a peptide, a protein, a nucleoside, a nucleotide, an enzyme, a carbohydrate, a glycomimetic, an oligomer, a lipid, a polymer, an antibody, an antibody fragment, a mono- or polysaccharide comprising 1 to 50 carbohydrate units, a glycopeptide, a glycoprotein, a peptidomimetic, a drug, a drug mimic, a hormone, a receptor, a metal chelating agent, a radioactive or nonradioactive metal complex, a mono- or polynucleotide comprising 1 to 50 nucleic acid units, a polypeptide comprising 2 to 30 amino acid units, or an echogenic agent;

each of $PS^1$ to $PS^8$ is independently a photosensitizing moiety capable of producing one or more free radicals, nitrenes, carbenes, and/or singlet oxygen, and wherein each of $PS^1$ to $PS^8$ comprises at least one azide, azo, diazo, oxaza, diaza, dithia, thioxa, dioxa, phthalocyanine, rhodamine, or porphyrin group; and each of $FL^1$ to $FL^8$ is independently a fluorescent moiety selected from naphthoquinones, anthracenes, anthraquinones, phenanthrenes, tetracenes, naphthacenediones, pyridines, quinolines, isoquinolines, indoles, isoindoles, pyrroles, imidiazoles, pyrazoles, pyrazines, purines, benzimidazoles, benzofurans, dibenzofurans, carbazoles, acridines, acridones, phenanthridines, thiophenes, benzothiophenes, dibenzothiophenes, xanthenes, xanthones, flavones, coumarins, phenoxazines, phenothiazines, phenoselenazines, cyanines, indocyanines, and azo compounds;

wherein any adjacent $R^1$ to $R^8$ may combine, optionally with one or two —$CR^{54}R^{55}$ groups, to form $C_3$-$C_7$ cycloalkyl, $C_3$-$C_7$ heterocycloalkyl, $C_6$ aryl, or $C_5$-$C_6$ heteroaryl. In embodiments, where substituent groups and various aspects of formulae (FX1) to (FX17) are described, these substituent groups and various aspects are intended to apply to compounds of formula (FX18).

The present invention further includes compositions comprising enantiomers, diastereomers and/or ionic forms (e.g., protonated and deprotonated forms) of the compounds of formulae (FX1) to (FX17), and related methods of using compounds of formulae (FX1) to (FX17), for example in a biomedical procedure. The present invention further includes compositions comprising enantiomers, diastereomers and/or ionic forms (e.g., protonated and deprotonated forms) of the compounds of formula (FX18), and related methods of using compounds of formula (FX18), for example in a biomedical procedure.

In some embodiments, the present invention is directed to a non-benzenoid aromatic compound having at least one electron withdrawing group (EWG) and at least one electron donating group (EDG) bonded directly or indirectly to a carbon atom of the non-benzenoid ring core. In some embodiments, an electron withdrawing group and an electron donating group are positioned on adjacent carbon atoms of the non-benzenoid ring core. In some embodiments, an electron withdrawing group and an electron donating group are positioned on non-adjacent carbon atoms of the non-benzenoid ring core. Multiple electron withdrawing groups and/or electron donating groups bonded directly or indirectly to a carbon atom of the non-benzenoid ring core are contemplated by this invention.

The present invention provides methods of making and using compounds, including compounds of formulas (FX1) to (FX18). Methods of this aspect of the present invention include in vivo, in vitro and ex vivo methods for biomedical and bioanalytical applications. Methods of the present invention include photodiagnostic and phototherapeutic methods, such as optical imaging, anatomical visualization, endoscopic visualization, image guided surgery, and Type 1 and Type 2 phototherapy of tumors and other lesions. For some compounds for use in vivo, in vitro or ex vivo for imaging or visualizing, the tissue, organs and/or cells is a tumor, tumor site, or other lesion.

In an embodiment, the present invention provides pharmaceutical compositions of a therapeutically effective amount of one or more compounds described herein, or their pharmaceutically acceptable salts.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

Various features discussed herein in relation to one or more of the exemplary embodiments may be incorporated into any of the described aspects of the present invention alone or in any combination. Certain exemplary aspects of the invention are set forth herein. It should be understood that these aspects are presented merely to provide the reader with a brief summary of certain forms the invention might take and that these aspects are not intended to limit the scope of the invention. Indeed, the invention may encompass a variety of aspects that may not be explicitly set forth herein as would be understood by one of ordinary skill in the relevant art without undue experimentation.

DETAILED DESCRIPTION

In general, the terms and phrases used herein have their art-recognized meaning, which can be found by reference to standard texts, journal references and contexts known to those skilled in the art. The following definitions are provided to clarify their specific use in the context of the invention.

The term "amino acid" comprises naturally occurring amino acids as well as non-naturally occurring amino acids, including amino acid analogs and derivatives. One skilled in the art will recognize that reference herein to an amino acid comprises, for example, naturally occurring proteogenic L-amino acids; D-amino acids; chemically modified amino acids such as amino acid analogs and derivatives; naturally occurring non-proteogenic amino acids, and chemically synthesized compounds having properties known in the art to be characteristic of amino acids. Amino acids include glycine, alanine, valine, leucine, isoleucine, methionine, proline, phenylalanine, tryptophan, asparagine, glutamine, glycine, serine, threonine, serine, rhreonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids.

The term "nucleic acid" as used herein generally refers to a molecule or strand of DNA, RNA, or derivatives or analogs thereof including one or more nucleobases. Nucleobases comprise purine or pyrimidine bases typically found in DNA or RNA (e.g., adenine, guanine, thymine, cytosine, and/or uracil). The term "nucleic acid" also comprises oligonucleotides and polynucleotides. Nucleic acids may be single-stranded molecules, or they may be double-, triple- or quadruple-stranded molecules that may comprise one or more complementary strands of a particular molecule. "Nucleic acid" includes artificial nucleic acids including peptide nucleic acids, morpholino nucleic acids, glycol nucleic acids and threose nucleic acids. Artificial nucleic acids may be capable of nucleic acid hybridization.

As used herein, "sequence" means the linear order in which monomers occur in a polymer, the order of amino acids in a polypeptide or the order of nucleotides in a polynucleotide for example.

The terms "peptide" and "polypeptide" are used synonymously in the present description, and refer to a class of compounds composed of amino acid residues chemically bonded together by amide bonds (or peptide bonds), regardless of length, functionality, environment, or associated molecule(s) Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methionine oxidation, alkylation, acylation, carbamylation, iodination and the addition of cofactors. Peptides include proteins and further include compositions generated by degradation of proteins, for example by proteolyic digestion. Peptides and polypeptides can be generated by substantially complete digestion or by partial digestion of proteins. Polypeptides comprising 2 to 100 amino acid units, optionally for some embodiments 2 to 50 amino acid units and, optionally for some embodiments 2 to 20 amino acid units can be used as polypeptide targeting ligands in the invention, for example, where the polypeptide preferentially binds to proteins, peptides or other biomolecules expressed, or otherwise generated by, a target tissue, such as a tumor, precancerous tissue, site of inflammation or other lesion. Typically, the polypeptide is at least four amino acid residues in length and can range up to a full-length protein.

"Target tissue" refers to tissue of a subject to which an optical agent is administered or otherwise contacted, for example during a biomedical procedure such as an optical imaging, phototherapy, monitoring or visualization procedure. Target tissues can be contacted with an optical agent of the invention under in vivo conditions or ex vivo conditions. Target tissues in some embodiments include cancerous tissue, cancer cells, precancerous tissue, a tumor, a lesion, a site of inflammation, or vasculature tissue. In some embodiments, a target tissue includes a melanoma cell, a breast lesion, a prostate lesion, a lung cancer cell, a colorectal cancer cell, an atherosclerotic plaque, a brain lesion, a blood vessel lesion, a lung lesion, a heart lesion, a throat lesion, an ear lesion, a rectal lesion, a bladder lesion, a stomach lesion, an intestinal lesion, an esophagus lesion, a liver lesion, a pancreatic lesion, and a solid tumor. Target tissue in some embodiments refers to a selected organ of the subject or component thereof, such as lung, heart, brain, stomach, liver, kidneys, gallbladder, pancreas, intestines, rectum, skin, colon, prostate, ovaries, breast, bladder, blood vessel, throat, ear, or esophagus.

"Protein" refers to a class of compounds comprising one or more polypeptide chains and/or modified polypeptide chains. Proteins can be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methionine oxidation, the addition of cofactors, proteolysis, and assembly of proteins into macromolecular complexes. Modification of proteins can also include non-naturally occurring derivatives, analogues and functional mimetics generated by chemical synthesis. Exemplary derivatives include chemical modifications such as alkylation, acylation, carbamylation, iodination or any modification that derivatizes the protein.

As used herein, "polynucleotide" and "oligonucleotide" are used interchangeably and refer to a class of compounds composed of nucleic acid residues chemically bonded together. The invention provides optical agents having an oligonucleotide or polynucleotide targeting ligand which comprises a plurality of nucleic acid residues, such as DNA or RNA residues, and/or modified nucleic acid residues that preferentially binds to proteins, peptides or other biomolecules expressed, or otherwise generated by, a target tissue, such as a tumor, precancerous tissue, site of inflammation or other lesion. Modifications to nucleic acid residues can be naturally occurring or non-naturally occurring, such as modifications generated by chemical synthesis. Oligo- or poly-nucleotide targeting ligands include, for example, oligo- or poly-nucleotides comprising 1 to 100 nucleic acid units, optionally for some embodiments 1 to 50 nucleic acid units and, optionally for some embodiments 1 to 20 nucleic acid units. Polypeptide and oligonucleotide include a polymer of at least two nucleotides joined together by phosphodiester bonds and may consist of either ribonucleotides or deoxyribonucleotides.

"Peptidomimetic" refers to a small molecule having activity, including biological activity that resembles that of a polypeptide. Morphine, for example, is a peptidomimetic of endorphin peptide. In some embodiments, a peptidomimetic is a small protein-like polymer designed to mimic the functionality of a peptide. Peptidomimetics useful as targeting ligands for some compounds of the invention in the present invention include peptoids and β-peptides.

The term "carbocyclic" refers to ring structures containing only carbon atoms in the ring. Carbon atoms of carbocyclic rings can be bonded to a wide range of other atoms and functional groups.

The term "alicyclic" refers to a ring that is not an aromatic ring. Alicyclic rings include both carbocyclic and heterocyclic rings.

The term "heterocyclic" refers to ring structures containing at least one other kind of atom, in addition to carbon, in the ring. Examples of such atoms include nitrogen, oxygen and sulfur. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, preferably 1 to 4, and more preferably for some embodiments 1 to 3.

As used herein, a "non-benzenoid aromatic" compound or derivative is an aromatic compound having two or more fused non-benzene rings as a core structure. Examples of non-benzenoid aromatic compounds include azulene and azaazulene. Non-benzenoid aromatic compounds are also referred to as non-benzenoid compounds herein.

"Optical agent" generally refers to compounds, compositions, preparations, and/or formulations that absorb, emit, or scatter electromagnetic radiation of wavelength, generally in the range of 400-900 nanometers, within a biologically relevant environment or condition. Optical agents optionally have molecular recognition or targeting functions enabling localized delivery to a target tissue. In some embodiments, optical agents of the present invention, when excited by electromagnetic radiation, undergo emission via fluorescence or phosphorescence pathways. These pathways are useful for diagnostic imaging, visualization, or organ function monitoring. Compounds belonging to this class are commonly referred to as "optical imaging agents" or "optical contrast agents." In some other embodiments, optical agents of the present invention absorb electromagnetic radiation and undergo photochemical reactions such as photofragmentation of one or more photolabile bonds to generate reactive intermediates such as nitrenes, carbine, free radicals, or ions. This process is useful for phototherapy of tumors or other lesions. Compounds belonging to this class are commonly referred to as "photosensitizers."

Optical agents of the present invention include, but are not limited to, contrast agents, imaging agents, dyes, detectable agents, photosensitizer agents, photoactivators, and photoreactive agents; and conjugates, complexes, and derivatives thereof. Optical agents of the present invention include non-benzenoid derivatives having a non-benzenoid ring core structure and derivatives thereof. Some optical agents of the present invention provide detectable agents that can be administered to a subject and subsequently detected using a variety of optical techniques, including optical imaging, visualization, and other forms of optical detection.

Optical agents of the present invention can contain fluorophores. The term "fluorophore" generally refers to a component or moiety of a molecule or group which causes a molecule or group to be fluorescent. Fluorophores can be functional groups in a molecule which absorb electromagnetic radiation of first specific wavelengths and re-emit energy at second specific wavelengths. The amount and wavelengths of the emitted electromagnetic radiation depend on both the fluorophore and the chemical environment of the fluorophore. The term "fluorophore" is abbreviated throughout the present description as "FL". In aspects of the invention, fluorophores emit energy in the visible (e.g. 350 nm to 750 nm) and NIR regions (e.g., 750-1300 nm) of the electromagnetic spectrum.

As used herein, a "chromophore" is a compound or functional group of a compound that absorbs electromagnetic radiation, preferably for some applications electromagnetic radiation having wavelengths in the UV (e.g. 200 nm to 350 nm) or visible (e.g. 350 nm to 750 nm) of the electromagnetic spectrum.

As used herein, an "electron withdrawing group" (EWG) refers to any chemical group that draws electrons from a center, such as the non-benzenoid core of the present invention. In an embodiment, electron withdrawing group(s) as substituent groups for the compositions of formulae (FX1) to (FX18) are independently selected from the group consisting of: cyano (—CN), carbonyl (—CO), carboxylate (—CO$_2$R$^{50}$), carbamate (—CONR$^{51}$R$^{52}$), halo (—F, —Cl, —Br, —I, —At), acyl (—COR$^{53}$), nitro (—NO$_2$), sulfinyl (—SOR$^{54}$), —OSR$^{55}$, sulfonyl (—SO$_2$R$^{56}$, —SO$_2$OR$^{57}$, and —SO$_2$NR$^{58}$R$^{59}$), and —PO$_3$R$^{60}$R$^{61}$, wherein R$^{50}$-R$^{61}$ are in some instances independently selected to enhance biological and/or physiochemical properties of the non-benzenoid derivatives of the present invention. In some instances, R$^{50}$-R$^{61}$ are independently any one of a hydrogen atom, an anionic functional group (e.g., carboxylate, sulfonate, sulfate, phosphonate or phosphate) or a hydrophilic functional group (e.g., hydroxyl, carboxyl, sulfonyl, sulfonato or phosphonato). In other instances, R$^{50}$-R$^{61}$ are independently hydrogen, C$_{1-10}$ alkyl, aryl, heteroaryl, —(CH$_2$)$_a$OH, —(CH$_2$)$_a$CO$_2$H, —(CH$_2$)$_a$SO$_3$H, —(CH$_2$)$_a$SO$_3^-$, —(CH$_2$)$_a$OSO$_3$H, —(CH$_2$)$_a$OSO$_3^-$, —(CH$_2$)$_a$NHSO$_3$H, —(CH$_2$)$_a$NHSO$_3^-$, —(CH$_2$)$_a$PO$_3$H$_2$, —(CH$_2$)$_a$PO$_3$H—, —(CH$_2$)$_a$PO$_3^{2-}$, —(CH$_2$)$_a$OPO$_3$H$_2$, —(CH$_2$)$_a$OPO$_3$H— or —(CH$_2$)$_a$OPO$_3$ where a is an integer from 1 to 10. In one example of this embodiment, the EWG(s) are independently —CN, —CO$_2$R$^{50}$, —CONR$^{51}$R$^{52}$, —COR$^{53}$, —NO$_2$, or —SO$_2$R$^{56}$. In an embodiment, an EWG is located at the terminus of a substituent arm of a non-benzenoid aromatic compound of the present invention.

As used herein, an "electron donating group" (EDG) refers to any chemical group that releases electrons to a center, such as the non-benzenoid core of the present invention. In an embodiment, electron donating group(s) as substituent groups for the compositions of formulae (FX1) to (FX18) are independently selected from the group consisting of: C$_1$-C$_{10}$ alkyl, C$_5$-C$_{10}$ aryl, —(CH$_2$)$_n$OH—OR$^{62}$, —SR$^{63}$, —NR$^{64}$R$^{65}$, —N(R$^{66}$)COR$^{67}$, and —P(R$^{68}$) wherein R$^{62}$-

$R^{68}$ are in some instances independently selected to enhance biological and/or physiochemical properties of the non-benzenoid core of the present invention. n is selected from the range of 1 to 10. In some instances, $R^{62}$-$R^{68}$ are independently any one of a hydrogen atom, an anionic functional group (e.g., carboxylate, sulfonate, sulfate, phosphonate and phosphate) or a hydrophilic functional group (e.g., hydroxyl, carboxyl, sulfonyl, sulfonato and phosphonato). In other instances, $R^{62}$-$R^{68}$ are independently hydrogen, $C_{1-10}$ alkyl, aryl, heteroaryl, —$(CH_2)_aOH$, —$(CH_2)_aCO_2H$, —$(CH_2)_aSO_3H$, —$(CH_2)_aSO_3^-$, —$(CH_2)_aOSO_3H$, —$(CH_2)_aOSO_3^-$, —$(CH_2)_aNHSO_3H$, —$(CH_2)_aNHSO_3^-$, —$(CH_2)_aPO_3H_2$, —$(CH_2)_aPO_3H-$, —$(CH_2)_aPO_3^{2-}$, —$(CH_2)_aOPO_3H_2$, —$(CH_2)_aOPO_3H-$ or —$(CH_2)_aOPO_3$ where a is an integer from 1 to 10. In one example of this embodiment, the EDG(s) are independently —$OR^{62}$, —$SR^{63}$, —$NR^{64}R^{65}$, or —$N(R^{66})COR^{67}$. In an embodiment, an EDG is located at the terminus of a substituent arm of a non-benzenoid aromatic compound of the present invention.

As used throughout the present description, the expression "a group corresponding to" an indicated species expressly includes a radical, including monovalent, divalent and polyvalent radicals. for example, an aromatic or heterocyclic aromatic radical, of the groups listed provided in a covalently bonded configuration, optionally with one or more substituents, including but not limited to electron donating groups, electron withdrawing groups and/or targeting ligands.

In an embodiment, an effective amount of a compound or composition of the invention is a therapeutically effective amount. As used herein, the phrase "therapeutically effective" qualifies the amount of compound administered in the therapy. This amount achieves the goal of ameliorating, suppressing, eradicating, preventing, reducing the risk of, or delaying the onset of the targeted condition.

In an embodiment, an effective amount of a compound or composition of the invention is a diagnostically effective amount. As used herein, the phrase "diagnostically effective" qualifies the amount of compound administered in diagnosis. The amount achieves the goal of being detectable while avoiding adverse side effects found with higher doses. In an embodiment, an active ingredient or other component is included in a therapeutically acceptable amount. In an embodiment, an active ingredient or other component is included in a diagnostically acceptable amount.

"Photosensitizing moiety", "photosensitizers" and "phototherapeutic agents" are used interchangeably and refer to a class of optical agents that absorb electromagnetic radiation and undergo photochemical reactions, such as photofragmentation of one or more photolabile bonds, to generate reactive intermediates for achieving a desired therapeutic result. Phototherapeutic agents include compounds that absorb visible and/or near infrared radiation and generate one or more nitrenes, carbene, free radicals, singlet oxygen and/or ions. Phototherapeutic agents are useful for a wide range of phototherapy applications, for example in the treatment of tumors or other lesions. Photosensitizers include Type 1 and Type 2 phototherapeutic agents.

"Optical condition" refers to one or more of the following: the fluorescence quantum yield, fluorescence intensity, fluorescence excitation wavelength, wavelength distribution or spectrum, emission wavelength, wavelength distribution or spectrum, Stokes shift, color, reflectance, phosphorescence, chemiluminescence, scattering, and/or other observable and/or measurable spectral property or phenomenon.

"Phototherapy procedure" refers to a therapeutic procedure involving administration of a phototherapeutic agent compound of the invention which comprises a photosensitizing moiety to a patient followed by subsequent excitation of the phototherapeutic agent by exposure to applied electromagnetic radiation, such as electromagnetic radiation having wavelengths in the visible and/or near IR region of the electromagnetic spectrum, such as wavelengths in the range of 400-1300 nanometers. Phototherapy includes, but is not limited to, photodynamic therapy. Phototherapeutic agents of the invention can also comprise one or more of targeting groups, fluorescent moieties, electron withdrawing groups, electron donating groups, and other groups.

As used herein, the term "pharmaceutically acceptable salt" can refer to acid addition salts or base addition salts of the compounds in the present disclosure. A pharmaceutically acceptable salt is any salt which retains the activity of the parent compound and does not impart any deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, -32-cilexetil, citric, edetic, edisylic, estolic, esyl, esylic, formic, fumaric, glucaptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like. Pharmaceutically acceptable salts may be derived from amino acids, including but not limited to cysteine. Other pharmaceutically acceptable salts may be found, for example, in Stahl et al., Handbook of Pharmaceutical Salts: Properties, Selection, and Use, Wiley-VCH; Verlag Helvetica Chimica Acta, Zurich, 2002. (ISBN 3-906390-26-8).

When used herein, the term "diagnosis", "diagnostic" and other root word derivatives are as understood in the art and are further intended to include a general monitoring, characterizing and/or identifying a state of health, physical state, or disease. The term is meant to encompass the concept of prognosis. For example, the diagnosis of cancer can include an initial determination and/or one or more subsequent assessments regardless of the outcome of a previous finding. The term does not necessarily imply a defined level of certainty regarding the prediction of a particular status or outcome.

As used herein, "administering" means that a compound or formulation thereof of the present invention, such as a non-benzenoid aromatic compound, is provided to a patient or subject, for example in a therapeutically effective amount. "Co-administration" refers to administering two or more compounds at some time during a biomedical procedure. Co-administration refers to administration of two or more compounds at the same time, or before or after each other during the same biomedical procedure. Co-administration includes phototherapy procedures wherein a non-benzenoid aromatic compound is administered prior to excitation of a phototherapeutic agent, during excitation of the photherapeutic agent and/or after excitation of a phototherapeutic agent. Co-administration can include multiple administrations during the same biomedical procedure.

Alkyl groups include straight-chain, branched and cyclic (e.g., cycloalkyl) alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group linked to oxygen and can be represented by the formula R—O. Examples of alkoxy groups include, but are not limited to, methoxy, ethoxy, propoxy, butoxy and heptoxy. Alkoxy groups include substituted alkoxy groups wherein the alkyl portion of the groups is substituted as provided herein in connection with the description of alkyl groups. As used herein MeO— refers to $CH_3O$—.

Alkenyl groups include straight-chain, branched and cyclic (e.g., cycloalkenyl) alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

Aryl groups include groups having one or more 5- or 6- or 7-member aromatic or heteroaromatic rings. Heteroaryl groups are aryl groups having one or more heteroatoms (N, O or S) in the ring. Aryl groups can contain one or more fused aromatic rings or a combination of one or more aromatic or heteroaromatic rings and one or more nonaromatic rings that may be fused or linked via covalent bonds. Heterocyclic aromatic rings can include one or more N, O, or S atoms in the ring. Heterocyclic aromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic radical, including monovalent, divalent and polyvalent radicals, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents. Aryl groups include the following compounds and compounds including the following compounds:

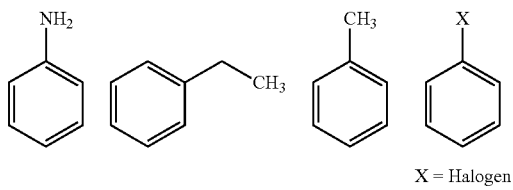

X = Halogen

-continued

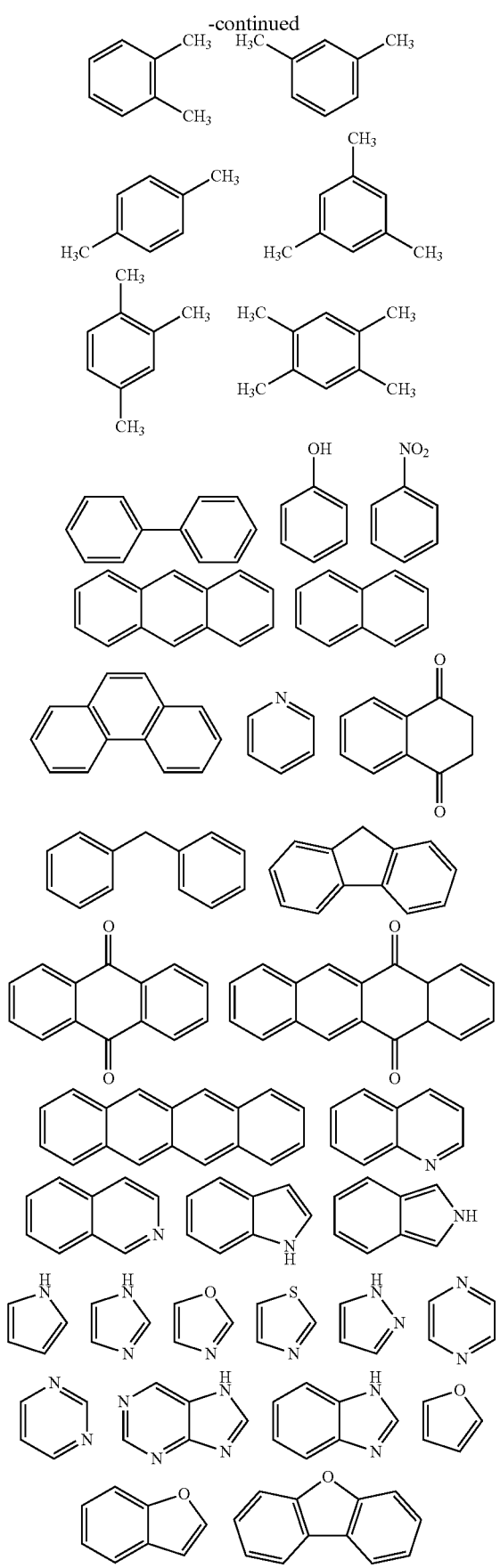
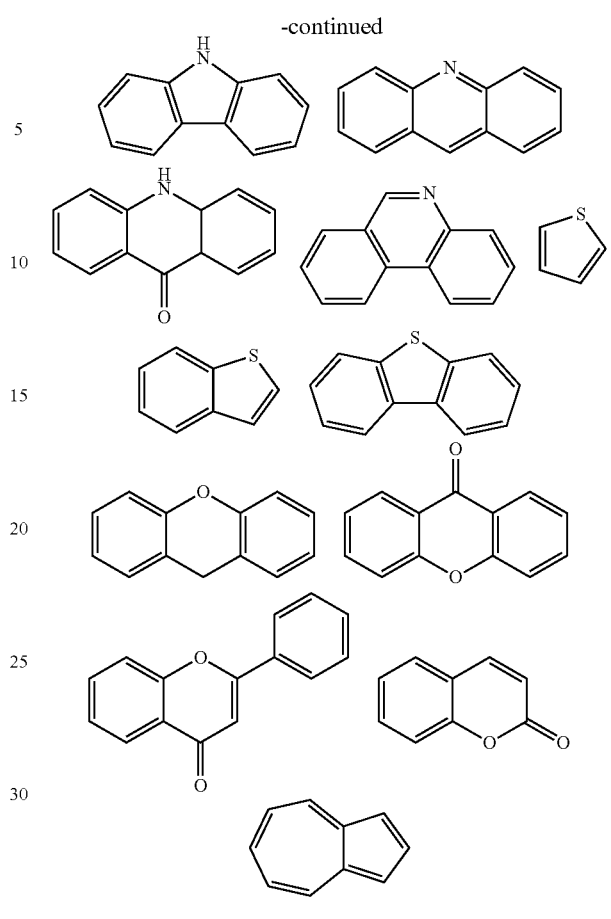

Arylalkyl groups or alkylaryl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl, and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:

—COOR where R is a hydrogen or an alkyl group or an aryl group and more specifically where R is methyl, ethyl, propyl, butyl, or phenyl groups all of which are optionally substituted;

—COR where R is a hydrogen, or an alkyl group or an aryl group and more specifically where R is methyl, ethyl, propyl, butyl, or phenyl groups all of which groups are optionally substituted; —CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl group;

—SO$_2$N(R)$_2$ where R is a hydrogen, an alkyl group, or an aryl group and R and R can form a ring;

—OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups. As used herein, the term "polyhydroxyalkyl" refers to an alkyl group having more than one hydroxy substitution.

As used herein, the term "alkylene" refers to a divalent radical derived from an alkyl group as defined herein. Alkylene groups in some embodiments function as bridging and/or spacer groups in the present compositions. Compounds of the invention include substituted and unsubstituted C1-C20 alkylene, C1-C10 alkylene and C1-C5 alkylene groups.

As used herein, the term "arylene" refers to a divalent radical derived from an aryl group as defined herein. Arylene groups in some embodiments function as attaching and/or spacer groups in the present compositions. Arylene groups in other embodiments function as dye and/or imaging groups in the present compositions. Compounds of the invention include substituted and unsubstituted C$_1$-C$_{20}$ arylene, C$_1$-C$_{10}$ arylene and C$_1$-C$_5$ arylene groups.

As used herein, the term "cycloalkylene" refers to a divalent radical derived from a cycloalkyl group as defined herein. Cycloalkylene groups in some embodiments function as bridging and/or spacer groups in the present compositions. Compounds of the invention include substituted and unsubstituted C1-C20 cycloalkylene, C1-C10 cycloalkylene and C1-C5 cycloalkylene groups.

As used herein, the term "alkenylene" refers to a divalent radical derived from an alkenyl group as defined herein. Alkenylene groups in some embodiments function as bridging and/or spacer groups in the present compositions. Compounds of the invention include substituted and unsubstituted C1-C20 alkenylene, C1-C10 alkenylene and C1-C5 alkenylene groups.

As used herein, the term "cycloalkenylene" refers to a divalent radical derived from a cycloalkenyl group as defined herein. Cycloalkenylene groups in some embodiments function as bridging and/or spacer groups in the present compositions. Compounds of the invention include substituted and unsubstituted C1-C20 cycloalkenylene, C1-C10 cycloalkenylene and C1-C5 cycloalkenylene groups.

As used herein, the term "alkynylene" refers to a divalent radical derived from an alkynyl group as defined herein. Alkynylene groups in some embodiments function as bridging and/or spacer groups in the present compositions. Compounds of the invention include substituted and unsubstituted C1-C20 alkynylene, C1-C10 alkynylene and C1-C5 alkynylene groups.

As used herein, the term "halo" or "halogen" refers to a halogen group such as a fluoro (—F), chloro (—Cl), bromo (—Br) or iodo (—I).

As is customary and well known in the art, hydrogen atoms in the formulas shown herein, including formulae (FX1)-(FX18) are not always explicitly shown. The structures provided herein, for example in the context of the description of formulas (FX1)-(FX18), are intended to convey to one of reasonable skill in the art the chemical composition of compounds of the methods and compositions of the invention, and as will be understood by one of skill in the art, the structures provided do not indicate the specific bond angles between atoms of these compounds.

As used herein, the term "echogenic agent" is used as conventional in the art and is generally a compound used in connection with sonographic imaging. An echogenic agent can, in some embodiments, be used to enhance the sonographic signal, providing targeting for the imaging, or perform other functions, as will be recognized by one of ordinary skill in the art. As used herein, the term "glycomimetic" is used as conventional in the art and refers to a compound that mimics the function of a bioactive carbohydrate.

It should be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

In certain embodiments, the invention encompasses administering optical agents useful in the invention to a patient or subject. A "patient" or "subject", used equivalently herein, refers to an animal. In particular, an animal refers to a mammal, preferably a human. The subject may either: (1) have a condition diagnosable, preventable and/or treatable by administration of an optical agent of the invention; or (2) is susceptible to a condition that is diagnosable, preventable and/or treatable by administering an optical agent of this invention. The compounds of the invention function as optical agents, in some embodiments.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The compounds of this invention may contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

The invention is further detailed in the following Examples, which are offered by way of illustration and are not intended to limit the scope of the invention in any manner.

Example 1: Formulations of Non-Benzenoid Aromatic Compounds

In an embodiment, the invention provides a pharmaceutical formulation comprising a composition of the invention, such as a compound of any one of formulae (FX1)-(FX17). In an embodiment, the invention provides a method of synthesizing a composition of the invention or a pharmaceutical formulation thereof, such as a compound of any one of formulae (FX1)-(FX17). In an embodiment, the invention provides a pharmaceutical formulation comprising a composition of the invention, such as a compound of formula (FX18). In an embodiment, the invention provides a method of synthesizing a composition of the invention or a pharmaceutical formulation thereof, such as a compound of formula (FX18). In an embodiment, a pharmaceutical formulation comprises one or more excipients, carriers, diluents, and/or other components as would be understood in the art. Preferably, the components meet the standards of the National Formulary ("NF"), United States Pharmacopoeia ("USP"; United States Pharmacopeia Convention Inc., Rockville, Md.), or Handbook of Pharmaceutical Manufacturing Formulations (Sarfaraz K. Niazi, all volumes, ISBN: 9780849317521, ISBN 10: 0849317525; CRC Press, 2004). See, e.g., United States Pharmacopeia and National Formulary (USP 30-NF 25), Rockville, Md.: United States Pharmacopeial Convention; 2007; and 2008, and each of any earlier editions; The Handbook of Pharmaceutical Excipients, published jointly by the American Pharmacists Association and the Pharmaceutical Press (Pharmaceutical Press (2005) (ISBN-10: 0853696187, ISBN-13: 978-0853696186); Merck Index, Merck & Co., Rahway, N.J.; and Gilman et al., (eds) (1996); Goodman and Gilman's: The Pharmacological Bases of Therapeutics, 8th Ed., Pergamon Press. In embodiments, the formulation base of the formulations of the invention comprises physiologically acceptable excipients, namely, at least one binder and optionally other physiologically acceptable excipients. Physiologically acceptable excipients are those known to be usable in the pharmaceutical technology sectors and adjacent areas, particularly, those listed in relevant pharmacopeias (e.g. DAB, Ph. Eur., BP, NF, USP), as well as other excipients whose properties do not impair a physiological use.

In an embodiment, an effective amount of a composition of the invention is a therapeutically effective amount. In an embodiment, an effective amount of a composition of the invention is a diagnostically effective amount. In an embodiment, an active ingredient or other component is included in a therapeutically acceptable amount. In an embodiment, an active ingredient or other component is included in a diagnostically acceptable amount.

Variations on compositions including salts and ester forms of compounds: Compounds of this invention and compounds useful in the methods of this invention include those of the compounds and formula(s) described herein and pharmaceutically-acceptable salts and esters of those compounds. In embodiments, salts include any salts derived from the acids of the formulas herein which acceptable for use in human or veterinary applications. In embodiments, the term "esters" refers to hydrolyzable esters of compounds of the names and structural formulas herein. In embodiments, salts and esters of the compounds of the formulas herein can include those which have the same or better therapeutic, diagnostic, or pharmaceutical (human or veterinary) general properties as the compounds of the formulas herein. In an embodiment, a composition of the invention is a compound or salt or ester thereof suitable for pharmaceutical formulations.

In an embodiment, the invention provides a method for treating a medical condition comprising administering to a subject (e.g. patient) in need thereof, a therapeutically effective amount of a composition of the invention, such as a compound of any one of formulae (FX1)-(FX17). In an embodiment, the invention provides a method for treating a medical condition comprising administering to a subject (e.g. patient) in need thereof, a therapeutically effective amount of a composition of the invention, such as a compound of formula (FX18). In an embodiment, the medical condition is cancer, or various other diseases, injuries, and disorders, including cardiovascular disorders such as atherosclerosis and vascular restenosis, inflammatory diseases, ophthalmic diseases and dermatological diseases.

In an embodiment, the invention provides a medicament which comprises a therapeutically effective amount of one or more compositions of the invention, such as a compound of any one of formulae (FX1)-(FX17). In an embodiment, the invention provides a medicament which comprises a therapeutically effective amount of one or more compositions of the invention, such as a compound of formula (FX18). In an embodiment, the invention provides a medicament which comprises a therapeutically or diagnostically effective amount of one or more compositions of the invention. In an embodiment, the invention provides a method for making a medicament for treatment of a condition described herein. In an embodiment, the invention provides a method for making a medicament for diagnosis or aiding in the diagnosis of a condition described herein. In an embodiment, the invention provides the use of one or more compositions set forth herein for the making of a medicament. In an embodiment, the invention provides one or more compositions set forth herein for use as a medicament. In an embodiment, the invention provides one or more compositions set forth herein for use in therapy.

Compounds of the invention can have prodrug forms. Prodrugs of the compounds of the invention are useful in embodiments including compositions and methods. Any compound that will be converted in vivo to provide a biologically, pharmaceutically, diagnostically, or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). A prodrug, such as a pharmaceutically acceptable prodrug can represent prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of a compound described herein, for example, by hydrolysis in blood or by other cell, tissue, organ, or system processes. Further discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds set forth herein.

In an embodiment, a composition of the invention is isolated or purified. In an embodiment, an isolated or purified compound may be at least partially isolated or purified as would be understood in the art. In an embodiment, the composition of the invention has a chemical purity of 95%, optionally for some applications 99%, optionally for some applications 99.9%, optionally for some applications 99.99%, and optionally for some applications 99.999% pure.

Typically, a compound of the present invention, or pharmaceutically acceptable salt thereof, is administered to a subject in a diagnostically or therapeutically effective amount. One skilled in the art generally can determine an appropriate dosage. Factors affecting a particular dosage regimen (including the amount of compound delivered, frequency of administration, and whether administration is continuous or intermittent) include, for example, the type, age, weight, sex, diet, and condition of the subject; the type of pathological condition and its severity; and the nature of the desired effect. Pharmacological considerations include non-benzenoid compound activity, efficacy, pharmacokinetic, and toxicology profiles of the particular non-benzenoid compound used; the route of administration and whether a drug delivery system is utilized; and whether the non-benzenoid compound is administered as part of a combination therapy (e.g., whether the agent is administered in combination with one or more active compounds, other agents, radiation, and the like).

Compositions for oral administration may be, for example, prepared in a manner such that a single dose in one or more oral preparations contains at least about 20 mg of the non-benzenoid compound per square meter of subject body surface area, or at least about 50, 100, 150, 200, 300, 400, or 500 mg of the non-benzenoid compound per square meter of subject body surface area (the average body surface area for a human is, for example, 1.8 square meters). In particular, a single dose of a composition for oral administration can contain from about 20 to about 600 mg, and in certain aspects from about 20 to about 400 mg, in another aspect from about 20 to about 300 mg, and in yet another aspect from about 20 to about 200 mg of the non-benzenoid compound per square meter of subject body surface area. Compositions for parenteral administration can be prepared in a manner such that a single dose contains at least about 20 mg of the non-benzenoid compound per square meter of subject body surface area, or at least about 40, 50, 100, 150, 200, 300, 400, or 500 mg of the non-benzenoid compound per square meter of subject body surface area. In particular, a single dose in one or more parenteral preparations contains from about 20 to about 500 mg, and in certain aspects from about 20 to about 400, and in another aspect from about 20 to about 400 mg, and in yet another aspect from about 20 to about 350 mg of the non-benzenoid compound per square meter of subject body surface area. It should be recognized that these oral and parenteral dosage ranges represent generally preferred dosage ranges, and are not intended to limit the invention. The dosage regimen actually employed can vary widely, and, therefore, can deviate from the generally preferred dosage regimen. It is contemplated that one skilled in the art will tailor these ranges to the individual subject.

As indicated above, it is contemplated that the compounds and pharmaceutically acceptable salts of the present invention may be used as part of a combination. The term "combination" means the administration of two or more compounds directed to the target condition. The treatments of the combination generally may be co-administered in a simultaneous manner. Two compounds can be co-administered as, for example: (a) a single formulation (e.g., a single capsule) having a fixed ratio of active ingredients; or (b) multiple, separate formulations (e.g., multiple capsules) for each compound. The treatments of the combination may alternatively (or additionally) be administered at different times.

It is further contemplated that the non-benzenoid compounds and salts of this invention can be used in the form of a kit that is suitable for use in performing the methods described herein, packaged in a container. The kit can contain the non-benzenoid compound or compounds and, optionally, appropriate diluents, devices or device components suitable for administration and instructions for use in accordance with the methods of the present invention. The devices can include parenteral injection devices, such as syringes or transdermal patch or the like. Device components can include cartridges for use in injection devices and the like. In one aspect, the kit includes a first dosage form including a non-benzenoid compound or salt of this invention and a second dosage form including another active ingredient in quantities sufficient to carry out the methods of the present invention. The first dosage form and the second dosage form together can include a therapeutically effective amount of the compounds for treating the targeted condition(s).

This invention also is directed, in part, to pharmaceutical compositions including a therapeutically effective amount of a compound or salt of this invention, as well as processes for making such compositions. Such compositions generally include one or more pharmaceutically acceptable carriers (e.g., excipients, vehicles, auxiliaries, adjuvants, diluents) and may include other active ingredients. Formulation of these compositions may be achieved by various methods known in the art. A general discussion of these methods may be found in, for example, Hoover, John E., Remington's Pharmaceutical Sciences (Mack Publishing Co., Easton, Pa.: 1975). See also, Lachman, L., eds., Pharmaceutical Dosage Forms (Marcel Decker, New York, N.Y., 1980).

The preferred composition depends on the route of administration. Any route of administration may be used as long as the target of the compound or pharmaceutically acceptable salt is available via that route. Suitable routes of administration include, for example, oral, parenteral, inhalation, rectal, nasal, topical (e.g., transdermal and intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration.

Pharmaceutically acceptable carriers that may be used in conjunction with the compounds of the invention are well known to those of ordinary skill in the art. Carriers can be selected based on a number of factors including, for example, the particular non-benzenoid compound(s) or pharmaceutically acceptable salt(s) used; the compound's concentration, stability, and intended bioavailability; the condition being treated; the subject's age, size, and general condition; the route of administration; etc. A general discussion related to carriers may be found in, for example, J. G. Nairn, Remington's Pharmaceutical Science, pp. 1492-1517 (A. Gennaro, ed., Mack Publishing Co., Easton, Pa. (1985)).

Solid dosage forms for oral administration include, for example, capsules, tablets, gelcaps, pills, dragees, troches, powders, granules, and lozenges. In such solid dosage forms, the compounds or pharmaceutically acceptable salts thereof can be combined with one or more pharmaceutically acceptable carriers. The compounds and pharmaceutically acceptable salts thereof can be mixed with carriers including, but not limited to, lactose, sucrose, starch powder, corn starch, potato starch, magnesium carbonate, microcrystalline cellulose, cellulose esters of alkanoic acids, cellulose alkyl esters, talc, stearic acid, magnesium stearate, magnesium oxide, sodium and calcium salts of phosphoric and sulfuric acids, sodium carbonate, agar, mannitol, sorbitol, sodium saccharin, gelatin, acacia gum, alginic acid, sodium alginate, tragacanth, colloidal silicon dioxide, croscarmellose sodium, polyvinylpyrrolidone, and/or polyvinyl alcohol, and then tableted or encapsulated for convenient administration. Such capsules or tablets can contain a controlled-release formulation, as can be provided in a dispersion of the compound or salt in hydroxypropylmethyl cellulose. In the case of capsules, tablets, and pills, the dosage forms also can include buffering agents, such as sodium citrate, or magnesium or calcium carbonate or bicarbonate. Tablets and pills additionally can, for example, include a coating (e.g., an enteric coating) to delay disintegration and absorption. The concentration of the non-benzenoid compound in a solid oral dosage form can be from about 5 to about 50%, and in certain aspects from about 8 to about 40%, and in another aspect from about 10 to about 30% by weight based on the total weight of the composition.

Liquid dosage forms of the compounds of the present invention for oral administration include, for example, pharmaceutically acceptable emulsions, solutions, suspensions, syrups, and elixirs containing inert diluents commonly used in the art (e.g., water). Such compositions also can include adjuvants, such as wetting, emulsifying, suspending, flavoring (e.g., sweetening), and/or perfuming agents. The concentration of the non-benzenoid compound in the liquid dosage form can be from about 0.01 to about 5 mg, and in certain aspects from about 0.01 to about 1 mg, and in another aspect from about 0.01 to about 0.5 mg per ml of the composition. Low concentrations of the compounds of the present invention in liquid dosage form can be prepared in the case that the non-benzenoid compound is more soluble at low concentrations. Techniques for making oral dosage forms useful in the present invention are generally described in, for example, Modern Pharmaceutics, Chapters 9 and 10 (Banker & Rhodes, Editors (1979)). See also, Lieberman et al., Pharmaceutical Dosage Forms: Tablets (1981). See also, Ansel, Introduction to Pharmaceutical Dosage Forms (2nd Edition (1976)).

In some aspects of the present invention, tablets or powders for oral administration can be prepared by dissolving the non-benzenoid compound in a pharmaceutically acceptable solvent capable of dissolving the compound to form a solution and then evaporating when the solution is dried under vacuum. A carrier can also be added to the solution before drying. The resulting solution can be dried under vacuum to form a glass. The glass can then mix with a binder to form a powder. This powder may be mixed with fillers or other conventional tableting agents, and then processed to form a tablet. Alternatively, the powder may be added to a liquid carrier to form a solution, emulsion, suspension, or the like.

In some aspects, solutions for oral administration are prepared by dissolving the non-benzenoid compound in a pharmaceutically acceptable solvent capable of dissolving the compound to form a solution. An appropriate volume of a carrier is added to the solution while stirring to form a pharmaceutically acceptable solution for oral administration.

"Parenteral administration" includes subcutaneous injections, intravenous injections, intraarterial injections, intraorbital injections, intracapsular injections, intraspinal injections, intraperitoneal injections, intramuscular injections, intrasternal injections, and infusion. Dosage forms suitable for parenteral administration include solutions, suspensions, dispersions, emulsions, and any other dosage form that can be administered parenterally.

Injectable preparations (e.g., sterile injectable aqueous or oleaginous suspensions) can be formulated according to the known art using suitable dispersing, wetting agents, and/or suspending agents. Acceptable vehicles for parenteral use include both aqueous and nonaqueous pharmaceutically-acceptable solvents. Suitable pharmaceutically acceptable aqueous solvents include, for example, water, saline solutions, dextrose solutions (e.g., such as DW5), electrolyte solutions, etc.

Suitable pharmaceutically-acceptable nonaqueous solvents include, but are not limited to, the following (as well as mixtures thereof): alcohols (these include, for example, σ-glycerol formal, β-glycerol formal, 1,3-butyleneglycol, aliphatic or aromatic alcohols having from 2 to about 30 carbons (e.g., methanol, ethanol, propanol, isopropanol, butanol, t-butanol, hexanol, octanol, amylene hydrate, benzyl alcohol, glycerin (glycerol), glycol, hexylene, glycol, tetrahydrofuranyl alcohol, cetyl alcohol, and stearyl alcohol), fatty acid esters of fatty alcohols (e.g., polyalkylene glycols, such as polypropylene glycol and polyethylene glycol), sorbitan, sucrose, and cholesterol); amides (these include, for example, dimethylacetamide (DMA), benzyl benzoate DMA, dimethylformamide, N-hydroxyethyO-lact-amide, N, N-dimethylacetamide-amides, 2-pyrrolidinone, 1-methyl-2-pyrrolidinone, and polyvinyl pyrrolidone); esters (these include, for example, acetate esters (e.g., monoacetin, diacetin, and triacetin), aliphatic and aromatic esters (e.g., ethyl caprylate or octanoate, alkyl oleate, benzyl benzoate, or benzyl acetate), dimethylsulfoxide (DMSO), esters of glycerin (e.g., mono, di, and tri-glyceryl citrates and tartrates), ethyl benzoate, ethyl acetate, ethyl carbonate, ethyl lactate, ethyl oleate, fatty acid esters of sorbitan, glyceryl monostearate, glyceride esters (e.g., mono, di, or tri-glycerides), fatty acid esters (e.g., isopropyl myristrate), fatty acid derived PEG esters (e.g., PEG-hydroxyoleate and PEG-hydroxystearate), N-methyl pyrrolidinone, pluronic 60, polyoxyethylene sorbitol oleic polyesters (e.g., poly (ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate), polyoxyethylene sorbitan esters (e.g., polyoxyethylene-sorbitan monooleate, polyoxyethylene-sorbitan monopalmitate, polyoxyethylene-sorbitan monolaurate, polyoxyethylene-sorbitan monostearate, and POLYSORBATE 20, 40, 60, and 80 (from ICI Americas, Wilmington, Del.)), polyvinylpyrrolidone, alkyleneoxy modified fatty acid esters (e.g., polyoxyl 40 hydrogenated castor oil and polyoxyethylated castor oils, such as CREMOPHOR EL solution or CREMOPHOR RH 40 solution), saccharide fatty acid esters (i.e., the condensation product of a monosaccharide (e.g., pentoses, such as, ribose, ribulose, arabinose, xylose, lyxose, and xylulose; hexoses, such as glucose, fructose, galactose, mannose, and sorbose; trioses; tetroses; heptoses; and octoses), disaccharide (e.g., sucrose, maltose, lactose, and trehalose), oligosaccharide, or a mixture thereof with one or more $C_4$-$C_{22}$ fatty acids (e.g., saturated fatty acids, such as caprylic acid, capric acid, lauric acid, myristic acid, palmitic acid, and stearic acid; and unsaturated fatty acids, such as palmitoleic acid, oleic acid, elaidic acid, erucic acid, and linoleic acid), and steroidal esters); ethers (these are typically alkyl, aryl, and cyclic ethers having from 2 to about 30 carbons. Examples include diethyl ether, tetrahydrofuran, dimethyl isosorbide, diethylene glycol monoethyl ether), and glycofurol (tetrahydrofurfuranyl alcohol polyethylene glycol ether); ketones (these typically have from about 3 to about 30 carbons. Examples include acetone, methyl ethyl ketone, methyl isobutyl ketone); hydrocarbons (these are typically aliphatic, cycloaliphatic, and aromatic hydrocarbons having from about 4 to about 30 carbons). Examples include benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO); and tetramethylene sulfoxide; oils (these include oils of mineral, vegetable, animal, essential, or synthetic origin). These include mineral oils, such as aliphatic and wax-based hydrocarbons, aromatic hydrocarbons, mixed aliphatic and aromatic based hydrocarbons, and refined paraffin oil; vegetable oils, such as linseed, tung, safflower, soybean, castor, cottonseed, groundnut, rapeseed, coconut, palm, olive, corn, corn germ, sesame, persic, and peanut oil; glycerides, such as mono-, di-, and triglycerides; animal oils, such as fish, marine, sperm, cod-liver, haliver, squaiene, squalane, and shark liver oil; oleic oils; and polyoxyethylated castor oil); alkyl, alkenyl, or aryl halides (these include alkyl or aryl halides having from 1 to about 30 carbons and one or more halogen substituents. Examples include methylene chloride); monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (SOLUTOL HS-15, from BASF, Ludwigshafen, Germany); polyoxyethylene glycerol; sodium laurate; sodium oleate; and sorbitan monooleate. Other pharmaceutically acceptable solvents for use in the invention are well known to those of ordinary skill in the art. General discussion relating to such solvents may be found in, for example, The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics 3d ed., (G. Banker et. al., eds., Marcel Dekker, Inc., New York, N.Y. (1995)), The Pharmacological Basis of Therapeutics, (Goodman & Gilman, McGraw Hill Publishing), Pharmaceutical Dosage Forms, (H. Lieberman et. al., eds., Marcel Dekker, Inc., New York, N.Y. (1980)), Remington's Pharmaceutical Sciences, 19th ed., (A. Gennaro, ed., Mack Publishing, Easton, Pa., (1995)), The United States Pharmacopeia 24, The National Formulary 19, (National Publishing, Philadelphia, Pa. (2000)); Spiegel, A. J., et al., "Use of Nonaqueous Solvents in Parenteral Products," J. Pharma. Sciences, Vol. 52, No. 10, pp. 917-927 (1963).

Solvents useful in the present invention include, but are not limited to, those known to stabilize the non-benzenoid compounds or pharmaceutically acceptable salts thereof. These typically include, for example, oils rich in triglycerides, such as safflower oil, soybean oil, and mixtures thereof; and alkyleneoxy-modified fatty acid esters, such as polyoxyl 40 hydrogenated castor oil and polyoxyethylated castor oils (e.g., CREMOPHOR EL solution or CREMOPHOR RH 40 solution). Commercially available triglycerides include INTRALIPID emulsified soybean oil (Kabi-Pharmacia Inc., Stockholm, Sweden), NUTRALIPID emulsion (McGaw, Irvine, Calif.), LIPOSYN II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), LIPOSYN III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels of from about 25 to about 100% (by weight based on the total fatty acid content) (DHASCO from Martek Biosciences Corp., Columbia, Md.; DHA MAGURO from Daito Enterprises, Los Angeles, Calif.; SOYACAL; and TRAVEMULSION). Ethanol in particular is a useful solvent for dissolving a non-benzenoid compound or pharmaceutically acceptable salt thereof to form solutions, emulsions, and the like.

Additional components can be included in the compositions of this invention for various purposes generally known in the pharmaceutical industry. These components tend to impart properties that, for example, enhance retention of the non-benzenoid compound or salt at the site of administration, protect the stability of the composition, control the pH, and facilitate processing of the non-benzenoid compound or salt into pharmaceutical formulations, and the like. Specific examples of such components include cryoprotective agents; agents for preventing reprecipitation of the non-benzenoid compound or salt surface; active, wetting, or emulsifying agents (e.g., lecithin, polysorbate-80, TWEEN 80, pluronic 60, and polyoxyethylene stearate); preservatives (e.g., ethyl-p-hydroxybenzoate); microbial preservatives (e.g., benzyl alcohol, phenol, m-cresol, chlorobutanol, sorbic acid, thimerosal, and paraben); agents for adjusting pH or buffering agents (e.g., acids, bases, sodium acetate, sorbitan monolaurate, etc.); agents for adjusting osmolarity (e.g., glycerin); thickeners (e.g., aluminum monostearate, stearic acid, cetyl alcohol, stearyl alcohol, guar gum, methyl cellulose, hydroxypropylcellulose, tristearin, cetyl wax esters, polyethylene glycol, etc.); colorants; dyes; flow aids; non-volatile silicones (e.g., cyclomethicone); clays (e.g., bentonites); adhesives; bulking agents; flavorings; sweeteners; adsorbents; fillers (e.g., sugars such as lactose, sucrose, mannitol, sorbitol, cellulose, calcium phosphate, etc.); diluents (e.g., water, saline, electrolyte solutions, etc.); binders (e.g., gelatin; gum tragacanth; methyl cellulose; hydroxypropyl methylcellulose; sodium carboxymethyl cellulose; polyvinylpyrrolidone; sugars; polymers; acacia; starches, such as maize starch, wheat starch, rice starch, and potato starch; etc.); disintegrating agents (e.g., starches, such as maize starch, wheat starch, rice starch, potato starch, and carboxymethyl starch; cross-linked polyvinyl pyrrolidone; agar; alginic acid or a salt thereof, such as sodium alginate; croscarmellose sodium; crospovidone; etc); lubricants (e.g., silica; talc; stearic acid and salts thereof, such as magnesium stearate; polyethylene glycol; etc.); coating agents (e.g., concentrated sugar solutions including gum arabic, talc, polyvinyl pyrrolidone, carbopol gel, polyethylene glycol, titanium dioxide, etc.); and antioxidants (e.g., sodium metabisulfite, sodium bisulfite, sodium sulfite, dextrose, phenols, thiophenols, etc.). Techniques and compositions for making parenteral dosage forms are generally known in the art. Formulations for parenteral administration may be prepared from one or more sterile powders and/or granules having a compound or salt of this invention and one or more of the carriers or diluents mentioned for use in the formulations for oral administration. The powder or granule typically is added to an appropriate volume of a solvent (typically while agitating (e.g., stirring) the solvent) that is capable of dissolving the powder or granule. Particular solvents useful in the invention include, for example, water, polyethylene glycol, propylene glycol, ethanol, corn oil, cottonseed oil, peanut oil, sesame oil, benzyl alcohol, sodium chloride, and/or various buffers.

Emulsions for parenteral administration can be prepared by, for example, dissolving a compound or salt of this invention in any pharmaceutically acceptable solvent capable of dissolving the compound to form a solution; and adding an appropriate volume of a carrier, which is an emulsion, to the solution while stirring to form the emulsion. Solutions for parenteral administration can be prepared by, for example, dissolving a compound or salt of this invention in any pharmaceutically acceptable solvent capable of dissolving the compound to form a solution; and adding an appropriate volume of a carrier to the solution while stirring to form the solution.

Suppositories for rectal administration can be prepared by, for example, mixing the drug with a suitable nonirritating excipient that is solid at ordinary temperatures, but liquid at the rectal temperature and will therefore melt in the rectum to release the drug. Suitable excipients include, for example, cocoa butter; synthetic mono-, di-, or triglycerides; fatty acids; and/or polyethylene glycols.

"Topical administration" includes the use of transdermal administration, such as transdermal patches or iontophoresis devices.

If desired, the emulsions or solutions described above for oral or parenteral administration can be packaged in IV bags, vials, or other conventional containers in concentrated form, and then diluted with a pharmaceutically acceptable liquid (e.g., saline) to form an acceptable non-benzenoid concentration before use.

Other adjuvants and modes of administration well known in the pharmaceutical art may also be used. Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $Cl^-$, $Br^-$), sulfate, acetates (e.g., acetate, trifluoroacetate), ascorbates, aspartates, benzoates, citrates, and lactate.

It is understood that this invention is not limited to the particular compounds, methodology, protocols, and reagents described, as these may vary. It is also to be understood that the terminology used herein is for the purpose of describing particular embodiments only, and is not intended to limit the scope of the invention which will be limited only by the appended claims.

Compositions of the invention includes formulations and preparations comprising one or more of the present compounds provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

Example 2: Optical Imaging Using Non-Benzenoid Compounds

In general, molecules absorbing, emitting, or scattering in the visible or NIR region of the electromagnetic spectrum are useful for optical measurement. The high sensitivity associated with fluorescence permits detection without the negative effects of radioactivity or ionizing radiation. Non-benzenoid aromatic compounds of the invention absorb strongly in the red and NIR regions. Furthermore, the electronic properties of these systems are very sensitive to substitution patterns in both rings of the non-benzenoid compound and allows for "tuning" the absorption and emission properties using the information described herein.

In an embodiment of this aspect, the invention provides a method of using an optical agent, for example, in a biomedical procedure for optically imaging or visualizing a target tissue or a class of target tissues. The present methods include tissue selective imaging and visualization methods, such as imaging or visualization of renal tissue. A method of this aspect comprises the step of administering a diagnostically effective amount of a compound to a subject, wherein the compound is a compound having any of formulae (FX1) to (FX17) or a pharmaceutical preparation thereof. A method of this aspect comprises the step of administering a diagnostically effective amount of a compound to a subject, wherein the compound is a compound having formula (FX18) or a pharmaceutical preparation thereof. The present methods are useful for imaging or visualizing colorectal cancer and other cancers, including prostate cancer, gastric cancer, esophageal cancer, uterine-endometrial cancer, pancreatic cancer, breast cancer, cervical cancer, head and neck cancer, hepatic cancer, skin cancer, gallbladder cancer, ling cancer and ovarian cancer.

In methods of this aspect, the compound that has been administered to the subject then is exposed in vivo to electromagnetic radiation and electromagnetic radiation emitted or scattered by the compound is then detected. In some embodiments, fluorescence is excited from the compound (e.g., due to the electromagnetic radiation exposure), optionally via multiphoton excitation processes. In an embodiment particularly useful for imaging and/or visualization, the method of this aspect further comprises: (i) exposing a compound, such as a compound having any one of formula (FX1) to (FX17), administered to the subject to electromagnetic radiation capable of exciting emission from the compound; and (ii) measuring the emission from the compound. In an embodiment particularly useful for imaging and/or visualization, the method of this aspect further comprises: (i) exposing a compound, such as a compound having formula (FX18), administered to the subject to electromagnetic radiation capable of exciting emission from the compound; and (ii) measuring the emission from the compound. In some embodiments, the methods of the present invention use fluorescence excitation via exposure to light having wavelengths selected over the range of 400-1300 nm. For example, optical coherence tomography (OCT) is an optical imaging technique compatible with the present compounds that allows high resolution cross sectional imaging of tissue microstructure. OCT methods use wavelengths of about 1280 nm. Use of electromagnetic radiation having wavelengths selected over the range of 700 nanometers to 1300 nanometers may be useful for some in situ optical imaging methods of the present invention, including biomedical applications for imaging organs, tissue and/or tumors, anatomical visualization, optical guided surgery and endoscopic procedures. Compounds in present methods may function as contrast agents, optical probes and/or tracer elements. The methods of the present invention include in vivo, in vitro and ex vivo imaging and visualization. The present invention provides methods for a range of clinical procedures, including optical imaging methods and/or visualization guided surgery and/or endoscopic diagnostic and therapeutic procedures.

In an exemplary protocol of uses of the compounds of the invention for a biomedical imaging procedure, the non-benzenoid aromatic compound is exposed to visible and/or near infrared light. This exposure of the non-benzenoid aromatic compound to light may occur at any appropriate time but preferably occurs while the non-benzenoid aromatic compound is located in the body. Due to this exposure of the non-benzenoid aromatic compound to the visible and/or infrared light, the non-benzenoid derivative emits spectral energy (e.g., visible and/or near infrared light) that may be detected by appropriate detection equipment. The spectral energy emitted from the non-benzenoid aromatic compound tends to exhibit a wavelength range greater than a wavelength range absorbed by the non-benzenoid aromatic compound. For example, if the non-benzenoid aromatic compound absorbs light of about 700 nm, the non-benzenoid aromatic compound may emit light of about 745 nm.

Detection of the non-benzenoid aromatic compound (or more particularly, light emitted therefrom) may be achieved through optical fluorescence, absorbance or light scattering procedures known in the art. This detection of the emitted spectral energy, or luminescence, may be characterized as a collection of the emitted spectral energy and a generation of electrical signal indicative of the collected spectral energy. For these purposes, the term "luminescence" refers to the emission of light from excited electronic states of atoms or molecules. Luminescence generally refers to light emission, such as photoluminescence, chemiluminescence, and electrochemiluminescence, among others. In photoluminescence, including fluorescence and phosphorescence, the excited electronic state is created by the absorption of electromagnetic radiation. Luminescence detection involves detection of one or more properties of the luminescence or associated luminescence process. These properties may include intensity, excitation and/or emission spectrum, polarization, lifetime, and energy transfer, among others. These properties may also include time-independent (steady-state) and/or time-dependent (time-resolved) properties of the luminescence. Representative luminescence techniques include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), optical-acoustic tomography (OAT) and bioluminescence resonance energy transfer (BRET), multiphoton technology, among others.

By way of example, when a compound is used in the present invention, it is desirable that the wavelength of light supplied to the compound be such that it excites the compound. This excitation causes the molecule to emit part of the absorbed energy at a different wavelength, and the emission can be detected using fluorometric techniques or other techniques as described above. One skilled in the art can readily determine the most appropriate detection technique based on, in part, the specific compound(s) administered, the particular use (e.g., tissue to be detected) and other aspects, including physical limitations of the analysis.

The techniques utilized to detect the spectral energy from the non-benzenoid derivative that is present in the body may be designed to detect only selected wavelengths (or wavelength ranges) and/or may include one or more appropriate spectral filters. Various catheters, endoscopes, ear clips, headbands, surface coils, finger probes, and the like may be utilized to expose the non-benzenoid derivative to light and/or to detect light emitting therefrom. This detection of spectral energy may be accomplished at one or more times intermittently or may be substantially continuous.

Preferably, non-ionizing energy is administered to the subject or sample for detecting or imaging a biological sample to a compound of the invention. For these purposes, the term "non-ionizing energy" generally refers to electromagnetic radiation that does not carry enough energy to completely remove at least one electron from an atom or molecule of the patient's body. For example, in some embodiments, non-ionizing energy may include spectral energy ranging in wavelength from about 400 nm to about 1200 nm. In some embodiments, non-ionizing energy may simply include visible and/or near infrared light.

In one embodiment, the spectral properties of the compounds of the invention may be tuned to desired wavelength ranges for excitation and/or emission. This may be useful, for example, in developing a particular imaging technique using a known excitation source. By way of example, compounds of the formulas (FX1) to (FX18) may be modified to include one or more electron withdrawing substituents (EWG) on one or more positions. Compounds of the formulas (FX1) to (FX18) may be modified to include one or more electron donating substituents (EDG) on one or more positions. One class of electron withdrawing substituents (EWG) is: —CN, —$CO_2R^1$, —$CONR^2R^3$, —$COR^4$, —$NO_2$, —$SOR^5$, —$SO_2R^6$, —$SO_2OR^7$, —$SO_2NR^8R^9$, or —$PO_3R^{10}R^{11}$. One class of electron donating substituents (EDG) is: —$OR^{12}$, —$SR^{13}$, —$NR^{14}R^{15}$, —$NR^{16}COR^{17}$, and —$P(R^{18})$ (where each of $R^1$ to $R^{18}$ are independently hydrogen or $C_1$-$C_6$ alkyl).

In an aspect of the invention, adding an EDG on an odd-numbered substituent of a formula of the invention will lead to a red shift in the wavelength of light emitted from the compound. In an aspect of the invention, adding an EWG on an odd-numbered substituent will lead to a blue shift in the wavelength of light emitted from the compound. In an aspect of the invention, adding an EDG on an even-numbered substituent will lead to a blue shift in the wavelength of light emitted from the compound. In an aspect of the invention, adding an EWG on an even-numbered substituent will lead to a red shift in the wavelength of light emitted from the compound. This information can be used to tailor the spectral properties of the compounds of the invention.

Example 3. Phototherapy Using Phototherapeutic Analogs

Phototherapy, such as photodynamic therapy (PDT), typically employs a combination of a nontoxic photosensitizer (PS) and visible or near infrared light to generate reactive species that kill or otherwise degrade target cells, such as tumors or other lesions. The present invention provides phototherapeutic agents useful for phototherapy.

Compounds of the invention having one or more photoreactive moieties or photoreactive moiety generating groups ("phototherapeutic analogs" or "phototherapeutic agents") are useful for phototherapeutic applications. Photoreactive moieties include, but are not limited to free radicals, carbenes, nitrenes, singlet oxygen, and the like. Examples of Type I photoreactive moieties that can be incorporated into a non-benzenoid aromatic compound for the purpose of synthesizing a phototherapeutic analog include, but are not limited to, azides, azo compounds, diazo compounds, sulfenates, thiadiazoles, peroxides, and the free radical or reactive intermediate formed upon irradiation. Examples of Type II photoreactive moieties that can be incorporated into a non-benzenoid aromatic compound for the purpose of synthesizing a phototherapeutic analog include, but are not limited to, phthalocyanines, porphyrins, extended porphyrins, and benzoporphyrins.

In aspects of this embodiment, compounds of the formulas (FX1) to (FX18) contain one or more functional groups that produce reactive intermediates such as those photoreactive moieties listed above. In aspects of this embodiment, compounds of the formulas (FX1) to (FX18) include one or more azides, azo compounds, diazo compounds, sulfenates, thiadiazoles, or peroxides.

In an embodiment, a separate Type 1 or Type 2 phototherapeutic agent is co-administered to the patient with a non-benzenoid aromatic compound of the invention. The methods described herein fully contemplate this embodiment, in which case the term "phototherapeutic agent" is understood to include a non-benzenoid aromatic compound and a separate Type 1 or Type 2 phototherapeutic agent, which can be administered separately or together.

In some embodiments, for example, the present invention provides methods comprising administration of a phototherapeutic agent. By way of example, the phototherapeutic agent is administered to a patient. Administration provides delivery of the phototherapeutic agent to a target tissue, such as a tumor. The patient may be optionally imaged as described elsewhere to determine the location where the compound is bound within the patient. Once the compound is determined to be bound to the targeted site or sites, the phototherapeutic agent is irradiated with a wavelength and intensity of light (for example electromagnetic radiation having wavelengths selected over the range of 400 nm to 1300 nm) sufficient to cause photofragmentation of the phototherapeutic agent. The photofragmentation typically results in homolytic cleavage of the agent, resulting in the generation of free radical intermediates. The generated free radicals then damage diseased tissues or cells of the targeted site(s) to which the phototherapeutic agent had bound, thereby therapeutically treating the condition of the patient.

In an embodiment, the invention provides a method for a phototherapeutic procedure, the method comprising: (i) administering to a patient an effective amount of a phototherapeutic agent having the formula

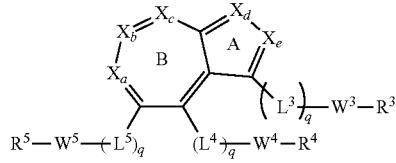

(FX1)

wherein:
$X_a$ is N or —C-$(L^6)_q$—$W^6$—$R^6$;
$X_b$ is N or —C-$(L^7)_q$—$W^7$—$R^7$;
$X_c$ is N or —C-$(L^8)_q$—$W^8$—$R^8$;
$X_d$ is N or —C-$(L^1)_q$—$W^1$—$R^1$;
$X_e$ is N or —C-$(L^2)_q$—$W^2$—$R^2$;
each of $L^1$ to $L^8$ is independently $C_1$-$C_{10}$ alkylene, $C_3$-$C_{10}$ cycloalkylene, $C_2$-$C_{10}$ alkenylene, $C_3$-$C_{10}$ cycloalkenylene, $C_2$-$C_{10}$ alkynylene, ethenylene, ethynylene, phenylene, 1-aza-2,5-dioxocyclopentylene, —$(CH_2CH_2O)_m$—, —$(CHOH)_m$—, or 1,4-diazacyclohexylene;
each m is independently an integer selected from the range of 1 to 100;
each q is independently 0 or 1;
each of $W^1$ to $W^8$ is independently a single bond, —$(CH_2)_n$—, —$O(CH_2)_n$—, —$(CH_2)_nO$—, —$(HCCH)_n$—, —O—, —S—, —SO—, —$SO_2$—, —$SO_3^-$—, —$OSO_2$—, —$NR^9$—, —CO—, —COO—, —OCO—, —OCOO—, —$CONR^{10}$—, —$NR^{11}CO$—, —$OCONR^{12}$—, —$NR^{13}COO$—, —$NR^{14}CONR^{15}$—, —$NR^{16}CSNR^{17}$—, —$O(CH_2)_n$—, —$S(CH_2)_n$—, —$NR^{18}(CH_2)_n$—, —CO$(CH_2)_n$—, —COO$(CH_2)_n$—, —OCO$(CH_2)_n$—, —OCOO$(CH_2)_n$—, —$CONR^{19}(CH_2)_n$—, —$CONR^{20}(CH_2)_n$$(OCH_2CH_2)_u$—, —$NR^{21}CO(CH_2)_n$—, —$OCONR^{22}$$(CH_2)_n$—, —$NR^{23}COO(CH_2)_n$—, —$NR^{24}CONR^{25}$$(CH_2)_n$—, —$NR^{26}CSNR^{27}(CH_2)_n$—, —$O(CH_2)_nNR^{28}CO$ $(CH_2)_n$—, —CO$(CH_2)_n(CH_2OCH_2)_n(CH_2)_nNR^{29}$$(CH_2)_n$NR$^{30}$CO—, —$NR^{69}SR^{70}$—, or —CO$(CH_2)_nNR^{31}CO$—;
each n is independently selected from the range of 1 to 10;
each of $R^9$ to $R^{31}$ and each of $R^{69}$ to $R^{70}$ is independently hydrogen, $C_1$-$C_{20}$ alkyl, or $C_5$-$C_{30}$ aryl;
each of $R^1$ to $R^8$ is independently hydrogen, $C_1$-$C_{20}$ alkyl, $C_5$-$C_{30}$ aryl, $C_1$-$C_{20}$ acyl, $C_2$-$C_{20}$ alkenyl, $C_2$-$C_{20}$ alkynyl, $C_5$-$C_{20}$ alkylaryl, $C_1$-$C_6$ alkoxycarbonyl, halo, halomethyl, dihalomethyl, trihalomethyl, —CN, —$CO_2R^{32}$, —$CONR^{33}R^{34}$, —$COR^{35}$, —$NO_2$, —$SOR^{36}$, —$OSR^{37}$, —$SO_2R^{38}$, —$SO_2OR^{39}$, —$SO_2NR^{40}R^{41}$, —$PO_3R^{42}R^{43}$, —$OR^{44}$, —$SR^{45}$, —$NR^{46}R^{47}$, —$NR^{48}COR^{49}$, —$CH_2$$(CHOH)_nR^{50}$, —$(CH_2CH_2O)_uR^{51}$, —CH$(R^{52})CO_2H$, —CH$(R^{53})NH_2$, $TG^1$ to $TG^8$, $PS^1$ to $PS^8$, or $FL^1$ to $FL^8$;
each u is independently an integer selected from the range of 1 to 25;
each of $R^{32}$ to $R^{55}$ is independently hydrogen or $C_1$-$C_{10}$ alkyl;
each of $TG^1$ to $TG^8$ is independently an amino acid, a peptide, a protein, a nucleoside, a nucleotide, an enzyme, a carbohydrate, a glycomimetic, an oligomer, a lipid, a polymer, an antibody, an antibody fragment, a mono- or polysaccharide comprising 1 to 50 carbohydrate units, a glycopeptide, a glycoprotein, a peptidomimetic, a drug, a drug mimic, a hormone, a receptor, a metal chelating agent, a radioactive or nonradioactive metal complex, a mono- or polynucleotide comprising 1 to 50 nucleic acid units, a polypeptide comprising 2 to 30 amino acid units, or an echogenic agent;

each of $PS^1$ to $PS^8$ is independently a photosensitizing moiety capable of producing one or more free radicals, nitrenes, carbenes, and/or singlet oxygen, and wherein each of $PS^1$ to $PS^8$ comprises at least one azide, azo, diazo, oxaza, diaza, dithia, thioxa, dioxa, phthalocyanine, rhodamine, or porphyrin group; and each of $FL^1$ to $FL^8$ is independently a fluorescent group corresponding to a naphthoquinone, an anthracene, an anthraquinone, a phenanthrene, a tetracene, a naphthacenedione, a pyridine, a quinoline, an isoquinoline, an indole, an isoindole, a pyrrole, an imidiazole, a pyrazole, a pyrazine, a purine, a benzimidazole, a benzofuran, a dibenzofuran, a carbazole, an acridine, an acridone, a phenanthridine, a thiophene, a benzothiophene, a dibenzothiophene, a xanthene, a xanthone, a flavone, a coumarin, a phenoxazine, a phenothiazine, a phenoselenazine, a cyanine, an indocyanine, or an azo compound;

wherein any adjacent $R^1$ to $R^8$ may combine with one or two optional $—CR^{54}R^{55}—$ groups to form $C_5$-$C_6$ cycloalkyl, $C_5$-$C_6$ heterocycloalkyl, $C_6$ aryl or $C_5$-$C_6$ heteroaryl; and (ii) exposing the photosensitizing agent administered to the patient to electromagnetic radiation. In an embodiment of this method, at least one of $R^1$ to $R^8$ is $C_1$-$C_{10}$ alkyl, $—OR^{44}$, $—SR^{45}$, $—NR^{46}R^{47}$, or $—NR^{48}COR^{49}$; and wherein at least one of $R^1$ to $R^8$ is halo, trihalomethyl, $—CN$, $—CO_2R^{32}$, $—CONR^{33}R^{34}$, $—COR^{35}$, $—NO_2$, $—SOR^{36}$, $—SO_2R^{38}$, $—SO_2NR^{40}R^{41}$, or $C_1$-$C_{10}$ acyl; or wherein at least one of $-(L^1)_q-W^1—R^1$, $-(L^2)_q-W^2—R^2$, $-(L^3)_q-W^3—R^3$, $-(L^4)_q-W^4—R^4$, $-(L^5)_q-W^5—R^5$, $-(L^6)_q-W^6—R^6$, $-(L^7)_q-W^7—R^7$, or $-(L)_q-W^8—R^8$ includes a $—(OCH_2CH_2)_u—$ group.

In an embodiment, the method of this aspect of the invention comprises administering to a patient a compound having any one of formulae (FX1) to (FX17), including all of the specific compositions classes and compounds described in connection with formula (FX1) to (FX17), in combination with any of the methods steps presented herein. In an embodiment, the method of this aspect of the invention comprises administering to a patient a compound having formula (FX18), including all of the specific compositions classes and compounds described in connection with formula (FX18), in combination with any of the methods steps presented herein.

In an embodiment, included is a non-benzenoid compound of any of the formulas described herein including formulae (FX1) to (FX17) wherein the compound is a Type 2 photosensitizer without a photosensitizing group attached. In an embodiment, included is a non-benzenoid compound of any of the formulas described herein including formula (FX18) wherein the compound is a Type 2 photosensitizer without a photosensitizing group attached.

Phototherapy methods of the invention include photodynamic therapy and thermal laser photocoagulation. Methods of the present invention may further comprise a number of additional steps. In an embodiment, for example, the method further comprises delivering a phototherapeutic agent of any one of formulae (FX1) to (FX17) to a target tissue or organ, such as a tumor. In an embodiment, the method further comprises contacting a target tissue or organ with a phototherapeutic agent of any one of formulae (FX1) to (FX17). In an embodiment, the present methods further comprise the step of administering phototherapeutic agent of any one of formulae (FX1) to (FX17) into a bodily fluid of the subject. Phototherapy methods of the invention include photodynamic therapy and thermal laser photocoagulation. Methods of the present invention may further comprise a number of additional steps. In an embodiment, for example, the method further comprises delivering a phototherapeutic agent of formula (FX18) to a target tissue or organ, such as a tumor. In an embodiment, the method further comprises contacting a target tissue or organ with a phototherapeutic agent of formula (FX18). In an embodiment, the present methods further comprise the step of administering phototherapeutic agent of formula (FX18) into a bodily fluid of the subject. Phototherapeutic agents may be introduced into the patient by any suitable method, including intravenous, intraperitoneal or subcutaneous injection or infusion, oral administration, transdermal absorption through the skin, or by inhalation. In an embodiment, the method further comprises allowing the phototherapeutic agent to accumulate in a target tissue or organ prior to exposure of the phototherapeutic agent to electromagnetic radiation. In an embodiment, the phototherapeutic agent is administered to the skin, a tumor, surgical site, or a wound site. In an embodiment, for example, the phototherapeutic agent is administered and/or delivered to a blood vessel, lung, heart, throat, ear, rectum, bladder, stomach, intestines, esophagus, liver, brain, prostrate, breast or pancreas of the subject.

In an embodiment, a therapeutically effective amount of the phototherapeutic agent is provided to the subject. For example, parenteral administration advantageously contains a sterile aqueous solution or suspension of the phototherapeutic agent having a concentration of an active agent comprising the compound of any one of formulae (FX1) to (FX18) ranging from about 0.0 µM to about 0.5M. Preferred parenteral formulations have a concentration of an active agent comprising the compound of any one of formulae (FX1) to (FX18) selected over the range of 1 µM to 10 mM. Such solutions also may contain pharmaceutically acceptable buffers, emulsifiers, surfactants, and, optionally, electrolytes such as sodium chloride. The dose of the compound of any one of formulae (FX1) to (FX18) may vary from 0.1 to 500 mg/kg body weight, preferably from 0.5 to 2 mg/kg body weight.

In methods of the present invention, the phototherapeutic agent and any other components can be formulated for enteral (oral or rectal), parenteral, topical, or cutaneous administration. Topical or cutaneous delivery of the phototherapeutic agent may also include aerosols, creams, gels, solutions, emulsions and colloids. The compositions are administered in doses effective to achieve the desired diagnostic or therapeutic objective. Such doses may vary widely depending upon the particular complex employed, the organs or tissues to be examined or treated, the equipment employed in the clinical procedure, the efficacy of the treatment achieved, and the like. These compositions contain an effective amount of the phototherapeutic agent along with conventional pharmaceutical carriers and excipients appropriate for the type of administration contemplated. These compositions may also include stabilizing agents and skin penetration enhancing agents and also may contain pharmaceutically acceptable buffers, emulsifiers, surfactants, and, optionally, electrolytes such as sodium chloride. Formulations for enteral administration may vary widely, as is well known in the art. In general, such formulations are liquids, which include an effective amount of the complexes in aqueous solution or suspension. Such enteral compositions may optionally include buffers, surfactants, emulsifiers, thixotropic agents, and the like. Compounds for oral administration may also contain flavoring agents and other ingredients for enhancing their organoleptic qualities. Formulations for topical delivery may also contain liquid or semisolid excipients to assist in the penetration of the photosensitizer. The compounds may also be delivered in an aerosol spray.

As will be understood by one having skill in the art, the optical conditions for the step of exposing the phototherapeutic agent administered to the patient to electromagnetic radiation will vary considerably with the (i) therapeutic and/or diagnostic objectives, and (ii) the condition of the subject (e.g., height, weight, state of health etc.). In an embodiment, electromagnetic radiation has wavelengths, energy and/or fluence sufficient to achieve a desired therapeutic and/or diagnostic result. In an embodiment, the electromagnetic radiation has wavelengths, energy and/or fluence sufficient to activate the phototherapeutic agent. In a method, the electromagnetic radiation exposed to the phototherapeutic agent has wavelengths selected over the range of 400 nm-1300 nm, preferably for some applications 400 nm-900 nm, preferably for some applications 500 nm to 900 nm. In an embodiment, the electromagnetic radiation exposed to the phototherapeutic agent has wavelengths corresponding to a maximum in the absorption spectrum of the phototherapeutic agent, preferably for some applications a maximum in the visible or NIR regions of the electromagnetic spectrum. Optionally, excitation is achieved using electromagnetic substantially free (e.g., less than about 10% of total radiant energy), of ultraviolet radiation, for example, to minimize exposure of the subject to electromagnetic radiation capable of causing unwanted cell or tissue damage. As will be appreciated by one having skill in the art, the fluence employed during excitation of the phototherapeutic agent can vary depending on the type of tissue, depth of the target, composition of the phototherapeutic agent and the amount on composition of overlying fluid and blood. In some embodiments, the fluence employed is selected over the range of 10 to 500 Joules $cm^{-2}$. The irradiance is typically selected from the range of 50 to 1500 $mWcm^{-2}$, preferably of 50 to 500 $mWcm^{-2}$. Electromagnetic radiation may be provided to the phototherapeutic agent using a range of optical sources and/or surgical instrumentation, including a laser, light emitting diodes, fiber optic device, endoscope, catheter, optical filters, or any combination of these.

Example 4: Biotargeting Using Non-Benzenoid Aromatic Compounds

Compounds of the invention are also useful for targeting biological moieties. Targeted moieties may also undergo subsequent or coincident phototherapeutic applications.

In aspects of this embodiment, compounds of the formulas (FX1) to (FX18) contain one or more biotargeting groups. These ligands are well known in the art. By way of example, the non-benzenoid compound which includes a targeting moiety can be administered to a patient in a diagnostically effective amount to detect the non-benzenoid compound within the patient. After a period of time has lapsed for the compound to bind to the desired target, the whole body or portion thereof is exposed to light of suitable wavelength to excite the non-benzenoid compound. Light emanating from the patient as a result of the absorption and excitation of the non-benzenoid compound is then detected. By evaluating the location and strength of light emanating from the patient, a diagnosis can be made as a result of the targeting properties of the non-benzenoid compound.

In embodiments, compounds of the invention are useful for both oncology and non-oncology applications. Some specific targets are tumors accessible via endoscope. In this application, a compound that targets a peptide associated with such a tumor is administered to the tumor via endoscope or other useful method. Then, the compounds of the invention can be used in phototherapeutic applications or imaging applications. Other specific targets include colon, lung, ovarian, cervical, esophageal, bladder, blood, and stomach cancers; endometriosis, and bacterial infections. Particular targeting groups include ST receptor binding agents, bombesin receptor binding agents, leukemia peptides, and folate receptor binding. Some examples of targeting peptides are described in WO/2008/108941.

In one example, a targeted compound can contain all or part of a steroid hormone or a steroid receptor binding compound, and therefore target steroid hormone sensitive receptors. In this example, the targeted compound is administered, targets and preferably accumulates in the desired site such as breast and/or prostate lesion and is photoactivated for monitoring, imaging, or therapy remotely or at the target site. Similar target binding molecules and uses will be recognized by one skilled in the art. For example, the targeted compound can be a compound that targets and binds to a somatostatin, bombesin, CCK, and/or neurotensin receptor binding molecule, or can be a carcinogenic embryonic antigen-binding compound that binds to a carcinogenic embryonic antigen. These are then photoactivated at, for example, lung cancer cells with CCK receptor binding molecules, colorectal cancer cells with ST receptor and carcinoembryonic antigen (CEA) binding molecules, melanoma cells with dihydroxyindolecarboxylic acid, vascular sites of atherosclerotic plaque with integrin receptor binding molecules, brain lesions with amyloid plaque binding molecules, and the like.

Successful specific targeting of photoactive compounds to tumors using antibodies and peptides for diagnostic imaging of tumors has been described in Achilefu et al., *Novel receptor-targeted fluorescent contrast agents for in vivo imaging of tumors*, Investigative Radiology, 2000, 35, pp. 479-485; Ballou et al., *Tumor labeling in vivo using cyanine conjugated monoclonal antibodies*, Cancer Immunology and Immunotherapy, 1995, 41, pp. 257-263; and Licha et al., *New contrast agent for optical imaging: acid cleavable conjugates of cyanine dyes with biomolecules*, in Biomedical Imaging: Reporters, Dyes and Instrumentation, Proceedings of SPIE, 1999, 3600, pp. 29-35. As such, it is widely accepted that targeted photochemicals are effective in targeting, detecting and treating a wide range of physiological and biological sites.

The optical agents of this example can contain additional functionalities that can be used to attach various types of biomolecules, synthetic polymers, and organized aggregates for selective delivery to various organs or tissues of interest. Examples of synthetic polymers include polyaminoacids, polyols, polyamines, polyacids, oligonucleotides, aborols, dendrimers, and aptamers. The invention includes, but is not limited to, phototherapeutic agents comprising an optical agent—biomolecule conjugate which provides advantages over nonspecific optical agents or the conjugation of optical agents to very large biomolecules. These conjugates provide enhanced localization in, and rapid visualization of, tumors which is beneficial for imaging, monitoring, diagnosis and therapy. The agents are rapidly cleared from blood and non-target tissues so there is less concern for accumulation and for toxicity. A variety of high purity compounds can be easily synthesized for combinatorial screening of new targets, e.g., to identify receptors or targeting agents, and for the ability to affect the pharmacokinetics of the conjugates by minor structural changes.

In some embodiments, a liposome or micelle can be utilized as a carrier or vehicle for the composition. For example, in some embodiments, an optical agent comprises a compound of the invention that can be a part of the lipophilic bilayers or micelle, and the targeting ligand, if present, can be on the external surface of the liposome or micelle. As another example, a targeting ligand can be externally attached to the liposome or micelle after formulation for targeting the liposome or micelle (which contains a phototherapeutic agent/photosensitizer compound of the invention) to the desired tissue, organ, or other site in the body.

In embodiments, compounds of the invention are useful for both oncology and non-oncology applications. Some specific targets are tumors accessible via endoscope. In an application, a compound that targets a protein, polypeptide, oligonucleotide or other biomolecule associated with such a tumor is administered to the tumor via endoscope or other useful method. Then, the compounds of the invention can be used in phototherapeutic applications, monitoring applications, diagnosis applications or imaging applications. Other specific targets include colon, lung, ovarian, cervical, esophageal, bladder, blood, stomach cancers, endometriosis, and bacterial infections.

Targeting Ligands

The estrogen receptor is an example of a steroid receptor to which steroid receptor binding molecules would bind. The following compounds are known to bind to the estrogen receptor: estratriol; 17β-aminoestrogen (AE) derivatives such as prolame and butolame; drugs such as tamoxifen, ICI-164384, raloxifene, and genistein; 17β-estradiol; glucocorticoids; progesterone; estrogens; retinoids; fatty acid derivatives; and phytoestrogens. In addition, commercially available kits can identify compounds specific for binding to the estrogen receptor (e.g., Estrogen Receptor-alpha Competitor Assay Kit, Red; and Estrogen Receptor-beta Competitor Assay Kit, Red (Invitrogen Corp., Carlsbad Calif.).

The glucose receptor is an example of a carbohydrate receptor to which carbohydrate receptor binding molecules would bind. The glucose conjugate N-palmitoyl glucosamine [NPG] is known to bind the glucose receptor (Dufes et al., Pharm. Res. 17:1250, 2000). The glycoprotein hormone receptor is another example of a carbohydrate receptor to which carbohydrate receptor binding molecules would bind. Follicle stimulating hormone (FSH) is known to bind the glycoprotein hormone receptor (Tilly et al., Endocrinology 131: 799, 1992). Other compounds known to bind the carbohydrate receptor, and hence examples of carbohydrate receptor binding molecules, are: polysialic acid, bacterial adhesins (specialized surface proteins that mediate binding of many pathogenic bacteria, such as enterohemorrhagic *E. coli* (EHEC) and *Shigella dysenteriae*, to host cells, which allow these bacteria to colonize host cell surfaces), soluble carbohydrate receptor analogs, artificial glycopolymers and other multivalent glycoconjugates such as an acrylamide copolymer carrying -L-fucopyranoside and 3-sulfo-D-galactopyranoside in clusters, isomeric carbohydrates, synthetic derivatives, neoglycoproteins, neoglycolipids, glycosidases, and glycosyltransferases. Carbohydrate binding proteins can be screened with phage display libraries as known to a person of ordinary skill in the art.

Somatostatin receptor binding molecules include somatostatin and somatostatin receptor analogs, octreotide, glycosylated somatostatin-14 (somatostatin-dextran$^{70}$), seglitide, and peptides P587 and P829 as described in Vallabhajosula et al., J. Nuclear Med., 37:1016, 1996.

Cholecystokinin receptor binding molecules include the endogenous peptides cholecystekinin (CCK)-4, CCK-8, CCK-33, and gastrin; antagonists devazepide and lorglumide; agonists BC264 [Tyr(SO$_3$H)-gNle-mGly-Trp-(NMe)Nle-Asp-Phe-NH$_3$] and desulfated CCK-8; Kinevac (synthetic cholecystekinin, sincalide); and CCK analogues modified at the sulfated tyrosyl at position 27.

Neurotensin receptor binding molecules include neurotensin, neuromedin N, JMV449 (H-Lysψ(CH$_2$NH)-Lys-Pro-Tyr-Ile-Leu), the non-peptide antagonist SR142948A (2-([5-(2,6-dimethoxyphenyl)-1-(4-(N-[3-dimethylaminopropyl]-N-methyl]-N-methylcarbamoyl)-2-isopropylphenyl)-1H-pyrazole-3-carbonyl)amino)adamantine-2-carboxylic acid hydrochloride), and levocobastine. Commercially available neurotensin receptor binding kits can evaluate potential neurotensin receptor binding molecules (e.g., DELFIA Neurotensin Receptor Binding Kit, PerkinElmer (Boston Mass.)).

Bombesin receptor binding molecules include the endogenous ligands gastrin-releasing peptide (GRP), neuromedin B (NMB), and GRP-18-27, and antagonists including JMV-1458 (glycine-extended bombesin (paraphydroxy-phenyl-propionyl-Gln-Trp-Ala-Val-Gly-His-Leu-Met-Gly-OH)), JMV-641, JMV-1799, and JMV-1802, PD165929, 1-naphthoyl-[DAla$^{24}$,DPro$^{26}$,ψ26-27]GRP-20-27, kuwanon H, and kuwanon G. Commercially available bombesin receptor binding kits can evaluate potential bombesin receptor binding molecules (e.g., DELFIA Bombesin Receptor Binding Kit, PerkinElmer (Boston Mass.)).

ST receptor binding molecules include native ST peptide, and SEQ ID NO:2, SEQ ID NO:3, SEQ ID NOS:5-54 and fragments and derivatives thereof from U.S. Pat. No. 5,518,888.

Compounds of the invention can contain all or part of a targeting ligand, receptor or peptide known to bind to a specific target. Methods of attaching the targeting ligand, receptor or peptide to a compound of the invention are described elsewhere herein.

Example 5: Administration and Formulation

Salts and Prodrugs

The invention contemplates pharmaceutically active compounds either chemically synthesized or formed by in vivo biotransformation to compounds set forth herein.

Optical agents of the invention can be formulated with pharmaceutically-acceptable anions and/or cations. Pharmaceutically acceptable salts comprise pharmaceutically-acceptable anions and/or cations. As used herein, the term "pharmaceutically acceptable salt" can refer to acid addition salts or base addition salts of the compounds in the present disclosure. A pharmaceutically acceptable salt is any salt which retains at least a portion of the activity of the parent compound and does not impart significant deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, cilexetil, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalacturonic, propionic, salicylic, stearic, succinic, sulfamic, sulfanlic, sulfonic, sulfuric, tannic, tartaric, teoclic, toluenesulfonic, and the like. Pharmaceutically acceptable salts can be derived from amino acids, including, but not limited to, cysteine. Other pharmaceutically acceptable salts can be found, for example, in Stahl et al., Handbook of Pharmaceutical Salts: Properties, Selection, and Use, Wiley-VCH, Verlag Helvetica Chimica Acta, Zürich, 2002. (ISBN 3-906390-26-8).

Efficacy

Toxicity and therapeutic efficacy of such compounds and bioconjugates can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$. Compounds and bioconjugates that exhibit large therapeutic indices are preferred. While compounds and bioconjugates exhibiting toxic side effects can be used, care should be taken to design a delivery system that targets such compounds and bioconjugates to the site affected by the disease or disorder in order to minimize potential damage to unaffected cells and reduce side effects.

Data obtained from the cell culture assays and animal studies can be used in formulating a range of dosages for use in humans and other mammals. The dosage of such compounds and bioconjugates lies preferably within a range of circulating plasma or other bodily fluid concentrations that include the $ED_{50}$ and provides clinically efficacious results (i.e., reduction in disease symptoms). The dosage can vary within this range depending upon the dosage form employed and the route of administration utilized. For any compound and bioconjugate of the present invention, the therapeutically effective amount can be estimated initially from cell culture assays. A dosage can be formulated in animal models to achieve a circulating plasma concentration range that includes the $ED_{50}$ (the concentration of the test compound that achieves a half-maximal inhibition of symptoms) as determined in cell culture. Such information can be used to more accurately determine useful dosages in humans and other mammals. Compound and bioconjugate levels in plasma can be measured, for example, by high performance liquid chromatography.

An amount of a compound or bioconjugate that can be combined with a pharmaceutically acceptable carrier to produce a single dosage form will vary depending upon the patient treated and the particular mode of administration. It will be appreciated by those skilled in the art that the unit content of a compound/bioconjugate contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage and dosage regime for treating a disease or condition can be selected in accordance with a variety of factors, including the type, age, weight, sex, diet and/or medical condition of the patient, the route of administration, pharmacological considerations such as activity, efficacy, pharmacokinetic and/or toxicology profiles of the particular compound/bioconjugate employed, whether a compound/bioconjugate delivery system is utilized, and/or whether the compound/bioconjugate is administered as a pro-drug or part of a drug combination. Thus, the dosage regime actually employed can vary widely from subject to subject, or disease to disease and different routes of administration can be employed in different clinical settings.

The identified compounds/bioconjugates monitor, treat, inhibit, control and/or prevent, or at least partially arrest or partially prevent, diseases and conditions of interest and can be administered to a subject at therapeutically effective amounts and optionally diagnostically effective amounts. Compositions/formulations of the present invention comprise a therapeutically effective amount (which can optionally include a diagnostically effective amount) of at least one compound or bioconjugate of the present invention. Subjects receiving treatment that includes a compound/bioconjugate of the invention are preferably animals (e.g., mammals, reptiles and/or avians), more preferably humans, horses, cows, dogs, cats, sheep, pigs, and/or chickens, and most preferably humans.

Administration

The diagnostic and therapeutic formulations of this invention can be administered alone, but can be administered with a pharmaceutical carrier selected upon the basis of the chosen route of administration and standard pharmaceutical practice.

Any suitable form of administration can be employed in connection with the diagnostic and therapeutic formulations of the invention. The diagnostic and therapeutic formulations of this invention can be administered intravenously, in oral dosage forms, intraperitoneally, subcutaneously, or intramuscularly, all using dosage forms well known to those of ordinary skill in the pharmaceutical arts.

The present compositions, preparations and formulations can be formulated into diagnostic or therapeutic compositions for enteral, parenteral, topical, aerosol, inhalation, or cutaneous administration. Topical or cutaneous delivery of the compositions, preparations and formulations can also include aerosol formulation, creams, gels, solutions, etc. The present compositions, preparations and formulations are administered in doses effective to achieve the desired diagnostic and/or therapeutic effect. Such doses can vary widely depending upon the particular compositions employed in the composition, the organs or tissues to be examined, the equipment employed in the clinical procedure, the efficacy of the treatment achieved, and the like. These compositions, preparations and formulations contain an effective amount of the composition(s), along with conventional pharmaceutical carriers and excipients appropriate for the type of administration contemplated. These compositions, preparations and formulations can also optionally include stabilizing agents and skin penetration enhancing agents.

(i) Parenteral Administration

Compounds and bioconjugates of the present invention can be formulated for parenteral administration by injection (e.g., by bolus injection or continuous infusion). Formulations for injection can be presented in unit dosage form in ampoules or in multi-dose containers with an optional preservative added. The parenteral preparation can be enclosed in ampoules, disposable syringes or multiple dose vials made of glass, plastic or the like. The formulation can take such forms as suspensions, solutions or emulsions in oily or aqueous vehicles, and can contain formulatory agents such as suspending, stabilizing and/or dispersing agents.

For example, a parenteral preparation can be a sterile injectable solution or suspension in a nontoxic parenterally acceptable diluent or solvent (e.g., as a solution in 1,3-butanediol).

Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid can be used in the parenteral preparation.

Alternatively, compounds and bioconjugates of the present invention can be formulated in powder form for constitution with a suitable vehicle, such as sterile pyrogen-free water, before use. For example, a compound/bioconjugate suitable for parenteral administration can include a sterile isotonic saline solution containing between 0.1 percent and 90 percent weight per volume of the compound/bioconjugate. By way of example, a solution can contain from about 5 percent to about 20 percent, more preferably from about 5 percent to about 17 percent, more preferably from about 8 to about 14 percent, and still more preferably about 10 percent weight per volume of the compound/bioconjugate. The solution or powder preparation can also include a solubilizing agent and a local anesthetic such as lignocaine to ease pain at the site of the injection. Other methods of parenteral delivery of compounds/bioconjugates will be known to the skilled artisan and are within the scope of the invention.

(ii) Oral Administration

For oral administration, a compound/bioconjugate of the invention can be formulated to take the form of tablets or capsules prepared by conventional means with one or more pharmaceutically acceptable carriers (e.g., excipients such as binding agents, fillers, lubricants and disintegrants).

(iii) Controlled-Release Administration

Controlled-release (or sustained-release) preparations can be formulated to extend the activity of a compound/bioconjugate and reduce dosage frequency. Controlled-release preparations can also be used to effect the time of onset of action or other characteristics, such as blood levels of the compound/bioconjugate, and consequently affect the occurrence of side effects.

Controlled-release preparations can be designed to initially release an amount of a compound/bioconjugate that produces the desired therapeutic effect, and gradually and continually release other amounts of the compound/bioconjugate to maintain the level of therapeutic effect over an extended period of time. In order to maintain a near-constant level of a compound/bioconjugate in the body, the compound/bioconjugate can be released from the dosage form at a rate that will replace the amount of compound/bioconjugate being metabolized and/or excreted from the body. The controlled-release of a compound/bioconjugate can be stimulated by various inducers, e.g., change in pH, change in temperature, enzymes, water, and/or other physiological conditions or molecules.

Controlled-release systems can include, for example, an infusion pump which can be used to administer the compound/bioconjugate in a manner similar to that used for delivering insulin or chemotherapy to the body generally, or to specific organs or tumors. Typically, using such a system, the compound/bioconjugate is administered in combination with a biodegradable, biocompatible polymeric implant that releases the compound/bioconjugate over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target (e.g., organ, tissue, or group of cells), thus requiring only a fraction of a systemic dosage.

Compounds/bioconjugates of the invention can be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds/bioconjugates will be known to the skilled artisan and are within the scope of the invention.

(iv) Inhalation Administration

Compounds/bioconjugates of the invention can be administered directly to the lung of a patient/subject by inhalation. For administration by inhalation, a compound/bioconjugate can be conveniently delivered to the lung by a number of different devices. For example, a Metered Dose Inhaler ("MDI") which utilizes canisters that contain a suitable low boiling point propellant, e.g., dichlorodifluoromethane, trichlorofluoromethane, dichlorotetrafluoroethane, carbon dioxide or other suitable gas can be used to deliver a compound/bioconjugate directly to the lung. MDI devices are available from a number of suppliers such as 3M Corporation, Aventis, Boehringer Ingleheim, Forest Laboratories, GlaxoSmithKline, Merck & Co. and Vectura.

Alternatively, a Dry Powder Inhaler (DPI) device can be used to administer a compound/bioconjugate to the lung. DPI devices typically use a mechanism such as a burst of gas to create a cloud of dry powder inside a container, which can then be inhaled by the patient. DPI devices are also well known in the art and can be purchased from a number of vendors which include, for example, GlaxoSmithKline, Nektar Therapeutics, Innovata and Vectura. A popular variation is the multiple dose DPI ("MDDPI") system, which allows for the delivery of more than one therapeutic dose. MDDPI devices are available from companies such as AstraZeneca, GlaxoSmithKline, TEVA, Merck & Co., SkyePharma and Vectura. For example, capsules and cartridges of gelatin for use in an inhaler or insufflator can be formulated containing a powder mix of the compound/bioconjugate and a suitable powder base such as lactose or starch for these systems.

Another type of device that can be used to deliver a compound/bioconjugate to the lung is a liquid spray device supplied, for example, by Aradigm Corporation. Liquid spray systems use extremely small nozzle holes to aerosolize liquid compound/bioconjugate formulations that can then be directly inhaled into the lung. For example, a nebulizer device can be used to deliver a compound/bioconjugate to the lung. Nebulizers create aerosols from liquid compound/bioconjugate formulations by using, for example, ultrasonic energy to form fine particles that can be readily inhaled. Examples of nebulizers include devices supplied by Aventis and Battelle.

In another example, an electrohydrodynamic ("EHD") aerosol device can be used to deliver a compound/bioconjugate to the lung. EHD aerosol devices use electrical energy to aerosolize liquid compound/bioconjugate solutions or suspensions. The electrochemical properties of the compound/bioconjugate formulation are important parameters to optimize when delivering this compound/bioconjugate to the lung with an EHD aerosol device. Such optimization is routinely performed by one of skill in the art. Other methods of intra-pulmonary delivery of compounds/bioconjugates will be known to the skilled artisan and are within the scope of the invention.

Liquid compound/bioconjugate formulations suitable for use with nebulizers and liquid spray devices and EHD aerosol devices will typically include the compound/bioconjugate with a pharmaceutically acceptable carrier. In one exemplary embodiment, the pharmaceutically acceptable carrier is a liquid such as alcohol, water, polyethylene glycol or a perfluorocarbon. Optionally, another material can be added to alter the aerosol properties of the solution or suspension of the compound/bioconjugate. For example, this material can be a liquid such as an alcohol, glycol, polyglycol or a fatty acid. Other methods of formulating liquid compound/bioconjugate solutions or suspensions suitable for use in aerosol devices are known to those of skill in the art.

(v) Depot Administration

A compound/bioconjugate of the invention can be formulated as a depot preparation.

Such long-acting formulations can be administered by implantation (e.g., subcutaneously or intramuscularly) or by intramuscular injection. Accordingly, the compound/bioconjugate can be formulated with suitable polymeric or hydrophobic materials such as an emulsion in an acceptable oil or ion exchange resin, or as sparingly soluble derivatives such as a sparingly soluble salt. Other methods of depot delivery of compounds/bioconjugates will be known to the skilled artisan and are within the scope of the invention.

(vi) Topical Administration

For topical application, a compound/bioconjugate can be combined with a pharmaceutically acceptable carrier so that an effective dosage is delivered, based on the desired activity ranging from an effective dosage, for example, of 1.0 μM to 1.0 mM. In one aspect of the invention, a topical formulation of a compound/bioconjugate can be applied to the skin. The pharmaceutically acceptable carrier can be in the form of, for example, and not by way of limitation, an ointment, cream, gel, paste, foam, aerosol, suppository, pad or gelled stick.

A topical formulation can include a therapeutically effective amount of a compound/bioconjugate in an ophthalmologically acceptable excipient such as buffered saline, mineral oil, vegetable oils such as corn or arachis oil, petroleum jelly, Miglyol 182, alcohol solutions, or liposomes or liposome-like products. Any of these formulations of such compounds/bioconjugates can include preservatives, antioxidants, antibiotics, immunosuppressants, and other biologically or pharmaceutically effective agents that do not exert a significant detrimental effect on the compound/bioconjugate. Other methods of topical delivery of compounds/bioconjugates will be known to the skilled artisan and are within the scope of the invention.

(vii) Rectal Administration

Compounds/bioconjugates of the invention can be formulated in rectal formulations such as suppositories or retention enemas that include conventional suppository bases such as cocoa butter or other glycerides and/or binders and/or carriers such as triglycerides, microcrystalline cellulose, gum tragacanth or gelatin. Rectal formulations can contain a compound/bioconjugate in the range of 0.5% to 10% by weight, for example. Other methods of rectal delivery of compounds/bioconjugates will be known to the skilled artisan and are within the scope of the invention.

(viii) Other Systems of Administration

Various other delivery systems are known in the art and can be used to administer the compounds/bioconjugates of the invention. Moreover, these and other delivery systems can be combined and/or modified to promote optimization of the administration of compounds/bioconjugates of the present invention. Exemplary formulations that include compounds/bioconjugates of the present invention are described elsewhere herein (the compounds/bioconjugates of the present invention are indicated as the active ingredient, but those of skill in the art will recognize that pro-drugs and compound combinations are also meant to be encompassed by this term).

Formulation

In an embodiment, the invention provides the use of one or more compositions set forth herein for the diagnosis of a disease.

In an embodiment, the invention provides a pharmaceutical formulation having an active ingredient comprising a composition of the invention, such as a compound of any one of formulas (FX1)-(FX17). In an embodiment, the invention provides a method of synthesizing a composition of the invention or a pharmaceutical formulation thereof, such as a compound of any one of formulas (FX1)-(FX17). In an embodiment, the invention provides a pharmaceutical formulation having an active ingredient comprising a composition of the invention, such as a compound of any one of formulas (FX18). In an embodiment, the invention provides a method of synthesizing a composition of the invention or a pharmaceutical formulation thereof, such as a compound of any one of formulas (FX18).

This invention also is directed, in part, to pharmaceutical compositions including a therapeutically effective amount of a compound or salt of this invention, as well as processes for making such compositions. Such compositions generally include one or more pharmaceutically acceptable carriers (e.g., excipients, vehicles, auxiliaries, adjuvants, diluents) and can include other active ingredients. Formulation of these compositions can be achieved by various methods known in the art. A general discussion of these methods can be found in, for example, Hoover, John E., Remington's Pharmaceutical Sciences (Mack Publishing Co., Easton, Pa.: 1975). See also, Lachman, L., eds., Pharmaceutical Dosage Forms (Marcel Decker, New York, N.Y., 1980).

The diagnostic and therapeutic formulations of this invention and medicaments of this invention can further comprise one or more pharmaceutically acceptable carriers, excipients, buffers, emulsifiers, surfactants, electrolytes or diluents. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985).

Compositions of the invention include formulations and preparations comprising one or more of the present compounds provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

Compounds and bioconjugates of the present invention can be formulated by known methods for administration to a subject using several routes which include, but are not limited to, parenteral, oral, topical, intradermal, intramuscular, intraperitoneal, intravenous, subcutaneous, intranasal, epidural, and ophthalmic routes. An individual compound/bioconjugate can be administered in combination with one or more additional compounds/bioconjugates of the present invention and/or together with other biologically active or biologically inert agents. Such biologically active or inert agents can be in fluid or mechanical communication with the compound(s)/bioconjugate(s) or attached to the compound(s)/bioconjugate(s) by ionic, covalent, Van der Waals, hydrophobic, hydrophilic or other physical forces. It is preferred that administration is localized in a subject, but administration can also be systemic.

Compounds and bioconjugates of the present invention can be formulated by any conventional manner using one or more pharmaceutically acceptable carriers. Thus, the compound(s)/bioconjugate(s) and their pharmaceutically acceptable salts and solvates can be specifically formulated for administration, e.g., by inhalation or insufflation (either through the mouth or the nose) or oral, buccal, parenteral or rectal administration. The compounds/bioconjugates can take the form of charged, neutral and/or other pharmaceutically acceptable salt forms. Examples of pharmaceutically acceptable carriers include, but are not limited to, those described in REMINGTON'S PHARMACEUTICAL SCIENCES (A. R. Gennaro, Ed.), 20th edition, Williams & Wilkins PA, USA (2000).

Compounds and bioconjugates of the present invention can be formulated in the form of solutions, suspensions, emulsions, tablets, pills, capsules, powders, controlled- or sustained-release formulations and the like. Such formulations will contain a therapeutically effective amount of the compound/bioconjugate, preferably in purified form, together with a suitable amount of carrier so as to provide the form for proper administration to the patient. The formulation should suit the mode of administration.

In some embodiments, a liposome or micelle can be utilized as a carrier or vehicle for the composition. For example, in some embodiments, the compound can be a part of the lipophilic bilayers or micelle, and the targeting ligand, if present, can be on the external surface of the liposome or micelle. As another example, a targeting ligand can be externally attached to the liposome or micelle after formulation for targeting the liposome or micelle (which contains the optical agents) to the desired tissue, organ, or other site in the body.

In one embodiment, the present compounds are formulated as nanoparticles or microparticles. Use of such nanoparticle or microparticle formulations can be beneficial for some applications to enhance delivery, localization, target specificity, administration, etc. of the compound. Potentially useful nanoparticles and microparticles include, but are not limited to, micelles, liposomes, microemulsions, nanoemulsions, vesicles, tubular micelles, cylindrical micelles, bilayers, folded sheets structures, globular aggregates, swollen micelles, inclusion complex, encapsulated droplets, microcapsules, nanocapsules or the like. As will be understood by those having skill in the art, the present compounds can be located inside the nanoparticle or microparticle, within a membrane or wall of the nanoparticle or microparticle, or outside of (but bonded to or otherwise associated with) the nanoparticle or microparticle. The agent formulated in nanoparticles or microparticles can be administered by any of the routes previously described. In a formulation applied topically, the compound is slowly released over time. In an injectable formulation, the liposome, micelle, capsule, etc., circulates in the bloodstream and is delivered to the desired site (e.g., target tissue).

Preparation and loading of nanoparticles and microparticles are well known in the art.

As one example, liposomes can be prepared from dipalmitoyl phosphatidylcholine (DPPC) or egg phosphatidylcholine (PC) because this lipid has a low heat transition. Liposomes are made using standard procedures as known to one skilled in the art (e.g., Braun-Falco et al., (Eds.), Griesbach Conference, Liposome Dermatics, Springer-Verlag, Berlin (1992), pp. 69 81; 91 117 which is expressly incorporated by reference herein). Polycaprolactone, poly(glycolic) acid, poly(lactic) acid, polyanhydride or lipids can be formulated as microspheres. As an illustrative example, the present compounds can be mixed with polyvinyl alcohol (PVA), the mixture then dried and coated with ethylene vinyl acetate, then cooled again with PVA. In a liposome, the present compounds can be within one or both lipid bilayers, in the aqueous between the bilayers, or within the center or core. Liposomes can be modified with other molecules and lipids to form a cationic liposome. Liposomes can also be modified with lipids to render their surface more hydrophilic which increases their circulation time in the bloodstream. The thus-modified liposome has been termed a "stealth" liposome, or a long-lived liposome, as described in U.S. Pat. No. 6,258,378, and in Stealth Liposomes, Lasic and Martin (Eds.) 1995 CRC Press, London, which are expressly incorporated by reference herein. Encapsulation methods include detergent dialysis, freeze drying, film forming, injection, as known to one skilled in the art and disclosed in, for example, U.S. Pat. No. 6,406,713 which is expressly incorporated by reference herein in its entirety. Optionally, the present compositions and methods include a micelle delivery system, for example, involving one or more PEG-based amphiphilic polymers developed for drug delivery including: PEG-poly(ε-caprolactone), PEG-poly(amino acid), PEG-polylactide or PEG-phospholipid constructs; a cross linked poly(acrylic acid) polymer system, a phospholipid-based system and/or block copolymer systems comprising one or more of the following polymer blocks: a poly(lactic acid) polymer block; a poly(propylene glycol) polymer block; a poly(amino acid) polymer block; a poly(ester) polymer block; a poly(ε-caprolactone) polymer block; a poly(ethylene glycol) block, a poly(acrylic acid) block; a polylactide block; a polyester block; a polyamide block; a polyanhydride block; a polyurethane block; a polyimine block; a polyurea block; a polyacetal block; a polysaccharide block; and a polysiloxane block.

Every formulation or combination of components described or exemplified herein can be used to practice the invention, unless otherwise stated.

(i) Binding Agents

Binding agents include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof. Suitable forms of microcrystalline cellulose include, for example, the materials sold as AVICEL-PH-101, AVICEL-PH-103 and AVICEL-PH-105 (available from FMC Corporation, American Viscose Division, Avicel Sales, Marcus Hook, Pa., USA). An exemplary suitable binder is a mixture of microcrystalline cellulose and sodium carboxymethyl cellulose sold as AVICEL RC-581 by FMC Corporation.

(ii) Fillers

Fillers include, but are not limited to, talc, calcium carbonate (e.g., granules or powder), lactose, microcrystalline cellulose, powdered cellulose, dextrates, kaolin, mannitol, silicic acid, sorbitol, starch, pre-gelatinized starch, and mixtures thereof.

(iii) Lubricants

Lubricants include, but are not limited to, calcium stearate, magnesium stearate, mineral oil, electromagnetic radiation mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a syloid silica gel (AEROSIL 200, manufactured by W.R. Grace Co. of Baltimore, Md., USA), a coagulated aerosol of synthetic silica (marketed by Deaussa Co. of Plano, Tex., USA), CAB-O-SIL (a pyrogenic silicon dioxide product sold by Cabot Co. of Boston, Mass., USA), and mixtures thereof.

(iv) Disintegrants

Disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Tablets or capsules can optionally be coated by methods well known in the art. If binders and/or fillers are used with a compound/bioconjugate of the invention, they are typically formulated as about 50 to about 99 weight percent of the compound/bioconjugate. In one aspect, about 0.5 to about 15 weight percent of disintegrant, and particularly about 1 to about 5 weight percent of disintegrant, can be used in combination with the compound. A lubricant can optionally be added, typically in an amount of less than about 1 weight percent of the compound/bioconjugate. Techniques and pharmaceutically acceptable additives for making solid oral dosage forms are described in Marshall, SOLID ORAL DOSAGE FORMS, Modern Pharmaceutics (Banker and Rhodes, Eds.), 7:359-427 (1979). Other formulations are known in the art.

Liquid preparations for oral administration can take the form of solutions, syrups or suspensions. Alternatively, the liquid preparations can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and/or preservatives (e.g., methyl or propyl-p-hydroxybenzoates or sorbic acid). The preparations can also contain buffer salts, flavoring, coloring, perfuming and sweetening agents as appropriate. Preparations for oral administration can also be formulated to achieve controlled release of the compound/bioconjugate. Oral formulations preferably contain 10% to 95% compound/bioconjugate. In addition, a compound/bioconjugate of the present invention can be formulated for buccal administration in the form of tablets or lozenges formulated in a conventional manner. Other methods of oral delivery of compounds/bioconjugates of the invention will be known to the skilled artisan and are within the scope of the invention.

Formulation 1

Hard gelatin capsules are prepared using the following ingredients:

TABLE F1

| Ingredients | (mg/capsule) |
|---|---|
| Active Ingredient | 250.0 |
| Starch | 305.0 |
| Magnesium stearate | 5.0 |

The above ingredients are mixed and filled into hard gelatin capsules in 560 mg quantities.

Formulation 2

A tablet formula is prepared using the following ingredients:

TABLE F2

| Ingredients | (mg/tablet) |
|---|---|
| Active Ingredient | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

Formulation 3

A dry powder inhaler formulation is prepared containing the following components:

TABLE F3

| Ingredients | Weight % |
|---|---|
| Active ingredient | 5 |
| Lactose | 95 |

The active ingredient is mixed with the lactose and the mixture is added to a dry powder inhaling appliance.

Formulation 4

Tablets, each containing 60 mg of active ingredient, are prepared as follows:

TABLE F4

| Ingredients | milligrams |
|---|---|
| Active ingredient | 60.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 150.0 |

The active ingredient, starch and cellulose are passed through a No. 20 mesh U.S. sieve and mixed thoroughly. The solution of polyvinylpyrrolidone is mixed with the resultant powders which are then passed through a 16 mesh U.S. sieve. The granules as produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation 5

Capsules, each containing 80 mg of active ingredient are made as follows:

TABLE F5

| Ingredients | milligrams |
| --- | --- |
| Active ingredient | 80.0 |
| Starch | 109.0 |
| Magnesium stearate | 1.0 |
| Total | 190.0 |

The active ingredient, cellulose, starch, and magnesium stearate are blended, passed through a No. 20 mesh U.S. sieve, and filled into hard gelatin capsules in 190 mg quantities.

Formulation 6

Suppositories, each containing 225 mg of active ingredient, are made as follows:

TABLE F6

| Ingredients | milligrams |
| --- | --- |
| Active Ingredient | 225 |
| Saturated fatty acid glycerides to | 2000 |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of active ingredient per 5.0 ml dose are made as follows:

TABLE F7

| Ingredients | milligrams |
| --- | --- |
| Active ingredient | 50.0 mg |
| Xanthan gum | 4.0 mg |
| Sodium carboxymethyl cellulose | (11%) |
| Microcrystalline cellulose | (89%) 50.0 mg |
| Sucrose | 1.75 g |
| Sodium benzoate | 10.0 mg |
| Flavor | q.v. |
| Color | q.v. |
| Purified water to | 5.0 ml |

The active ingredient, sucrose and xantham gum are blended, passed through a No. 10 mesh U.S. sieve, and mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 150 mg of active ingredient, are made as follows:

TABLE F8

| Ingredients | milligrams |
| --- | --- |
| Active ingredient | 150.0 |
| Starch | 407.0 |
| Magnesium stearate | 3.0 |
| Total | 560.0 |

The active ingredient, cellulose, starch, and magnesium stearate are blended, passed through a No. 20 mesh U.S. sieve, and filled into hard gelatin capsules in 560 mg quantities.

In the formulation examples, the "active ingredient" is a compound of the invention.

Kits

Various embodiments of the present invention include kits. Such kits can include a compound/bioconjugate of the present invention, optionally one or more ingredients for preparing a pharmaceutically acceptable formulation of the compound/bioconjugate, and instructions for use (e.g., administration). When supplied as a kit, different components of a compound/bioconjugate formulation can be packaged in separate containers and admixed immediately before use. Such packaging of the components separately can, if desired, be presented in a pack or dispenser device which can contain one or more unit dosage forms containing the compound/bioconjugate. The pack can, for example, comprise metal or plastic foil such as a blister pack. Such packaging of the components separately can also, in certain instances, permit long-term storage without losing activity of the components. In addition, if more than one route of administration is intended or more than one schedule for administration is intended, the different components can be packaged separately and not mixed prior to use. In various embodiments, the different components can be packaged in one combination for administration together.

It is further contemplated that the compounds and salts of this invention can be used in the form of a kit that is suitable for use in performing the methods described herein, packaged in a container. The kit can contain the compound or compounds and, optionally, appropriate diluents, devices or device components suitable for administration and instructions for use in accordance with the methods of the invention. The devices can include parenteral injection devices, such as syringes or transdermal patch or the like. Device components can include cartridges for use in injection devices and the like. In one aspect, the kit includes a first dosage form including a compound or salt of this invention and a second dosage form including another active ingredient in quantities sufficient to carry out the methods of the invention. The first dosage form and the second dosage form together can include a therapeutically effective amount of the compounds for treating the targeted condition(s).

In certain embodiments, kits can be supplied with instructional materials. Instructions can be printed on paper or other substrate, and/or can be supplied as an electronic-readable medium, such as a floppy disc, mini-CD-ROM, CD-ROM, DVD-ROM, Zip disc, videotape, audio tape, and the like. In an embodiment, detailed instructions are not physically associated with the kit; instead, a user can be directed to an Internet web site specified by the manufacturer or distributor of the kit, or supplied as electronic mail, for example.

Kits can include reagents in separate containers such as, for example, sterile water or saline to be added to a lyophilized active component packaged separately. For example, sealed glass ampules can contain lyophilized superoxide dismutase mimetics and in a separate ampule, sterile water, sterile saline or sterile each of which has been packaged under a neutral non-reacting gas, such as nitrogen. Ampules can consist of any suitable material, such as glass, organic polymers, such as polycarbonate, polystyrene, ceramic, metal or any other material typically employed to hold reagents. Other examples of suitable containers include bottles that can be fabricated from similar substances as ampules, and envelopes that can consist of foil-lined interiors, such as aluminum or an alloy. Other containers include test tubes, vials, flasks, bottles, syringes, and the like. Containers can have a sterile access port, such as a bottle having a stopper that can be pierced by a hypodermic injection needle. Other containers can have two compartments that are separated by a readily removable membrane that upon removal permits the components to mix. Removable membranes can be glass, plastic, rubber, and the like.

Example 6: Synthesis

The compounds of the invention can be synthesized according to the methods in references known to the art and using the provided procedures and modifications thereof known to one of ordinary skill in the art. Exemplary synthetic methods is provided in references including: M. E. Vol'pin, Russian Chemical Reviews, Vol. 29, No. 3 (1960), 129-160; Cowles, JACS, Vol. 79 (1957), 1093-1095; Hess, Tetrahedron, Vol. 31 (1975), 295-298; Anderson, J. Org. Chem., Vol. 29 (1964), 1373-1377; Nozoe, Chemistry and Industry (1954), 1357-1358; U.S. Pat. No. 5,846,730; Shevyakov, J. Phys. Chem., Vol. 107 (2003), 3295-3299; Murata, Chem. Phys. Lett., Vol. 13 (1972), 101-104; Pham, Angew. Chem. Int. Ed., Vol. 41 (2002) 3659-3662; Xu, Bioorganic & Medicinal Chemistry Letters, Vol. 11 (2001) 2045-2047; Wu, Anti-cancer drug design, Vol. 15 (2000), 287-293.

Exemplary synthetic schemes illustrating synthesis of several embodiments of the invention are shown below:

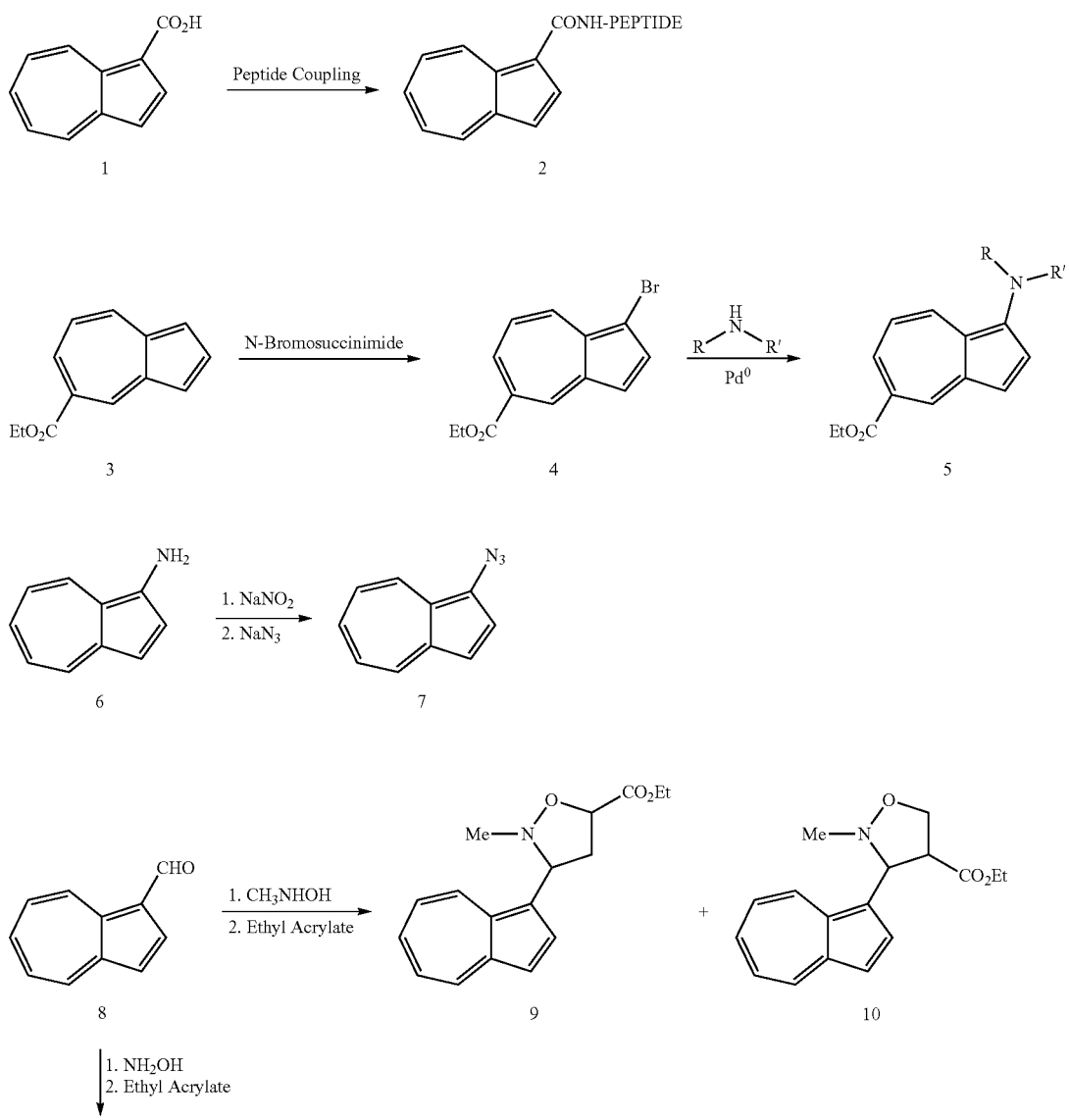

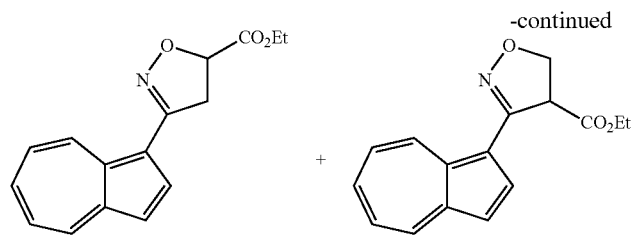

11          12

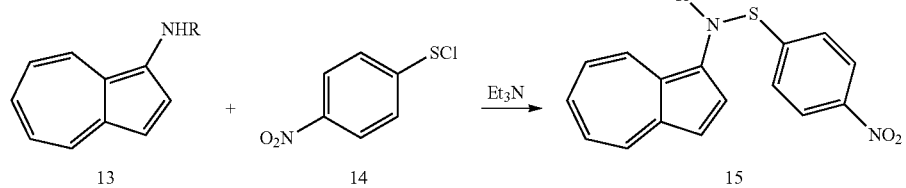

13    14    15

Peptide coupling can be carried out as known in the art by reacting a —COOH or —CONH(CH$_2$)$_a$CO$_2$H functional group on the azulene or azulene derivative using the reagent H$_2$N-Peptide and Coupling Agents, including but not limited to:

DCC
EDC
DCC, NHS
EDC, NHS
EDC, HOBt
PyBOP
PyBrOP
HATU
HBTU

Also provided below are exemplary synthetic methods for embodiments of the invention:

Solution Preparation of Preparation of Azulene-Peptide Conjugate 16 where Peptide=SFFYLRS (SEQ ID NO:1)

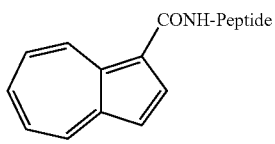

16

A mixture of 1-azulenecarboxylic acid (1 mmol), 1-hydroxybenzotriazole (1.2 mmol), and triethylamine (1.2 mmol) in DMF is stirred at ambient temperature for about 30 minutes. Thereafter, EDC (1.2 mmol) is then added and the entire mixture is stirred at ambient temperature for about 16 hours. The reaction mixture is then poured onto ethyl acetate to precipitate the product. Excess solvent is decanted off and the residue is repeatedly washed with ethyl acetate to remove excess DMF and the crude material is purified by HPLC.

Automated Procedure for Preparation of Azulene-Peptide Conjugate 16 where Peptide=SFFYLRS (SEQ ID NO:1)

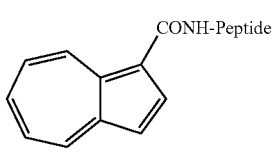

16

A typical procedure for the preparation of azulene-peptide conjugate 16 using an automated peptide synthesizer is described. It should be noted that other azulene fluorophores may be conjugated to leukemia binding and other targeting groups by the same procedure. The leukemia cell binding peptide conjugate pyrazine-S-F-F-Y-L-R-S(SEQ ID NO:1) (16) was prepared by fluorenylmethyloxycarbonyl (Fmoc) solid phase peptide synthesis strategy with a commercial automated peptide synthesizer. The first peptide cartridge contained Wang resin pre-loaded with an amide resin on 25 μmole scale. The amino acid cartridges each containing S, F, F, Y, L, R, and S amino acids were placed on the peptide synthesizer and the product was synthesized from the C- to the N-terminal sequence. Coupling of the Fmoc-protected amino acids to the resin-bound free terminal amine was carried out with 2-(1H-benzotriazol-1-yl)-1,1,3,3-tetramethyluronium hexafluorophosphate (HBTU, 75 μmol)/N-hydroxybenzotriazole (HOBt, 75 μmol). Each Fmoc protecting group on solid support was removed with 20% piperidine in dimethylformamide before the subsequent amino acid was coupled to it. The last cartridge contained the 1-azulenecarboxylic acid which was coupled to the

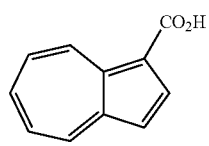 [SMILES: O=C(O)c1ccc2cccccc1-2]

peptide automatically, thus avoiding the need for post-synthetic manipulations. After the synthesis, the product was cleaved from the solid support with a cleavage mixture containing trifluoroacetic acid (85%):water (5%):phenol (5%):thioanisole (5%) for 6 hours. The peptide conjugate was precipitated with t-butyl methyl ether, collected by filtration, and purified by HPLC to give 60 mg of the desired pyrazine-peptide conjugate as a magenta powder.

| Table of Sequences | |
|---|---|
| SEQ ID NO: | SEQUENCE |
| 1 | S-F-F-Y-L-R-S |

Preparation of Azulene-mPEG$_{12}$ Derivative

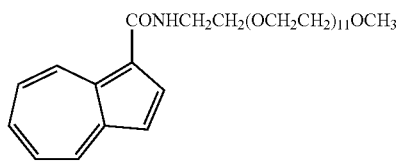

A mixture of the 1-azulene carboxylic acid (172 mg, 1.0 mmol) and m-PEG$_{12}$-amine (560 mg, 1.0 mmol) in anhydrous methylene chloride (10 mL) was stirred at ambient temperature for 15 minutes. Thereafter, 1-hydroxybenzotriazole (168 mg, 1.1 mmol) and ethyl dimethylaminopropyl carbodiimide (EDC) hydrochloride (210 mg 1.1 mmol) was added, and the entire mixture was stirred at ambient temperature for 16 hours. The reaction mixture was treated with 0.1 M HCl (10 mL) and the organic layer was separated, washed with water, dried over anhydrous sodium sulfate, filtered, and the filtrate evaporated to dryness in vacuo. The crude product was purified by flash chromatography using chloroform-methanol gradient (0 to 5% over 45 minutes) to give the desired material as magenta gum. LR/MS, 714.7 (M+H$^+$). UV, $\lambda_{max}$, 548 nm.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

The present compositions, preparations and formulations can be used both as a diagnostic agent as well as a photodynamic therapeutic agent concomitantly. For example, an effective amount of the present compositions, preparations and formulations in a pharmaceutically acceptable formulation is administered to a patient. Administration is followed by a procedure that combines photodiagnosis and phototherapy. For example, a composition comprising compounds for combined photodiagnosis and phototherapy is administered to a patient and its concentration, localization, or other parameters is determined at the target site of interest. More than one measurement may be taken to determine the location of the target site. The time it takes for the compound to accumulate at the target site depends upon factors such as pharmcokinetics, and may range from about thirty minutes to two days. Once the site is identified, the phototherapeutic part of the procedure may be done either immediately after determining the site or before the agent is cleared from the site. Clearance depends upon factors such as pharmacokinetics.

The present compositions, preparations and formulations can be formulated into diagnostic or therapeutic compositions for enteral, parenteral, topical, aerosol, inhalation, or cutaneous administration. Topical or cutaneous delivery of the compositions, preparations and formulations may also include aerosol formulation, creams, gels, solutions, etc. The present compositions, preparations and formulations are administered in doses effective to achieve the desired diagnostic and/or therapeutic effect. Such doses may vary widely depending upon the particular compositions employed in the composition, the organs or tissues to be examined, the equipment employed in the clinical procedure, the efficacy of the treatment achieved, and the like. These compositions, preparations and formulations contain an effective amount of the composition(s), along with conventional pharmaceutical carriers and excipients appropriate for the type of administration contemplated. These compositions, preparations and formulations may also optionally include stabilizing agents and skin penetration enhancing agents.

Methods of this invention comprise the step of administering an "effective amount" of the present diagnostic and therapeutic compositions, formulations and preparations containing the present compounds, to diagnose, image, monitor, evaluate, reduce or regulate a biological condition and/or disease state in a patient. The term "effective amount," as used herein, refers to the amount of the diagnostic and therapeutic formulation, that, when administered to the individual is effective diagnosis, image, monitor, evaluate treat, reduce or regulate a biological condition and/or disease state. As is understood in the art, the effective amount of a given composition or formulation will depend at least in part upon, the mode of administration (e.g. intravenous, oral, topical administration), any carrier or vehicle employed, and the specific individual to whom the formulation is to be administered (age, weight, condition, sex, etc.). The dosage requirements need to achieve the "effective amount" vary with the particular formulations employed, the route of administration, and clinical objectives. Based on the results obtained in standard pharmacological test procedures, projected daily dosages of active compound can be determined as is understood in the art. As used herein, "treat" means reduce or regulate a biological condition and/or disease state in a patient.

Any suitable form of administration can be employed in connection with the diagnostic and therapeutic formulations of the present invention. The diagnostic and therapeutic formulations of this invention can be administered intravenously, in oral dosage forms, intraperitoneally, subcutaneously, or intramuscularly, all using dosage forms well known to those of ordinary skill in the pharmaceutical arts.

The diagnostic and therapeutic formulations of this invention can be administered alone, but may be administered with a pharmaceutical carrier selected upon the basis of the chosen route of administration and standard pharmaceutical practice.

The diagnostic and therapeutic formulations of this invention and medicaments of this invention may further comprise one or more pharmaceutically acceptable carrier, excipient, buffer, emulsifier, surfactant, electrolyte or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985).

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein. As used herein, ranges specifically include the values provided as endpoint values of the range. As used herein, ranges specifically include all the integer values of the range. For example, a range of 1 to 100 specifically includes the end point values of 1 and 100.

All patents and publications mentioned in the specification are indicative of the levels of skill of those skilled in the art to which the invention pertains.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein. Any claim that is written in multiple dependent form or is a multiple dependent claim dependent on other multiple dependent claims is intended to include all claimed subject matter to the extent that each aspect can be included in a separate claim if necessary or desired.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed may be resorted to by those skilled in the art, and that such modifications and variations are considered to be within the scope of this invention as defined by the appended claims.

The disclosures of the publications listed herein including the publications listed below are herein incorporated by reference in their entireties.

REFERENCES

Shevyakov, V. et al. Orbital control of the color and excited state properties of formylated and fluorinated derivatives of azulene. *J. Phys. Chem.* 2003, 107, 3295-3299.

Murata, S. et al. Fluorescence yields of azulene derivatives. *Chem. Phys. Lett.* 1972, 13(2), 101-104.

Hess, B. A. Jr. et al. The aromaticity of heterocycles containing the imine nitrogen. *Tetrahedron* 1975, 31, 295-298.

Cowles, E. J. The effects of substituents at the 1- and 3-positions of the visible absorption spectrum of azulene. *J. Am. Chem. Soc.* 1957, 79, 1093-1095.

Anderson, A. G. et al. Some new reactions and derivatives of azulene. *J. Org. Chem.* 1964, 29, 1373-1377.

Nozoe, T. et al. Synthesis of 1-azaazulene and its derivatives. *Chem. Ind.* (London, UK) 1954, 1357-1358.

---

---

What is claimed is:

1. A compound of the formula (FX10):

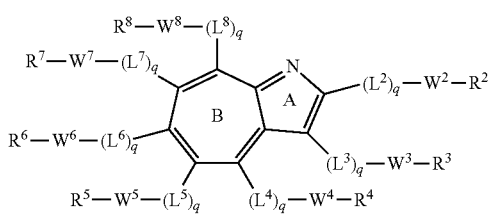

(FX10)

wherein:

each of $L^2$ to $L^8$ is independently selected from $C_1$-$C_{10}$ alkylene, $C_3$-$C_{10}$ cycloalkylene, $C_2$-$C_{10}$ alkenylene, $C_3$-$C_{10}$ cycloalkenylene, $C_2$-$C_{10}$ alkynylene, ethenylene, ethynylene, phenylene, 1-aza-2,5-dioxocyclopentylene, $-(CH_2CH_2O)_m-$, $-(CHOH)_m-$, or 1,4-diazacyclohexylene;

each m is independently selected from an integer selected from the range of 1 to 100;

each q is independently selected from 0 or 1;

each of $W^2$ to $W^8$ is independently selected from a single bond, $-(CH_2)_n-$, $-O(CH_2)_n-$, $-(CH_2)_nO-$, $-(HCCH)_n-$, $-O-$, $-S-$, $-SO-$, $-SO_2-$, $-SO_3-$, $-OSO_2-$, $-NR^9-$, $-CO-$, $-COO-$, $-OCO-$, $-OCOO-$, $-CONR^{10}-$, $-NR^{11}CO-$, $-OCONR^{12}-$, $-NR^{13}COO-$, $-NR^{14}CONR^{15}-$, $-NR^{16}CSNR^{17}-$, $-O(CH_2)_n-$, $-NR^{18}(CH_2)_n-$, $-CO(CH_2)_n-$, $-COO(CH_2)_n-$, $-OCO(CH_2)_n-$, $-OCOO(CH_2)_n-$, $-CONR^{19}(CH_2)_n-$, $-CONR^{20}(CH_2)_n(OCH_2CH_2)_u-$, $-NR^{21}CO(CH_2)_n-$, $-OCONR^{22}(CH_2)_n-$, $-NR^{23}COO(CH_2)_n-$, $-NR^{24}CONR^{25}(CH_2)_n-$, $-NR^{26}CSNR^{27}(CH_2)_n-$, $-O(CH_2)_nNR^{28}CO(CH_2)_n-$, $-CO(CH_2)_n(CH_2OCH_2)_n(CH_2)_nNR^{29}(CH_2)_nNR^{30}CO-$, $-NR^{69}SR^{70}-$, or $-CO(CH_2)_nNR^{31}CO-$;

each n is independently selected from an integer selected from the range of 1 to 10;

each of $R^9$ to $R^{31}$ and each of $R^{69}$ to $R^{70}$ is independently selected from hydrogen, $C_1$-$C_{20}$ alkyl, or $C_5$-$C_{30}$ aryl;

each $R^3$ to $R^8$ is independently selected from hydrogen, $C_1$-$C_{20}$ alkyl, $C_5$-$C_{30}$ aryl, $C_3$-$C_{20}$ acyl, $C_2$-$C_{20}$ alkenyl, $C_2$-$C_{20}$ alkynyl, $C_5$-$C_{20}$ alkylaryl, $C_1$-$C_6$ alkoxycarbonyl, halo, halomethyl, dihalomethyl, trihalomethyl, $-CN$, $-CO_2R^{32}$, $-CONR^{33}R^{34}$, $-COR^{35}$, $-NO_2$, $-SOR^{36}$, $-OSR^{37}-$, $-SO_2R^{38}$, $-SO_2OR^{39}$, $-SO_2NR^{40}R^{41}$, $-PO_3R^{42}R^{43}$, $-OR^{44}$, $-SR^{45}$, $-NR^{46}R^{47}$, $-NR^{48}COR^{49}$, $-CH_2(CHOH)_nR^{50}$, $-(CH_2CH_2O)_nR^{51}$, $-CH(R^{52})CO_2H$, $-CH(R^{53})NH_2$, $TG^1$ to $TG^8$, $PS^1$ to $PS^8$, or $FL^1$ to $FL^8$;

$R^2$ is $TG^1$, $PS^1$ or $FL^1$;

each u is independently selected from an integer selected from the range of 1 to 25;

each of $R^{32}$ to $R^{55}$ is independently selected from hydrogen or $C_1$-$C_{10}$ alkyl;

each of $TG^1$ to $TG^8$ is independently selected from an amino acid, a peptide, a protein, a nucleoside, a nucleotide, an enzyme, a carbohydrate, a glycomimetic, an oligomer, a lipid, a polymer, an antibody, an antibody fragment, a mono- or polysaccharide comprising 1 to 50 carbohydrate units, a glycopeptide, a glycoprotein, a peptidomimetic, a drug, a drug mimic, a hormone, a receptor, a metal chelating agent, a radioactive or nonradioactive metal complex, a mono- or polynucleotide comprising 1 to 50 nucleic acid units, a polypeptide comprising 2 to 30 amino acid units, or an echogenic agent;

each of $PS^1$ to $PS^8$ is independently selected from at least one azide, azo, diazo, oxaza, diaza, dithia, thioxa, dioxa, phthalocyanine, rhodamine, and porphyrin, and wherein each of $PS^1$ to $PS^8$ is capable of reacting to produce one or more free radicals selected from nitrenes, carbenes, and singlet oxygen; and each of $FL^1$ to $FL^8$ is independently selected from a fluorescent group selected from the group consisting of a naphthoquinone, an anthracene, an anthraquinone, a phenanthrene, a tetracene, a naphthacenedione, a pyridine, a quinoline, an isoquinoline, an indole, an isoindole, a pyrrole, an imidiazole, a pyrazole, a pyrazine, a purine, a benzimidazole, a benzofuran, a dibenzofuran, a carbazole, an acridine, an acridone, a phenanthridine, a thiophene, a benzothiophene, a dibenzothiophene, a xanthene, a xanthone, a flavone, a coumarin, a phenoxazine, a phenothiazine, a phenoselenazine, a cyanine, an indocyanine, and an azo compound;

wherein any adjacent $R^3$ to $R^8$ optionally combines with one or two $-CR^{54}R^{55}$ groups, to form $C_3$-$C_7$ cycloalkyl, $C_3$-$C_7$ heterocycloalkyl, $C_6$ aryl, or $C_5$-$C_6$ heteroaryl;

wherein at least one of $R^3$ to $R^8$ is $C_1$-$C_{10}$ alkyl, —$OR^{44}$, —$SR^{45}$, —$NR^{46}R^{47}$, or $NR^{48}COR^{49}$; and wherein at least one of $R^3$ to $R^8$ is halo, trihalomethyl, —CN, —$CO_2R^{32}$, —$CONR^{33}R^{34}$, —$COR^{35}$, —$NO_2$, —$SOR^{36}$, —$OSR^{37}$, —$SO_2R^{38}$, —$SO_2NR^{40}R^{41}$, or $C_3$-$C_{10}$ acyl; or wherein at least one of -$(L^2)_q$-$W^2$—$R^2$, $(L^3)_q$-$W^3$—$R^3$, $(L^4)_q$-$W^4$—$R^4$, $(L^5)_q$-$W^5$—$R^5$, $(L^6)_q$-$W^6$—$R^6$, -$(L^7)_q$-$W^7$—$R^7$, or -$(L^8)_q$-$W^8$—$R^8$ includes —$(OCH_2CH_2)_u$—.

2. The compound of claim 1, wherein at least one of $R^3$ to $R^8$ is independently selected from $C_1$-$C_6$ alkyl, —$OR^{44}$, —$SR^{45}$, —$NR^{46}R^{47}$, or $NR^{48}COR^{49}$.

3. The compound of claim 1, wherein at least one of $R^3$ to $R^8$ is independently selected from halo, trihalomethyl, —CN, —$CO_2R^{32}$, —$CONR^{33}R^{34}$, —$COR^{35}$, —$NO_2$, —$SOR^{36}$, —$SO_2R^{38}$, or —$SO_2NR^{40}R^{41}$.

4. The compound of claim 1, having R group substituent pairings ($R^3$ and $R^4$); ($R^4$ and $R^5$); ($R^5$ and $R^6$); ($R^6$ and $R^7$); ($R^7$ and $R^8$); ($R^3$ and $R^5$); or ($R^4$ and $R^7$), wherein one of the identified R groups in the substituent pairings is $C_1$-$C_{10}$ alkyl, —$OR^{44}$, —$SR^{45}$, —$NR^{46}R^{47}$, or $NR^{48}COR^{49}$ and the other of the identified R groups in the substituent pairings is halo, trihalomethyl, —CN, —$CO_2R^{32}$, —$CONR^{33}R^{34}$, —$COR^{35}$, —$NO_2$, —$SOR^{36}$, —$SO_2R^{38}$, or —$SO_2NR^{40}R^{41}$.

5. The compound of claim 1, wherein at least one of $R^3$ to $R^8$ is $FL^1$, $FL^2$, $FL^3$, $FL^4$, $FL^5$, $FL^6$, $FL^7$ or $FL^8$, or $R^2$ is $FL^1$.

6. The compound of claim 1, wherein each of $FL^1$ to $FL^8$ is independently selected from a naphthoquinone, an anthraquinone, a naphthacenedione, a pyrazine, an acridine, an acridone, a phenanthridine, a dibenzothiophene, a xanthene, a xanthone, a flavone, a coumarin, a phenoxazine, a phenothiazine, a phenoselenazine, a cyanine, an indocyanine, or an azo compound.

7. The compound of claim 1, wherein at least one of $R^3$ to $R^8$ is $PS^1$, $PS^2$, $PS^3$, $PS^4$, $PS^5$, $PS^6$, $PS^7$ or $PS^8$, or $R^2$ is $PS^1$.

8. The compound of claim 1, wherein at least one of $PS^1$ to $PS^8$ is independently selected from an azide, an azo, a diazo, an oxaza, a diaza, a thioxa, a phthalocyanine, a rhodamine, or a porphyrin group.

9. The compound of claim 1, wherein at least one of $R^3$ to $R^8$ is $TG^1$, $TG^2$, $TG^3$, $TG^4$, $TG^5$, $TG^6$, $TG^7$ or $TG^8$, or $R^2$ is $TG^1$.

10. The compound of claim 1, wherein each of $TG^1$ to $TG^8$ is independently selected from an amino acid, a peptide, a protein, a nucleoside, a nucleotide, an enzyme, an antibody, an antibody fragment, a mono- or polysaccharide comprising 1 to 50 carbohydrate units, a glycopeptide, a peptidomimetic, a drug, a drug mimic, or a hormone.

11. The compound of claim 1, wherein:

(b) one of $R^3$ and $R^4$ is $C_1$-$C_{10}$ alkyl, —$OR^{44}$, —$SR^{45}$, —$NR^{46}R^{47}$, or —$NR^{48}CO^{49}$, and the other of $R^3$ and $R^4$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$ or $C_3$-$C_{10}$ acyl;

(c) one of $R^4$ and $R^5$ is $C_1$-$C_{10}$ alkyl, —$OR^{44}$, —$SR^{45}$, —$NR^{46}R^{47}$, or —$NR^{48}CO^{49}$, and the other of $R^4$ and $R^5$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$ or $C_3$-$C_{10}$ acyl;

(d) one of $R^5$ and $R^6$ is $C_1$-$C_{10}$ alkyl, —$OR^{44}$, —$SR^{45}$, —$NR^{46}R^{47}$, or —$NR^{48}COR^{49}$, and the other of $R^5$ and $R^6$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_3$-$C_{10}$ acyl;

(e) one of $R^6$ and $R^7$ is $C_1$-$C_{10}$ alkyl, —$OR^{44}$, —$SR^{45}$, —$NR^{46}R^{47}$, or —$NR^{48}COR^{49}$, and the other of $R^6$ and $R^7$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_3$-$C_{10}$ acyl; or (f) one of $R^7$ and $R^8$ is $C_1$-$C_{10}$ alkyl, —$OR^{44}$, —$SR^{45}$, $NR^{46}R^{47}$, or —$NR^{48}COR^{49}$, and the other of $R^7$ and $R^8$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_3$-$C_{10}$ acyl.

12. The compound of claim 1, wherein:

(d) one of $R^3$ and $R^5$ is $C_1$-$C_{10}$ alkyl, —$OR^{44}$, —$SR^{45}$, —$NR^{46}R^{47}$, or —$NR^{48}COR^{49}$, and the other of $R^3$ and $R^5$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_3$-$C_{10}$ acyl; or (e) one of $R^4$ and $R^7$ is $C_1$-$C_{10}$ alkyl, —$OR^{44}$, —$SR^{45}$, —$NR^{46}R^{47}$, or —$NR^{48}COR^{49}$, and the other of $R^4$ and $R^7$ is halo, trihalomethyl, —CN, —$CO_2R^{32}$, —$CONR^{33}R^{34}$, —$COR^{35}$, —$NO_2$, —$SOR^{36}$, —$SO_2R^{38}$, —$SO_2NR^{40}R^{41}$, or $C_3$-$C_{10}$ acyl.

13. A pharmaceutical composition comprising:
a compound of claim 1; and a pharmaceutically acceptable excipient.

* * * * *

SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: SYNTHETIZED PEPTIDE

<400> SEQUENCE: 1

Ser Phe Phe Tyr Leu Arg Ser
1               5